US010300128B2

(12) United States Patent
Sala et al.

(10) Patent No.: US 10,300,128 B2
(45) Date of Patent: May 28, 2019

(54) SUBUNIT VACCINE PLATFORM BASED ON MULTIMERIC RIBONUCLEOPROTEINS COMPRISING NUCLEOPROTEINS OF A NON-SEGMENTED NEGATIVE-STRAND RNA VIRUS AS CARRIERS OF HETEROLOGOUS POLYPEPTIDES

(71) Applicants: INSTITUT PASTEUR, Paris (FR); CENTRE NATIONAL DE LA RECHERCHE SCIENTIFIQUE, Paris (FR); UNIVERSITE PARIS DIDEROT—PARIS 7, Paris (FR)

(72) Inventors: Monica Sala, Paris (FR); Daria Jacob, Paris (FR); Frederic Tangy, Les Lilas (FR)

(73) Assignees: INSTITUT PASTEUR, Paris (FR); CENTRE NATIONAL DE LA RECHERCHE SCIENTIFIQUE, Paris (FR); UNIVERSITE PARIS DIDEROT—PARIS 7, Paris (FR)

( * ) Notice: Subject to any disclaimer, the term of this patent is extended or adjusted under 35 U.S.C. 154(b) by 21 days.

(21) Appl. No.: 15/034,870

(22) PCT Filed: Sep. 17, 2014

(86) PCT No.: PCT/EP2014/069830
§ 371 (c)(1),
(2) Date: May 5, 2016

(87) PCT Pub. No.: WO2015/071009
PCT Pub. Date: May 21, 2015

(65) Prior Publication Data

US 2016/0271242 A1 Sep. 22, 2016

(30) Foreign Application Priority Data

Nov. 18, 2013 (EP) .................................... 13306577

(51) Int. Cl.

| | |
|---|---|
| ***A61K 39/165*** | (2006.01) |
| ***C12N 7/00*** | (2006.01) |
| ***A61K 39/015*** | (2006.01) |
| ***A61K 39/125*** | (2006.01) |
| ***C07K 14/005*** | (2006.01) |
| ***C07K 14/445*** | (2006.01) |
| ***C12N 15/81*** | (2006.01) |
| *A61K 39/00* | (2006.01) |

(52) U.S. Cl.
CPC .......... *A61K 39/165* (2013.01); *A61K 39/015* (2013.01); *A61K 39/125* (2013.01); *C07K 14/005* (2013.01); *C07K 14/445* (2013.01); *C12N 7/00* (2013.01); *C12N 15/815* (2013.01); *A61K 2039/521* (2013.01); *A61K 2039/523* (2013.01); *A61K 2039/542* (2013.01); *A61K 2039/545* (2013.01); *A61K 2039/57* (2013.01); *A61K 2039/575* (2013.01); *A61K 2039/6031* (2013.01); *A61K 2039/6075* (2013.01); *A61K 2039/70* (2013.01); *C07K 2319/85* (2013.01); *C12N 2760/18422* (2013.01); *C12N 2760/18434* (2013.01); *C12N 2760/18451* (2013.01); *C12N 2760/18471* (2013.01); *C12N 2770/32322* (2013.01); *C12N 2770/32334* (2013.01); *C12N 2770/32351* (2013.01); *Y02A 50/412* (2018.01)

(58) Field of Classification Search
CPC ........ C12N 15/86; C12N 15/11; C12N 15/87; C12N 2710/10362; C12N 2760/18643
See application file for complete search history.

(56) References Cited

U.S. PATENT DOCUMENTS 8,986,706 B2 * 3/2015 Bublot ................ A61K 39/245 424/184.1

FOREIGN PATENT DOCUMENTS

WO 2007/119011 A2 10/2007
WO 2009/095791 A1 8/2009

OTHER PUBLICATIONS

Rimantas Slibinskas et al: "Synthesis of the measles virus nucleoprotein in yeast *Pichia pastoris* and *Saccharomyces cerevisiae*", Journal of Biotechnology, vol. 107, No. 2, Jan. 1, 2004 (Jan. 1, 2004), pp. 115-124.
Regules Jason A et al: "The RTS,S vaccine candidate for malaria", Expert Review of Vaccines England, Expert Reviews Ltd, GB, vol. 10, No. 5, May 1, 2011 (May 1, 2011) pp. 589-599.

(Continued)

*Primary Examiner* — Bao Q Li
(74) *Attorney, Agent, or Firm* — Arrigo, Lee, Guttman & Mouta-Bellum LLP

(57) ABSTRACT

The present invention relates to a subunit vaccine platform based on multimeric ribonucleoproteins (RNPs) comprising nucleoproteins of a non-segmented negative-strand ribonucleic acid (RNA) virus as carriers of heterologous polypeptides. The present invention also relates to multimeric RNPs resulting from the assembly of at least 200 fusion proteins with a cellular RNA, or to recombinant yeasts or yeast lysates expressing these multimeric RNPs. It also concerns a process for the preparation of these multimeric RNPs or recombinant yeasts or yeast lysates. In particular, the present invention relates to their use as active ingredient for the in vitro production of an immunogenic composition or in eliciting a protective prophylactic or a therapeutic immune response against said heterologous polypeptide in a host in need thereof. Recombinant yeasts or yeast lysates of the invention can also be used as expression and vector systems for delivery to a host.

18 Claims, 26 Drawing Sheets

Specification includes a Sequence Listing.

(56) References Cited

OTHER PUBLICATIONS

Daria Jacob et al: “Whole Pichia pastoris Ye a s t Expressing Measles Virus Nucleoprotein as a Production and Delivery System to Multimerize Plasmodium Antigens”, Plos One, vol. 9, No. 1, Jan. 27, 2014 (Jan. 27, 2014), p. e86658.
International Search Report, Application No. PCT/EP2014/069830, dated Dec. 22, 2014.
European Search Report, Application No. EP 13 30 6577, dated Feb. 20, 2014.

* cited by examiner

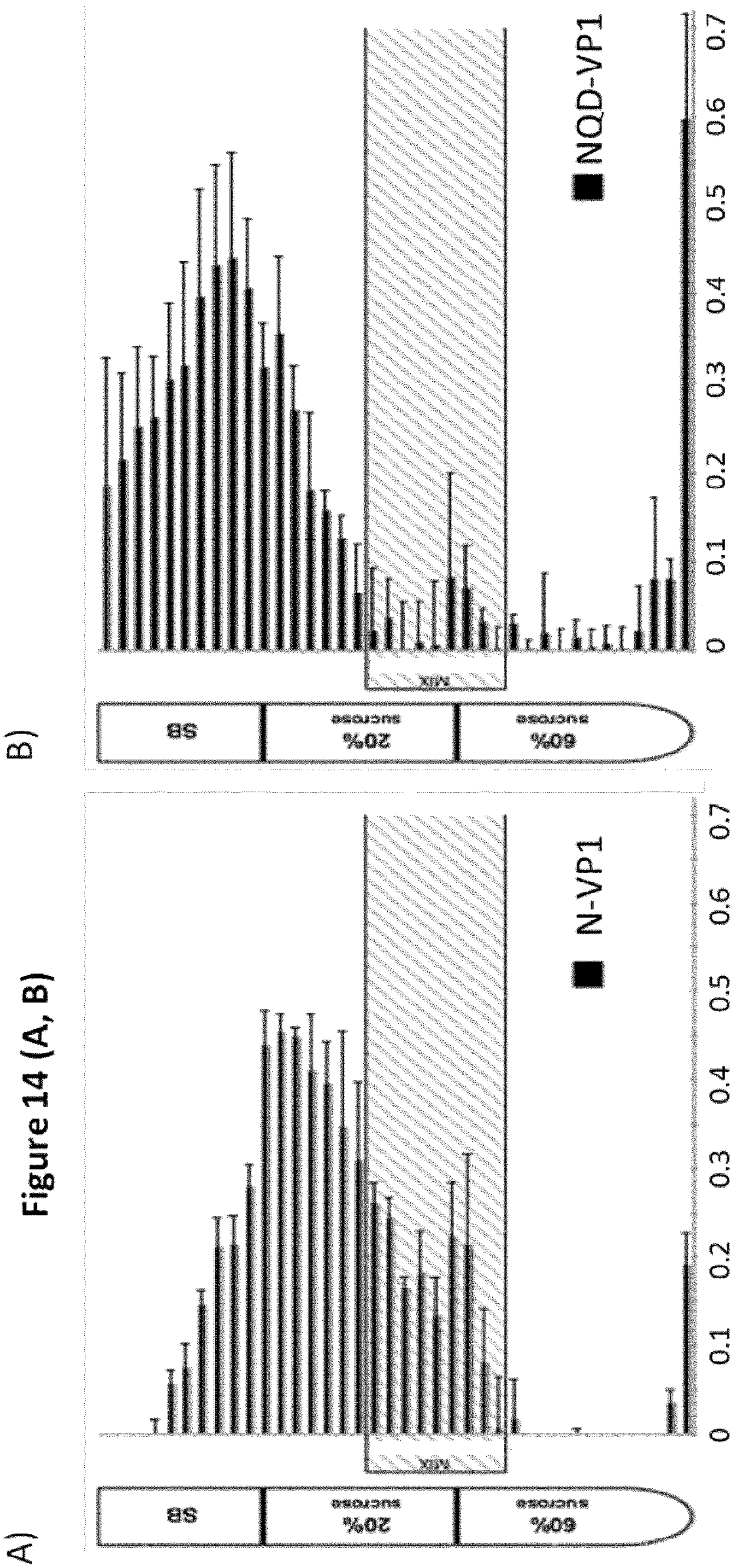
Figure 14 (A, B)

C)
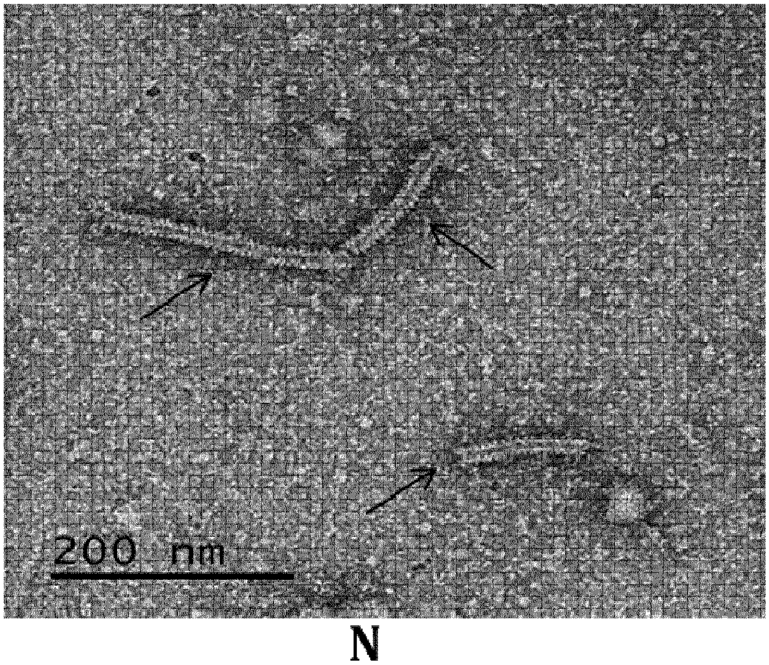
N
D)
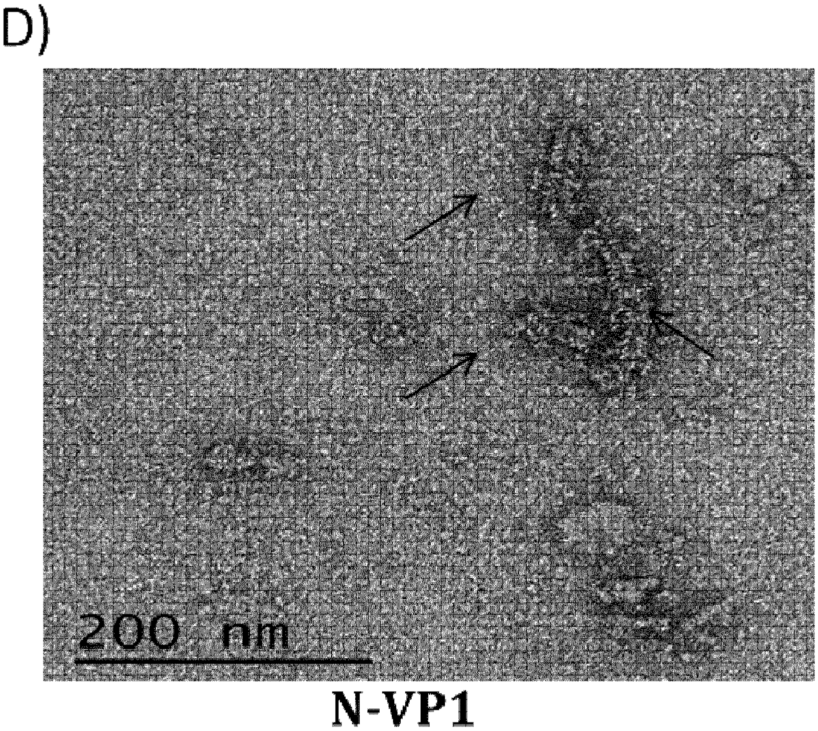
N-VP1
Figure 14 (C, D)

A)

GAAGAGA

| core | tail | | repeat region | |
|------|------|--|---------------|--|

MV-N — 1 — 525

PbCS — 27 — 327

B) N standard | N-PbCS in SMD1168

10 ng, 12 ng, 14 ng, 16 ng, 18 ng, 20 ng | 1/24, 1/18, 1/12, 1/9, 1/8, 1/6

130 kDa
95 kDa
70 kDa
55 kDa

C) N standard | N in SMD1168

10 ng, 12 ng, 14 ng, 16 ng, 18 ng, 20 ng | 1/3000, 1/1500, 1/1000

70 kDa
55 kDa

A)

```
            |   10      |   20      |   30      |   40      |   50        |   60      |   70      |   80      |   90      |  100
   1 ATGGCCACGT TATTGAGATC TTTAGCCCTT TTTAAGAGGA ACAAGGACAA  ACCCCCAATT ACAAGTGGTT CTGGTGGAGC TATTCGTGGT ATTAAGCACA    100
 101 TTATTATCGT GCCCATTCCA GGGGATTCAA GTATCACCAC CCGAAGTAGA  TTGTTGGACA GATTGGTCCG ACTTATAGGG AACCCAGACG TTAGTGGACC    200
 201 CAAGCTGACC GGGGCTCTGA TCGGAATCTT ATCTTTGTTC GTTGAATCTC  CAGGACAGTT AATCCAAAGG ATTACAGACG ATCCAGACGT CTCTATTAGG    300
 301 CTTCTAGAGG TTGTTCAGTC TGACCAGTCT CAATCCGGTC TTACCTTCGC  TTCAAGAGGT ACCAATATGG AGGACGAAGC CGATCAATAT TTCTCACATG    400
 401 ACGATCCTAT CTCCTCCGAC CAATCAAGAT TTGGTTGGTT CGGAAACAAA  GAGATCTCTG ACATTGAGGT TCAGGACCCA GAAGGATTTA ACATGATACT    500
 501 GGGAACTATC CTTGCACAAA TCTGGGTGCT GCTGGCTAAA GCCGTTACTG  CTCCAGACAC CGCTGCTGAT TCCGAATTAC GAAGATGGAT TAAATACACT    600
 601 CAACAACGTA GAGTAGTTGG TGAATTTAGA TTGGAGAGAA AGTGGTTGGA  TGTTGTGAGA AACAGAATTG CAGAAGACCT ATCACTGAGA CGATTTATGG    700
 701 TCGCTCTTAT ACTGGATATT AAGAGGACAC CAGGAAACAA GCCAAGGATT  GCAGAAATGA TCTGTGATAT AGATACTTAC ATCGTTGAGG CCGGGTTGGC    800
 801 TTCCTTTATT CTAACTATAA AATTTGGTAT CGAGACAATG TACCCAGCAT  TGGGATTGCA TGAGTTCGCC GGAGAACTGT CAACATTGGA GTCATTGATG    900
 901 AATCTATACC AGCAAATGGG TGAAACAGCT CCATATATGG TCATTCTGGA  AAACTCCATT CAAAACAAGT TTTCAGCCGG TTCATACCCA TTATTGTGGT   1000
1001 CTTACGCCAT GGGAGTCGGT GTAGAGCTGG AAAACTCTAT GGGTGGCCTT  AATTTCGGCA GATCTTATTT TGATCCCGCT TATTTTAGAC TGGGCCAAGA   1100
1101 GATGGTCAGA CGTTCTGCCG GAAAGGTTTC TAGTACTTTG GCTAGTGAAC  TAGGTATAAC TGCTGAGGAC GCTAGATTGG TTTCTGAAAT AGCTATGCAC   1200
1201 ACTACTGAAG ATAAGATCAG TAGGGCCGTT GGCCCTAGGC AAGCTCAGGT  GTCCTTCTTA CATGGTGATC AATCCGAGAA TGAGTTGCCT CGATTGGGAG   1300
1301 GCAAAGAGGA CCGTAGAGTT AAACAATCTA GAGGAGAGGC ACGTGAATCT  TACAGAGAGA CCGGTCCATC CCGAGCTTCT GATGCACGAG CCGCTCATCT   1400
1401 TCCTACCGGT ACACCTTTAG ACATTGATAC GGCAACGGAA TCATCCCAGG  ATCCCCAAGA TTCTAGACGT TCTGCTGATG CTTTACTAAG ATTGCAGGCT   1500
1501 ATGGCCGGAA TTTCAGAGGA GCAAGGTTCC GACACAGATA CTCCAATTGT  CTATAATGAC CGAAATCTGT TAGAT                             1577
            |   10      |   20      |   30      |   40      |   50        |   60      |   70      |   80      |   90      |  100
```

B)

```
            |   10      |   20      |   30      |   40      |   50        |   60      |   70      |   80      |   90      |  100
   1 GGCGCCGCGG GAGCAGGTGC ATCCATCCAG GCCCAGAGAA ACTTGAACGA  ACTTTGCTAC AACGAAGGAA ACGACAACAA ACTTTACCAC GTCTTGAACT    100
 101 CTAAGAATGG TAAAATCTAC AACAGAAACA CAGTTAACAG ATTGCTTGCT  GATGCCCCAG AAGGAAAGAA AAATGAGAAG AAAAACGAAA AGATCGAGAG    200
 201 AAACAATAAG TTGAAACAAC CTCCTCCACC TCCAAATCCA AACGATCCTC  CACCTCCAAA TCCTAACGAC CCACCTCCAC CTAACCCTAA TGACCCACCT    300
 301 CCACCTAATC CTAACGACCC TCCACCTCCA AATGCTAATG ACCCACCTCC  TCCAAATGCA AACGACCCAG CTCCTCCAAA TGCCAACGAT CCTGCACCTC    400
 401 CAAATGCTAA CGACCCAGCC CCTCCAAATG CAAACGATCC TGCCCCTCCA  AATGCCAATG ATCCACCTCC ACCTAATCCA AATGACCCAG CACCACCAAA    500
 501 TGCCAATGAT CCTCCTCCAC CTAACCCAAA CGATCCTGCT CCTCCACAGG  GTAACAATAA CCCTCAACCA CAGCCTAGAC CACAACCTCA GCCTCAGCCT    600
 601 CAGCCACAAC CACAACCACA ACCTCAGCCA CAACCTAGAC CACAGCCTCA  ACCACAGCCT GGTGGAAATA ATAATAACAA AAACAACAAC AACGATGACT    700
 701 CTTATATTCC ATCCGCCGAA AAGATCCTTG AGTTTGTCAA GCAAATCAGA  GACTCAATCA CCGAAGAGTG GAGTCAATGT AATGTTACTT GCGGTTCTGG    800
 801 AATTAGAGTC AGAAAGAGAA AAGGTTCTAA CAAGAAAGCT GAAGATTTGA  CTCTTGAGGA TATCGACACA GAGATTTGTA AGATGGATAA GTGCTCAAGT    900
 901 ATTTTCAACA TTGTCAGTAA CTCATAGTAG                                                                                930
            |   10      |   20      |   30      |   40      |   50        |   60      |   70      |   80      |   90      |  100
```

C)

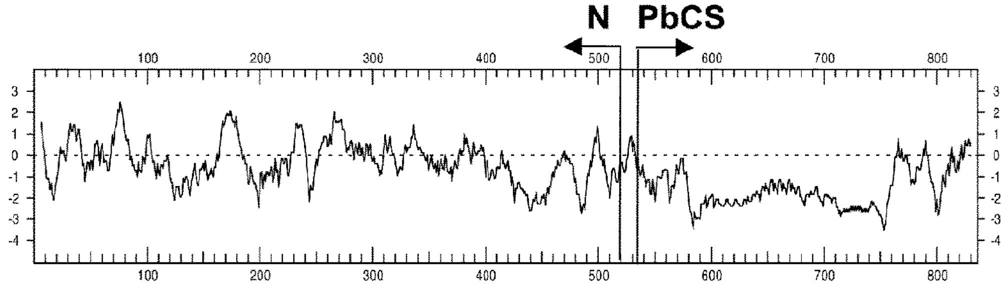

Figure 21

SUBUNIT VACCINE PLATFORM BASED ON MULTIMERIC RIBONUCLEOPROTEINS COMPRISING NUCLEOPROTEINS OF A NON-SEGMENTED NEGATIVE-STRAND RNA VIRUS AS CARRIERS OF HETEROLOGOUS POLYPEPTIDES

SEQUENCE LISTING

The instant application contains a Sequence Listing which has been submitted electronically in ASCII format and is hereby incorporated by reference in its entirety. Said ASCII copy, created on Feb. 16, 2018, is named B10277AD_SL.txt and is 117,589 bytes in size.

The present invention relates to a subunit vaccine platform based on multimeric ribonucleoproteins (RNPs) comprising nucleoproteins of a non-segmented negative-strand ribonucleic acid (RNA) virus as carriers of heterologous polypeptides. The present invention also relates to multimeric RNPs resulting from the assembly of at least 200 fusion proteins with a cellular RNA, or to recombinant yeasts or yeast lysates expressing these multimeric RNPs. It also concerns a process for the preparation of these multimeric RNPs or recombinant yeasts or yeast lysates. In particular, the present invention relates to their use as active ingredient for the in vitro production of an immunogenic composition or in eliciting a protective prophylactic or a therapeutic immune response against said heterologous polypeptide in a host in need thereof. Recombinant yeasts or yeast lysates of the invention can also be used as expression and vector systems for delivery to a host.

Immunogen or epitope delivery is a major issue in the success of vaccines. Although only a few adjuvants are licensed (http://www.fda.gov/BiologicsBloodVaccines/SafetyAvailability/VaccineSafety/ucm187810.htm, *Vaccines, Blood & Biologics,* 2011), a large array of chemical-based new adjuvants or immunostimulants for vaccine polypeptides are currently developed (Ribeiro, C M, Schijns V E, 2010, *Methods Mol Biol* 626: 1-14). However, several concerns about the safety of using chemicals in association with vaccines are raised (Bagnoli F et al., 2011, *OMICS* 15: 545-566; Tomljenovic L, 2011, *J Alzheimers Dis* 23: 567-598; Francois G et al., 2005, *Pediatr Infect Dis J* 24: 953-961; Piyasirisilp S, Hemachudha T, 2002, *Curr Opin Neurol* 15: 333-338; Miller E et al., 2013, *BMJ* 346: f794). Therefore, alternative delivery strategies need to be developed. Among them, the use of attenuated (Lacerda C M et al., 2011, *Mycopathologia* 171: 395-401) or inactivated (Stubbs A C et al., 2001, *Nat Med* 7: 625-629; Roohvand F, Kossari N, 2012, *Expert Opin Ther Pat* 22: 391-415; Bian G et al., 2009, *Vaccine* 28: 187-194) yeast is emerging. Yeast-based vaccines elicit both humoral and cell-mediated immune responses in the absence of adjuvants (Stubbs A C et al., 2001, *Nat Med* 7: 625-629; Roohvand F, Kossari N, 2012, *Expert Opin Ther Pat* 22: 391-415; Bian G et al., 2009, *Vaccine* 28: 187-194). Heat-killed yeasts have been shown to protect mice against systemic aspergillosis and coccidioidomycosis (Liu M et al., 2011, *Vaccine* 29: 1745-1753), or to provide sterile protection to chicken towards infectious bursal disease (Arnold M et al., 2012, *PLoS One* 7: e42870). Recombinant yeasts are currently developed as vaccine candidates against HBV and HCV in humans (Haller A A et al., 2007, *Vaccine* 25: 1452-1463) or leukemia (Bui M R et al., 2010, *Vaccine* 28: 6028-6035). Yeasts under the form of whole yeasts activate dendritic cells (DCs) and are efficiently taken up through fungipods or phagocytic synapses on DCs (Neumann A K, Jacobson K, 2010, *PLoS Pathog* 6: e1000760; Goodridge H S et al., 2011, *Nature* 472: 471-475). Both mannose and Dectin-1 receptors mediate the interaction between human DCs and the most biotechnologically relevant yeasts: *Saccharomyces cerevisiae* (*S. cerevisiae*) and *Pichia pastoris* (*P. pastoris*) (Bazan S B et al., 2011, *Vaccine* 29: 8165-8173). DCs can distinguish direct fungal contacts from soluble fungal-derived components through the Dectin-1 pattern-recognition receptor (Goodridge H S et al., 2011, *Nature* 472: 471-475). Thus, activated DCs become potent presenting cells for antigens expressed in recombinant yeast, and efficiently deliver antigens into both MHC class I and class II pathways. Hence, yeast-DC interplay provides a strong adjuvant effect on antigen immunogenicity (Stubbs A C et al., 2001, *Nat Med* 7: 625-629; Roohvand F, Kossari N, 2012, *Expert Opin Ther Pat* 22: 391-415; Bian G et al., 2009, *Vaccine* 28: 187-194; Saiki M et al., 2005, *J Autoimmun* 24, 203-208).

Multimerization of monomeric antigens was also largely demonstrated to amplify their immunogenicity through increased uptake by DCs (Arias M A et al., 2011, *Vaccine* 29: 1258-1269; Singh M et al, 2007, *Expert Rev Vaccines* 6: 797-808; Xiang S D et al., 2006, *Methods* 40: 1-9; Storni T et al., 2005, *Adv Drug Deliv Rev* 57: 333-355). Several multimeric proteins, generally from viral origin, have been used as delivery systems (Casares S et al., 2010, *Vaccine* 28: 4880-4894; Gonzalez M C et al., 2009, *Virus Res* 146: 107-114; Vietheer P T et al., 2007, *Antivir Ther* 12: 477-487; Jariyapong P et al., 2013, *Vaccine* 31: 417-424).

The nucleoprotein (N) of measles virus (MV), which composes the viral helical nucleocapsid (Griffin D E et al., 2012, *FEMS Microbiol Rev* 36: 649-662; Griffin D E, 2001, *Fields Virology. Philadelphia: Lippincott Williams & Wilkins Publications*. pp. 1401-1441), has the capacity to auto-assemble around any RNA molecule in the cytoplasm of cells in which this protein is expressed including in mammalian (Bourhis J M, Canard B, Longhi S, 2006, *Virology* 344: 94-110), bacterial (Warnes A et al., 1995, *Gene* 160: 173-178) or yeast cells (Slibinskas R et al., 2004, *J Biotechnol* 107: 115-124)) with a ratio of 1 N molecule to 6 ribonucleotides. This gives rise to helical, highly stable, and multimeric RNPs similar in shape and diameter to RNPs present in MV viral particles (Jensen M R et al., 2011, *Proc Natl Acad Sci U S A* 108: 9839-9844). The expression of MV-N protein in *P. pastoris* GS115 yeast strain induces the formation of high amounts of these RNPs visible in the cytoplasm by electron microscopy, without the help of other measles virus viral proteins (Slibinskas R et al., 2004, *J Biotechnol* 107: 115-124).

Vaccine manufacturers largely use yeast as bioreactor for producing high amounts of low cost vaccines, the best example being the anti-hepatitis B (HBV) vaccine (ENGERIX-B®). This vaccine is based on the HBV small surface antigen (HBsAg) and is manufactured in *S. cerevisiae* yeast. Like in all yeast-based vaccines currently on the market, ENGERIX-B® HBsAg is produced and purified from yeasts. Attempts to validate *S. cerevisiae* as both an antigen bioreactor and a delivery system are currently ongoing in preclinical and clinical trials. An HCV therapeutic vaccine (GI-5005) was tested in Phase IIb, and an HBV therapeutic vaccine (GI-13000) is undergoing preclinical studies (http://www.globeimmune.com/). These vaccine candidates are based on *S. cerevisiae*, as most whole yeast-based vaccine candidates (Liu Met al., 2011, *Vaccine* 29: 1745-1753; Bui M R et al., 2010, *Vaccine* 28: 6028-6035). In 2009 the entire genome of *P. pastoris* yeast (GS115 strain) was sequenced (De Schutter K et al., 2009, *Nat Biotechnol* 27: 561-566). This encouraged the development of *P. pas-*

*toris* as bioreactor in vaccinology. Indeed, *P. pastoris* may offer advantages compared to *S. cerevisiae*, such as the stringent control of protein production through a strong inducible promoter and the reduced length of the oligosaccharide chains eventually added post-translationally to transgenic proteins. Moreover, terminal α-1,3 glycan linkages on glycosylated proteins, which are responsible for hyper-antigenicity effects of antigens produced in *S. cerevisiae* (Cregg J M et al., 1993, *Biotechnology* (*N Y*) 11: 905-910), are not formed in *P. pastoris*. Thus, *P. pastoris* is an interesting alternative in the development of whole yeast vaccines, since this species introduces less post-translational modifications on heterologous antigens than *S. cerevisiae* (Cregg J M et al., 1993, *Biotechnology* (*N Y*) 11: 905-910). Moreover, unlike *S. cerevisiae, P. pastoris* is particularly suitable for the fermentative growth and has the ability to reach very high cell densities during fermentation, which may improve overall protein yields (Liu R et al., 2009, *Appl Biochem Biotechnol* 158: 432-444).

International patent application WO2007/119011 discloses fusion proteins, wherein the protein of interest, e.g. an antigen derived from a pathogenic microorganism such as a *Plasmodium* parasite, is fused at the C-terminal end of the N protein of a virus of the Paramyxoviridae family, e.g. the measles virus. These fusion proteins are expressed in *E. Coli* and purified in the form of soluble rings, containing 10 molecules of N protein and a RNA of bacterial origin, which are proposed in applications for vaccination and intracellular vectorisation.

The fusion of a polypeptide (in particular a polypeptide bearing epitope(s) or an antigen) to another (N protein as a vector protein) may impact the vector protein folding and/or general properties. In particular, if the vector protein auto-assembles into a quaternary structure (i.e. MV RNPs), fusion of this protein with a heterologous one may impair its association. In the case of HBV VLPs, it was demonstrated that the length and the amino acid composition, the presence of cysteine residues and/or of ATG codons in the three reading frames, and hydrophobicity of proteins/peptides fused in N-terminal to the HBsAg protein (auto-assembling into HBV VLPs) can greatly impact the efficiency of VLP assembly and their immunogenicity (Gonzales M C et al. 2009, *Virus research* 146: 107-114; Berkower et al. 2004, *Virology* 321: 75-86; Cheong et al. 2009, *J. Virol. Methods* 158: 35-40; Mancini et al. 1994, *Int. Rev. lmmunol.* 11: 143-151; Michel et al. 2007 *Vaccine* 25 :1901-1911). Notably, the GSK anti-*Plasmodium falciparum* vaccine, which comprises an adjuvant, is based on these VLPs (high doses) (WO93/10152; Vanloubbeeck Y et al. 2013. *Vaccine*).

International patent application WO2009/095791 discloses a method for the generation by reverse genetics of infectious ribonucleoparticles (RNPs), RNPs-like of measles virus or such RNPs fused with a heterologous sequence, said method being carried out in recombinant yeast, e.g. in *S. cerevisiae* or *P. Pastoris*. It discloses the production and purification of MV-RNPs in yeast.

International patent application WO2010/033841 discloses the use of heat-inactivated, whole yeast, e.g. *P. pastoris*, in the preparation of an immunotherapeutic composition to treat chronic hepatitis C virus.

Patent applications U.S. Pat. Nos. 5,830,463, 8,221,763 and EP0789593 are directed to yeast-based delivery vehicles, e.g. *P. pastoris*-based delivery vehicles, and their use to deliver a variety of compounds to different cell types. Yeast vehicles do not need to be administered with an adjuvant, and are capable of protecting an animal from an infection, e.g. from a *Plasmodium* infection.

Major challenges in vaccinology are to develop new antigen production and delivery strategies and to bypass chemical adjuvants for safety concerns. The present invention addresses these issues.

To evaluate a new vaccine platform based on recombinant yeast as epitope delivery vector for multimerized polypeptides, the inventors used a malaria animal model. Despite major research efforts, an efficient malaria vaccine is indeed still not available (Daily J P, 2012, *N Engl J Med* 367: 2349-2351). Hence, it is worthwhile to investigate new approaches.

Malaria is a life-threatening disease caused by the multiplication of *Plasmodium* parasites in the blood after injection in the skin by a female *Anopheles* mosquito. *Plasmodium* parasites that are known to infect humans are *Plasmodium vivax, Plasmodium ovale, Plasmodium malariae, Plasmodium knowlesi* and *Plasmodium falciparum*, the latter being the most prominent parasite that causes the majority of human deaths. The parasite forms in the skin, called sporozoites, enter the bloodstream and invade liver cells, where they multiply into merozoites. Then, following the rupture of the liver cells, these merozoites infect red blood cells and undergo multiple nuclear divisions to give rise to further merozoites capable of invading additional red blood cells (Miller L H et al., 2013, *Nat Med* 19: 156-167).

The *Plasmodium* sporozoite is covered with the circumsporozoite protein (CS), the leading vaccine candidate against the pre-erythrocytic stage of *Plasmodium*. The CS protein is present on the surface of *Plasmodium* sporozoites (10 pg per sporozoite; Kumar S et al., 2013, *J Immunol Methods* 390: 99-105) when they are inoculated into the skin of the host (Miller L H et al., 2013, *Nat Med* 19: 156-167; Nussenzweig V, Nussenzweig R S, 1985, *Cell* 42: 401-403; Gueirard P et al., 2010, *Proc Natl Acad Sci U S A* 107: 18640-18645). Antibodies to CS (Kester K E et al., 2009, *J Infect Dis* 200: 337-346; John C C et al., 2005, *Am J Trop Med Hyg* 73: 222-228; Schofield L et al., 1987, *Nature* 330: 664-666), as well as specific CD8+ T cells (Schofield L et al., 1987, *Nature* 330: 664-666; Weiss W R et al., 1988, *Proc Natl Acad Sci U S A* 85: 573-576; Radosevic K et al., 2010, *Clin Vaccine Immunol* 17: 1687-1694), are known to protect against sporozoite challenge in animal models, primarily rodents. In humans, the most advanced malaria vaccine candidate (RTS,S) is based on this CS antigen (Regules J A et al., 2011, *Expert Rev Vaccines* 10: 589-599). In RTS,S, CS multimerization is achieved by its association to hepatitis B virus-like particles. Full results from the phase III trial of RTS,S are expected in 2015. Current estimates of vaccine efficacy in the 12 months following three doses were 30-56%, depending on age group and endpoint (Agnandji S T et al., 2012, *N Engl J Med* 367: 2284-2295). Nevertheless, recent phase IIb analysis showed that RTS,S efficacy is inversely correlated with transmission intensity, dropping to zero in a three-year perspective (Bejon P et al., 2013, *Lancet Infect Dis*). This is in strong support for developing second-generation malaria vaccine strategies.

The inventors set up a delivery system based on the heterologous expression of measles virus nucleoprotein (MV-N) in *P. pastoris*. The inventors showed that the spontaneous auto-assembly of this protein in association with cellular RNA in *P. pastoris* provided a mean or vector to multimerize heterologous polypeptides. As a proof of concept, the inventors fused to MV-N the circumsporozoite protein (CS) from *Plasmodium berghei* (Pb), the etiologic agent of rodent malaria (Scheller L F et al., 1994, *Infect Immun* 62: 4844-4847).

The present invention thus relates to multimeric ribonucleoproteins (RNPs) resulting from the assembly of at least 200 fusion proteins with a cellular ribonucleic acid (RNA), wherein the fusion protein comprises a nucleoprotein (N) of a non-segmented negative-strand RNA virus of the Paramyxoviridae family fused directly or indirectly with a heterologous polypeptide carrying one or a plurality of epitopes.

In a particular embodiment, the present invention relates to multimeric ribonucleoproteins (RNPs) resulting from the assembly of at least 200 fusion proteins with a cellular ribonucleic acid (RNA), wherein the fusion protein consists of a nucleoprotein (N) of a non-segmented negative-strand RNA virus of the Paramyxoviridae family fused directly or indirectly with a heterologous polypeptide carrying one or a plurality of epitopes.

A nucleoprotein according to the invention encompasses a native nucleoprotein from a MV virus, in particular a N protein from MV Schwarz or from MV Moraten. It also relates to a variant or to a mutant form of a native nucleoprotein from a MV virus. It also encompasses a nucleoprotein which has undergone post-translational modifications, e.g. a glycosylated nucleoprotein.

In a preferred embodiment of the invention, the nucleoprotein and optionally the heterologous polypeptide is (are) glycosylated, especially as a result of yeast glycosylation, such as glycosylation by *P. pastoris* or *S. cerevisiae.*

In the present invention, the term "ribonucleoprotein" is abbreviated RNP.

As defined herein, the term "ribonucleoprotein (RNP)" refers to a quaternary structure containing a cellular ribonucleic acid (RNA) and fusion proteins according to the invention, the latter being multimerized in a manner that enables their assembly along the strand of RNA to form a rod-shaped structure. The cellular RNA is especially RNA present in cytoplasm of cells where the RNPs are formed. Thus, the conformation of this quaternary structure is different from the one of the non-segmented negative-strand RNA virus of the Paramyxoviridae family, where RNPs result from auto-assembly of N and P proteins with the replicating MV-RNA as nucleocapsids.

The RNPs of the invention adopt a rod-shaped structure as previously described by Spehner et al. (*J. Virol.* 1991, 65(11): 6296-6300) or Bakker et al. (*J. Gen. Virol.*, 2013, 94: 1734-1738). Preferably, the multimeric RNPs according to the invention, in particular those adopting a rod-shaped structure, have a herringbone shape with a diameter of at least 20 nm and a rod length of at least 100 nm. Once charged with heterologous polypeptides, the RNPs of the invention are stable and maintain their structures exposing the heterologous polypeptides on their surface. In multimeric RNPs, the heterologous polypeptides are all of the same nature, in particular they are all identical as far as their content in amino acid residues and sequence length is concerned. Within the frame of the invention, RNPs may have different compositions in the multimer, as far as the number of fusion protein and/or length and/or nucleotide composition of the encapsidated RNA is concerned.

Surprisingly, in the present invention, it was demonstrated for the first time that RNPs formed with the N protein of MV virus are capable to deliver heterologous polypeptides on their surface.

It has been disclosed that even in the absence of viral RNA, the MV N protein auto-assembles into RNPs by interacting with cellular RNA present in various cells where it is expressed (Spehner D et al. 1991 *J. Virol* 65(11), 6296-6300; Bourhis J M, Canard B, Longhi S, 2006, *Virology* 344: 94-110; Warnes A et al., 1995, *Gene* 160: 173-178; Slibinskas R et al., 2004, *J Biotechnol* 107: 115-124). One N molecule wraps or interacts with exactly 6 RNA nucleotides, which has been proposed as an explanation for the so-called "rule of six" known to be necessary to allow efficient replication of MV is maintained. The interactions between the N and the nucleotides of the RNA molecule involve the core portion of the protein, constituted by the N-terminal 400 amino acid residues of the protein (out of total 525 amino acid residues). In measles virus, a regulatory mechanism is necessary to prevent the illegitimate self-assembly of the N in the absence of ongoing viral genomic RNA synthesis. This role is played by the viral phosphoprotein (P), whose association with N prevents illegitimate self-assembly of this latter, and also retains the N soluble form in the cytoplasm. Hence, in the absence of expression of viral phosphoprotein, as it is the case in the expression system of the present invention, the N protein is free to associate with cellular RNA molecules of different lengths.

Accordingly, provided the multimeric RNPs have fusion proteins as disclosed herein which are all or substantially all formed with a N protein and a heterologous polypeptide as defined herein, multimeric RNPs may differ from one another in their number of fusion proteins and size and/or composition of RNA molecule.

As defined herein, the terms "fusion protein" refer to the fusion of the nucleoprotein (N) as defined herein, in particular a nucleoprotein of a non-segmented negative-strand RNA virus of the Paramyxoviridae family, preferably a measles virus, with a heterologous polypeptide as defined herein. This fusion does not impair the stability of the multimeric RNPs of the invention. A fusion protein of the invention is obtained by expression in a host cell, in particular a yeast, of a recombinant polynucleotide encoding the N protein and the heterologous polypeptide, these coding sequences being optionally fused in the polynucleotide having recourse to a third sequence acting as a linker between the N protein and the heterologous polypeptide when translated. According to the invention, the terms "fusion protein" thus encompass glycosylated proteins as a result of glycosylation performed by the yeast expressing them.

As defined herein, the terms "cellular ribonucleic acid" refer to RNA present in the yeast cells, in particular yeast RNA present in the cytoplasm of cells. In particular, this RNA is transcribed from the genome of the cell, i.e. is cellular RNA. In a particular embodiment, the RNA can be a specific RNA which encodes the fusion protein and optionally comprises Leader and/or Trailer sequences as defined hereafter.

As defined herein, the expression "heterologous polypeptide" means that the polypeptide is not a protein or an antigen naturally expressed by a virus of the Paramyxoviridae family but is instead characteristic from another pathogenic organism such as a parasite or another virus. This polypeptide bears epitope(s), B and/or T epitopes, and when expressed on RNPs of the invention induces an immune response in a host, especially in a human, and enables protection against outcomes of infection by said pathogen in particular against outcomes of infection by said parasite or virus. The polypeptide bearing epitope(s) may in particular be an antigen, i.e. a polypeptide recognized by the immune system of a host.

As defined herein, the terms "Paramyxoviridae family" encompass the Paramyxovirinae subfamily, in particular the *Morbillivirus* genus.

According to a particular embodiment of the invention to prepare RNPs according to the invention, the non-segmented negative-strand RNA virus of the Paramyxoviridae family is selected among a measles virus, Rinderpest virus (RPV), the Peste des Petits Ruminants Virus (PPRV), the Canine Distemper Virus (CDV), Dolphin *Morbillivirus* (DMV) and Feline *Morbillivirus*. Preferably, the non-segmented negative-strand RNA virus of the Paramyxoviridae family is a measles virus. More preferably, the measles virus is derived from a live-attenuated measles virus strain. Preferred live-attenuated measles virus strains are the Schwarz, Moraten, Rubeovax, AIK-C, Zagreb and Edmonston strains. The most preferred live-attenuated measles virus strains are the Schwarz strain and the Moraten strain.

In the present invention, the term "measles virus" is abbreviated "MV".

As defined herein, the expression "measles virus derived from a live-attenuated measles virus strain" designates a measles virus originating from a strain that is avirulent or less virulent than a determined parent strain in the same host, especially in human, while maintaining infectious properties and immunogenicity and possibly adjuvancy when administered in a host, especially in human.

Particular nucleoproteins suitable to prepare the fusion protein and RNPs of the invention are nucleoproteins of measles viruses. For illustration, the nucleoprotein may be that of Schwarz/Moraten MV or a variant thereof especially one having amino acid substitutions such as those found in different MV strains and disclosed in Parks et al. (Journal of Virology, 2001, 75(2), 910-920).

The native and optimized nucleotide sequences of the polynucleotide encoding the nucleoprotein of Schwarz/Moraten MV as well as the amino acid sequence of the nucleoprotein of Schwarz/Moraten MV of the invention are the sequences disclosed as SEQ ID No: 1, SEQ ID No: 2 and SEQ ID No: 3 respectively.

The native and optimized nucleotide sequences of the polynucleotide encoding the nucleoprotein of Rubeovax MV as well as the amino acid sequence of the nucleoprotein of Rubeovax MV of the invention are the sequences disclosed as SEQ ID No: 4, SEQ ID No: 5 and SEQ ID No: 6 respectively.

The native and optimized nucleotide sequences of the polynucleotide encoding the nucleoprotein of AIK-C MV as well as the amino acid sequence of the nucleoprotein of AIK-C MV of the invention are the sequences disclosed as SEQ ID No: 7, SEQ ID No: 8 and SEQ ID No: 9 respectively.

The native and optimized nucleotide sequences of the polynucleotide encoding the nucleoprotein of Zagreb MV as well as the amino acid sequence of the nucleoprotein of Zagreb MV of the invention are the sequences disclosed as SEQ ID No: 10, SEQ ID No: 11 and SEQ ID No: 12 respectively.

The native and optimized nucleotide sequences of the polynucleotide encoding the nucleoprotein of Edmonston MV as well as the amino acid sequence of the nucleoprotein of Edmonston MV of the invention are the sequences disclosed as SEQ ID No: 13, SEQ ID No: 11 and SEQ ID No: 12 respectively.

A mutant form of a native protein of the invention is a protein with point mutations, in particular with 1 to 10% of substitutions in amino acid residues or with mutations occurring between nucleoproteins of MV as illustrated herein and found in various MV strains or mutations by deletion of amino acid residues. Mutant forms also include deletion of polypeptide fragments such as fragments spanning from 1 to 125 amino acid residues in the C-terminal part of the nucleoprotein of MV, i.e., fragments in the last 125 amino acid residue chain of this nucleoprotein (amino acids 401-525). It has indeed been observed that interactions between the native nucleoprotein of MV and RNA molecules involve the N-terminal 400 amino acid residues of the native protein.

According to a particular embodiment of the invention, the heterologous polypeptide is from a parasite, preferably from a protozoan parasite of the genus *Plasmodium*, more preferably from *Plasmodium berghei* or *Plasmodium falciparum*, or from a virus, preferably from the Picornaviridae family, more preferably from the genus *Enterovirus*, for example from *Enterovirus* 71 (EV71).

The expression "protozoan parasite of the genus *Plasmodium*" designates every and all forms of the parasite that are associated with the various stages of the life cycle in the mammalian, especially human host, including in particular sporozoites, especially sporozoites present in the body after inoculation, or sporozoites developing in the hepatocytes, merozoites, including especially merozoites produced in the hepatocytes (forms of the pre-erythrocytic stage and including forms of the erythrocytic stage of the cycle such as merozoites contained in red-blood cells of the cycle). These forms of the parasite are characterized by various specific antigens that are well known and identified in the art, and can also be designated by reference to the stage of the infection.

In a particular embodiment of the invention, the heterologous polypeptide is the CS (circumsporozoite) polypeptide, in particular of *P. berghei* or *P. falciparum.*

The native and optimized nucleotide sequences of the polynucleotide encoding the CS polypeptide of *P. berghei* as well as the amino acid sequence of the CS polypeptide of *P. berghei* of the invention are the sequences disclosed as SEQ ID No: 14, SEQ ID No: 15 and SEQ ID No: 16 respectively.

According to a particular embodiment of the invention, the native and optimized nucleotide sequences of the polynucleotide encoding the CS polypeptide of *P. falciparum* as well as the amino acid sequence of the CS polypeptide of *P. falciparum* of the invention are the sequences disclosed as SEQ ID No: 17, SEQ ID No: 18 and SEQ ID No: 19 respectively.

*Enterovirus* is a small, positive-sense single-stranded RNA virus from the *Enterovirus* genus in the family Picornaviridae, which causes a wide range of infections. In particular, *Enterovirus* 71 (EV71), first isolated in 1969, causes hand, foot, and mouth disease (HFMD), mainly in young children, and can be associated with neurological complications. Asian countries have seen large outbreaks of disease, notably in summer 2013.

In a particular embodiment of the invention, the heterologous polypeptide is from the genus *Enterovirus*, preferably from *Enterovirus* 71 (EV71).

In a particular embodiment, the heterologous polypeptide from an *Enterovirus* is VP1 (Viral capsid protein 1) from *Enterovirus* 71.

The native and optimized nucleotide sequences of the polynucleotide encoding the VP1 protein from *Enterovirus* 71 as well as the amino acid sequence of the VP1 protein from *Enterovirus* 71 of the invention are the sequences disclosed as SEQ ID No: 20, SEQ ID No: 21 and SEQ ID No: 22 respectively.

Avidin, a highly glycosylated egg-white protein, is known to have a high affinity for biotin, allowing the formation of a stable avidin-biotin complex. It has found widespread use in protein and nucleic acid detection as well as purification methods.

According to a particular embodiment of the invention, the heterologous polypeptide is avidin or comprises avidin.

The native and optimized nucleotide sequences of the polynucleotide encoding the avidin protein as well as the amino acid sequence of the avidin protein of the invention are the sequences disclosed as SEQ ID No: 23, SEQ ID No: 24 and SEQ ID No: 25 respectively.

According to a particular embodiment of the invention, the heterologous polypeptide is fused to the C-terminus of the nucleoprotein (N) as defined herein (including its variants), in particular is fused to the C-terminus of the nucleoprotein (N) as defined herein (including its variants) through a peptide linker, whose sequence has a size between 5 and 10 amino acid residues. The linker is recognized as a sequence which neither belongs to the native nucleoprotein nor to the heterologous polypeptide. A preferred peptide linker of the invention is composed of 6 or 7 amino acid residues. Preferably, the peptide linker is a small peptide linker, which is composed of amino acid residues having small and non charged side chains such as Alanine and Glycine.

According to another particular embodiment of the invention, the fusion protein of the invention does not comprise a peptide linker.

According to a particular embodiment of the invention, the nucleotide sequence encoding the peptide linker and the amino acid sequence of the peptide linker of the invention are the sequences disclosed as SEQ ID No: 26 and SEQ ID No: 27 respectively. They are in particular used in the N-PbCS, N-VP1 and N-Avidin fusion proteins designed for the preparation of RNPs.

According to another particular embodiment of the invention, the nucleotide sequence encoding the peptide linker and the amino acid sequence of the peptide linker of the invention are the sequences disclosed as SEQ ID No: 28 and SEQ ID No: 29 respectively. They are in particular used in the N-PfCS fusion protein designed for the preparation of RNPs.

According to a particular embodiment of the invention, the native and optimized nucleotide sequences of the polynucleotide encoding the N-PbCS fusion protein as well as the amino acid sequence of the N-PbCS fusion protein are the sequences disclosed as SEQ ID No: 30, SEQ ID No: 31 and SEQ ID No: 32 respectively, wherein the nucleoprotein N is obtained from the Schwarz strain and the fusion protein comprises a peptide linker disclosed as sequence SEQ ID No: 26 or SEQ ID No: 27.

According to a particular embodiment of the invention, the native and optimized nucleotide sequences of the polynucleotide encoding the N-PfCS fusion protein as well as the amino acid sequence of the N-PfCS fusion protein are the sequences disclosed as SEQ ID No: 33, SEQ ID No: 34 and SEQ ID No: 35 respectively, wherein the nucleoprotein N is obtained from the Schwarz strain and the fusion protein comprises a peptide linker disclosed as sequence SEQ ID No: 28 or SEQ ID No: 29.

According to a particular embodiment of the invention, the native and optimized nucleotide sequences of the polynucleotide encoding the N-VP1 fusion protein as well as the amino acid sequence of the N-VP1 fusion protein are the sequences disclosed as SEQ ID No: 36, SEQ ID No: 37 and SEQ ID No: 38 respectively, wherein the nucleoprotein N is obtained from the Schwarz strain and the fusion protein comprises a peptide linker disclosed as sequence SEQ ID No: 26 or SEQ ID No: 27.

According to a particular embodiment of the invention, the native and optimized nucleotide sequences of the polynucleotide encoding the N-Avidin fusion protein as well as the amino acid sequence of the N-Avidin fusion protein are the sequences disclosed as SEQ ID No: 39, SEQ ID No: 40 and SEQ ID No: 41 respectively, wherein the nucleoprotein N is obtained from the Schwarz strain and the fusion protein comprises a peptide linker disclosed as sequence SEQ ID No: 26 or SEQ ID No: 27.

The multimeric RNPs according to the invention are high-molecular weight RNPs, assembling from 200 to 1000 fusion proteins obtained between a nucleoprotein (N) and a heterologous polypeptide, preferably from 300 to 700 of said fusion proteins, in particular from 500 to 700 of said fusion proteins. The molecular weight of these RNPs is comprised between 10,000 and 100,000 kDa. In this structure, the N proteins are fused to the heterologous polypeptides and also interact with RNA molecules of the cell in which they are expressed in such a way that the heterologous polypeptide elicits the immune system of a host to whom it is administered.

The present invention also relates to a polynucleotide encoding the fusion protein according to the invention, in particular a polynucleotide comprising (i) the nucleotide sequence encoding the nucleoprotein (N) selected in the group of SEQ ID No: 2, SEQ ID No: 5, SEQ ID No: 8 and SEQ ID No: 11, optionally fused with (ii) a nucleotide sequence encoding the peptide linker selected in the group of SEQ ID No: 26 and SEQ ID No: 28, and (iii) the nucleotide sequence encoding the heterologous polypeptide fused to the nucleotide sequence of (i) or, if any, to the nucleotide sequence of (ii).

The term "encoding" used in the present application defines the ability of the nucleic acid molecules to be transcribed and where appropriate translated for product expression into selected cells or cell lines, when said molecule is placed under expression control sequences including promoter for transcription.

According to the invention, the polynucleotide encoding the N protein and the polynucleotide encoding the heterologous polypeptide are advantageously optimized for expression in yeast, and the initiating ATG codon of N is put in a modified Kozak consensus sequence for proper translation initiation of the polygene in yeast (aaaaaaATGGCC) (Kozak M 1987, *NAR* 15: 8125-8148; Kozak M 1990, *PNAS* 87: 8301-8305, which discloses aAaAaAATGca).

In a particular embodiment of the invention, the polynucleotide comprising the nucleotide sequence encoding the nucleoprotein (N) has an optimized sequence for expression in yeast. A particular embodiment of this polynucleotide is selected in the group of SEQ ID No: 2, SEQ ID No: 5, SEQ ID No: 8 and SEQ ID No: 11.

In a particular embodiment of the invention, codon optimization is carried out on the polynucleotide encoding the nucleoprotein (N) and on the polynucleotide encoding the heterologous polypeptide of the fusion protein.

In a particular embodiment codon optimization is carried out to delete the cleavage site(s) available for the proteases of the yeast selected for the expression of the ribonucleoprotein of the invention. As a result, expression of fusion proteins and RNP containing the same, from codon optimized sequences may enable the expression of a higher amount of the full-length fusion protein in said selected yeast and accordingly may favourably influence the immunogenic properties of the thus obtained RNPs. Specific sites for yeast protease cleavage in a determined polynucleotide encoding the fusion protein may be determined experimentally by assessment of the digestion profile of the fusion protein expressed from the yeast cells. Experimental protocols to map cleavage sites in a polynucleotide expressing the fusion protein according to the invention are disclosed especially in example 4.

In a particular embodiment of the invention, the polynucleotide encoding the nucleoprotein (N) and the polynucleotide encoding the heterologous polypeptide are inserted between a Leader and/or a Trailer sequence from a non-segmented negative-strand RNA virus of the Paramyxoviridae family. These viral sequences contain the encapsidation signals that allow RNA assembly with the nucleoprotein (N) (Longhi S. *Current topics in microbiology and immunology* 2009; 329:103-28). Cloned upstream and downstream of the polynucleotide encoding the nucleoprotein (N) and the heterologous polypeptide, the Leader and Trailer sequences make possible the encapsidation of these RNA molecules into the RNPs. The Leader and Trailer sequences of a non-segmented negative-strand RNA virus of the Paramyxoviridae family have been described in the international patent application WO2009/095791. The Leader sequence can comprise one viral promoter of a non-segmented negative-strand RNA virus of the Paramyxoviridae family, and the Trailer sequence can comprise a terminator sequence of the transcription. As an example, the MV Schwarz Leader sequence (comprising a N start codon) cloned upstream from the coding sequence of the nucleoprotein (N) and the MV Schwarz Trailer sequence cloned downstream from the coding sequence of the heterologous polypeptide are disclosed as the sequences SEQ ID No: 42 and SEQ ID No: 43 respectively.

In a particular embodiment of the invention, the polynucleotide encoding the fusion protein according to the invention further comprises a Leader sequence and/or a Trailer sequence, for example a Leader sequence cloned upstream from the coding sequence of the nucleoprotein (N), as disclosed in SEQ ID No: 42 and/or a Trailer sequence cloned downstream from the coding sequence of the heterologous polypeptide as disclosed in SEQ ID No: 43.

In an aspect of the invention, the polynucleotide has a nucleic acid sequence formed of the nucleotide sequence encoding a N protein of a MV virus, in particular of a Schwarz/Moraten strain fused, in its ends corresponding to the C-terminal end of the N protein or of a variant as defined herein, with a sequence encoding a peptide linker.

In a particular embodiment of the invention, the polynucleotide comprising the nucleotide sequence encoding the heterologous polypeptide is optimized for expression in yeast. A particular embodiment of this polynucleotide is selected in the group of SEQ ID No: 15, SEQ ID No: 18, SEQ ID No: 21 and SEQ ID No: 24.

In a particular embodiment of the invention, the polynucleotide comprising the nucleotide sequence encoding the fusion protein is optimized for expression in yeast. A particular embodiment of this polynucleotide is selected in the group of SEQ ID No: 31, SEQ ID No: 34 and SEQ ID No: 37.

The present invention also relates to an isolated or purified polynucleotide encoding a fusion protein as defined herein. In particular, the present invention relates to an isolated or purified polynucleotide encoding a fusion protein as defined herein and comprising the nucleotide sequence selected in the group of SEQ ID No: 31, SEQ ID No: 34 and SEQ ID No: 37.

The present invention also relates to an isolated or purified fusion protein encoded by a polynucleotide herein disclosed. In particular, the present invention relates to an isolated or purified fusion protein encoded by a polynucleotide herein disclosed and comprising the amino acid sequence selected in the group of SEQ ID No: 32, SEQ ID No: 35 and SEQ ID No: 38.

According to a particular embodiment of the invention, the polynucleotide encoding the fusion protein of RNPs, in particular the polynucleotide having one of the sequences illustrated herein, is under the control of an inducible promoter suitable for yeast expression. Methanol-inducible AOX1 promoter is an example of such control sequence.

The present invention also relates an expression vector, in particular a plasmid bearing the polynucleotide of the invention, which is illustrated in the examples.

The present invention also relates to recombinant yeast, which is recombined with a polynucleotide of the invention, in conditions enabling constitutive or transitory or inducible expression of multimeric RNPs of the invention. The present invention also relates to recombinant yeast, which is recombined with a polynucleotide of the invention, especially by transfection with a plasmid comprising said polynucleotide. Said transfection is advantageously stable.

The present invention also relates to recombinant yeast, which expresses multimeric RNPs of the invention.

The present invention also relates to recombinant yeast, which is recombined, especially transfected with a polynucleotide of the invention and expresses multimeric RNPs of the invention.

Cells of said recombinant yeasts are either suitable for use in the embodiments of the invention either as live-cells or as inactivated, in particular heat-inactivated yeast cells. In such a case, the yeast cells may be designated as whole recombinant yeasts.

According to a particular embodiment of the invention, the recombinant yeast of the invention is prepared from a strain of *P. pastoris* or *S. cerevisiae*. In particular, the strain of *P. pastoris* is the SMD1168 strain or the GS115 strain or the KM71 strain or any other *P. pastoris* strain that are known to the person skilled in the art (Lin-Cereghino J. et al., *Methods Mol. Biol.*, 2007, 389, 11-25). *P. pastoris* strains are commercially available (Invitrogen, GeneScript™)

The present invention also relates to an inactivated recombinant yeast, which results from heat-inactivation at 58-60° C. for 45-60 minutes, preferably at 60° C. for 45 minutes of a recombinant yeast as defined herein.

The present invention also relates to a yeast lysate, which is a lysate of the recombinant yeast according to the invention.

As defined herein, the terms "yeast lysate" encompass whole or fractions of the yeast lysate, such as mechanically disrupted yeast cells submitted to mild centrifugation to eliminate nuclei and most cell membranes.

The present invention also relates to an immunogenic composition comprising multimeric RNPs or recombinant yeast or yeast lysate according to the invention.

In a particular embodiment, the immunogenic composition does not comprise an accessory adjuvant.

As defined herein, the terms "accessory adjuvant" encompass any molecules such as oils, aluminium salts and virosomes that enhance the immune response of a vaccine. Examples of accessory adjuvants are well known to a person skilled in the art.

The present invention also relates to a subunit vaccine platform comprising multimeric RNPs or recombinant yeast or yeast lysate according to the invention. In the present invention, two delivery systems (yeast and MV RNPs) are combined.

The present invention also relates to a multivalent vaccine comprising a mixture of recombinant yeasts or a mixture of yeast lysates according to the invention, wherein in the mixture, at least two clones of recombinant yeasts or yeast lysates are present, one clone expressing a heterologous polypeptide as defined herein different from the heterologous polypeptide of the other(s) clone(s).

The present invention also relates to a multivalent immunogenic composition comprising a mixture of recombinant yeasts or a mixture of yeast lysates according to the invention, wherein in the mixture, at least two clones of recombinant yeasts or yeast lysates are present, one clone expressing a heterologous polypeptide as defined herein different from the heterologous polypeptide of the other(s) clone(s). In particular, the mixture comprises yeasts expressing different RNPs, i.e. yeasts distinguishing from one another by the heterologous polypeptide expressed by their RNPs, or lysates of such yeasts. In this case, the different recombinant yeasts or yeast lysates, each expressing a polypeptide of interest, are mixed in a single vaccine.

The present invention also relates to a process for the preparation of multimeric RNPs of the invention characterized in that it comprises the steps of:

(i) obtaining recombinant yeast or yeast lysate according to the invention, and (ii) recovering the multimeric RNPs from said yeast or yeast lysate.

The present invention also relates to a process for the preparation of recombinant yeasts or yeast lysates according to the invention comprising:

(i) recombining a yeast with a polynucleotide according to the invention, (ii) culturing said yeast in a medium, (iii) expressing the fusion protein in said yeast, in particular upon induction of the promoter controlling expression of the polynucleotide, e.g. by methanol induction, (iv) optionally, heat-inactivating said yeast at 58-60° C. for 45-60 minutes, preferably at 60° C. for 45 minutes, and (v) optionally, preparing a yeast lysate.

The present invention also relates to the use of recombinant yeasts or yeast lysates according to the invention for the in vitro production of a vaccine.

The present invention also relates to the use of recombinant yeasts or yeast lysates according to the invention for the in vitro production of an immunogenic composition.

The present invention also relates to the use of recombinant yeasts or yeast lysates according to the invention for expression and vector systems for delivery to a host.

The present invention also relates to the use of multimeric RNPs according to the invention as active ingredient for the in vitro production of a vaccine.

The present invention also relates to the use of multimeric RNPs according to the invention as active ingredient for the in vitro production of an immunogenic composition.

The present invention also relates to multimeric RNPs or recombinant yeasts or yeast lysates according to the invention for use in eliciting a protective prophylactic or a therapeutic immune response against the heterologous polypeptide in a host in need thereof. In particular the immune response is intended for protection against malaria or is intended for protection against *Enterovirus* infection depending on the heterologous polypeptide expressed on RNPs.

According to another particular embodiment, a vaccine comprising the recombinant yeasts or the yeast lysates according to the invention induces the production of antibodies, especially of antibodies directed against the heterologous polypeptide of the RNPs.

According to another particular embodiment, a vaccine comprising the recombinant yeasts or the yeast lysates according to the invention induces both Th1 and Th2 immune responses.

In a particular embodiment of the invention, the administration of the recombinant yeasts, recombinant yeast lysates or multimeric RNPs is carried out in a prime boost regimen.

It is considered that the composition of the invention (in particular the RNPs, recombinant yeast or yeast lysate as defined herein) has a protective capacity when after challenge of immunized host with the parasite of other infectious agent, it enables the delay and/or the attenuation of the symptoms usually elicited after infection with said parasite or infectious agent against which protection is sought by the administration of the composition of the invention, or when especially the parasitemia is delayed.

Other features and advantages of the invention will be apparent from the examples which follow and will also be illustrated in the figures.

(A)—30 YU N-PbCS, N or WT yeast lysates tree times bi-weekly
(B)—30 YU N-PbCS, N or WT yeast lysates five times weekly
(C)—150 YU N-PbCS, N or WT yeast lysates five times weekly
(D)—300 YU N-PbCS, N or WT yeast lysates five times weekly Bars correspond to medians. Asterisks (*) indicate significant median differences (one symbol for $p<0.05$ and two for $p<0.005$; Mann-Whitney nonparametric test).

Figure 9:
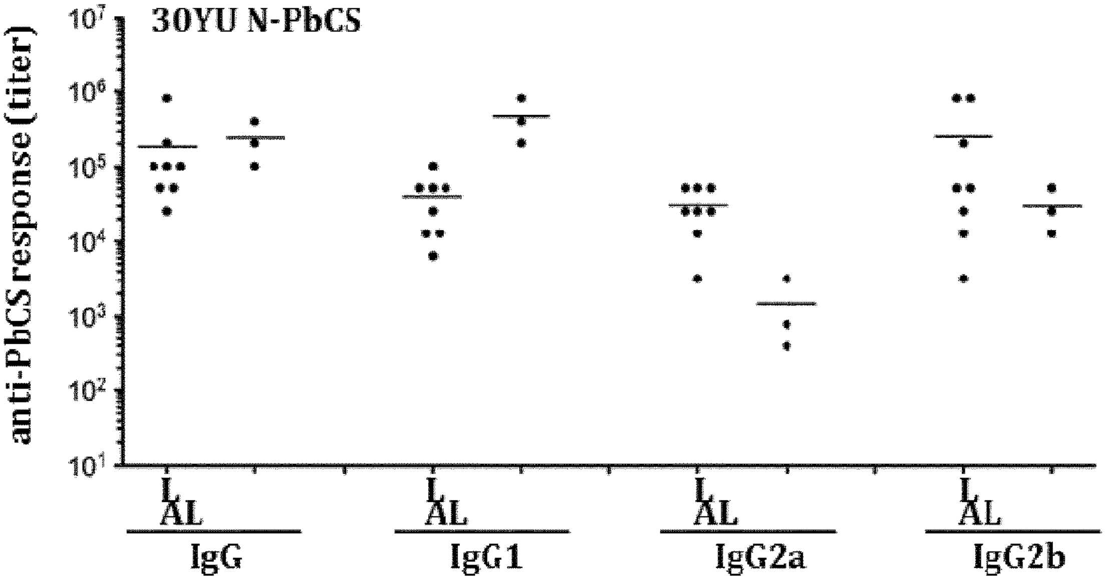

FIG. 9. Isotyping of humoral IgG responses at day 42 mice immunized with 30 YU N-PbCS yeast. L—non-adjuvanted lysate formulation administered five times weekly, AL—alum-adjuvanted lysate formulation administered three times bi-weekly. Bars correspond to median values per group.

Figure 10:
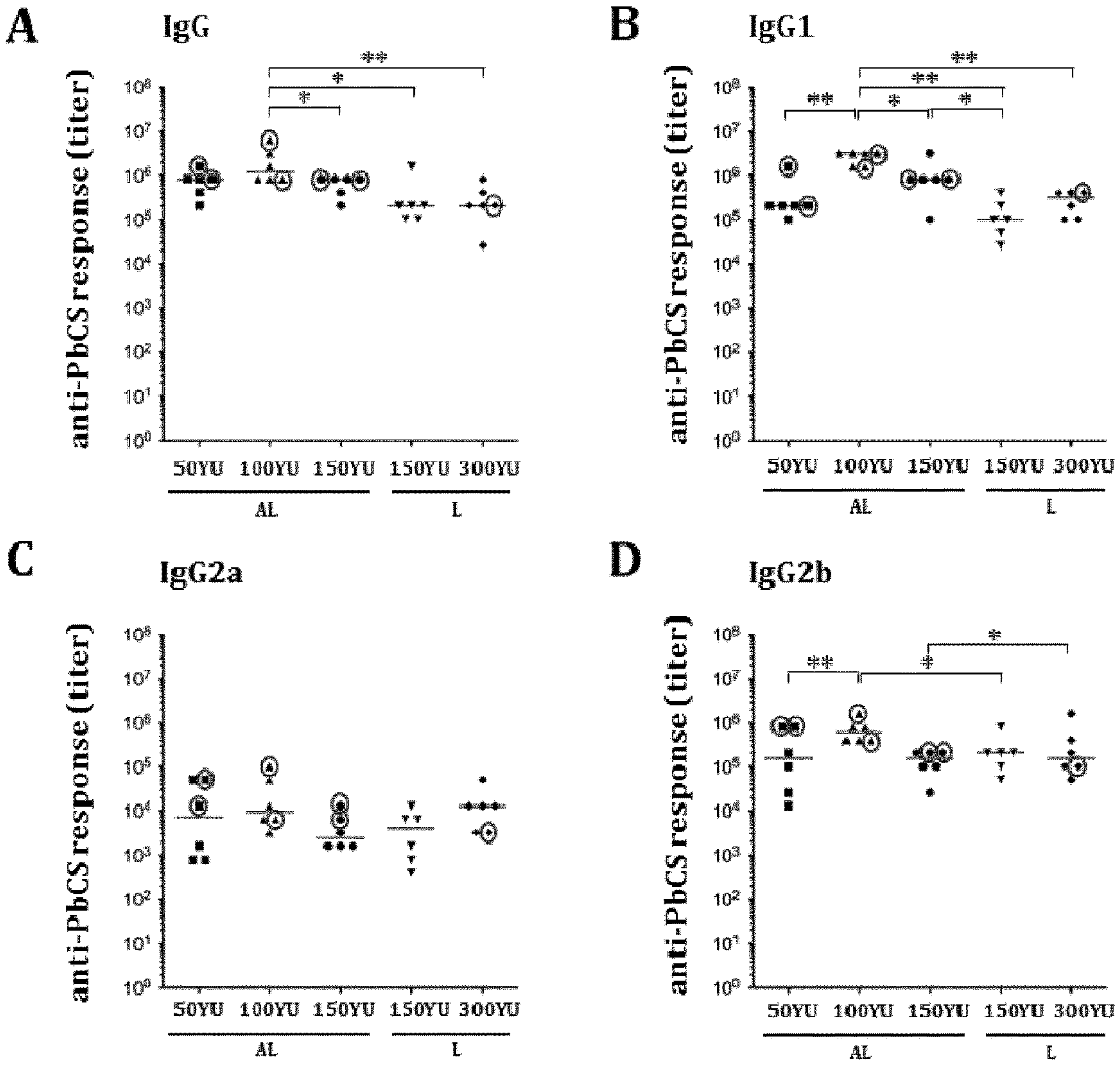

FIG. 10. Immunogenicity of N-PbCS adjuvanted and non adjuvanted yeast lysates. Isotyping of humoral IgG responses at day 42: (A) IgG, (B) IgG1, (C) IgG2a and (D) IgG2b. Bars correspond to median values per group. Antibody titers of the non-parasitized mice are encircled. Asterisks (*) indicate significant median differences (one symbol for $p<0.05$ and two for $p<0.005$; Mann-Whitney nonparametric test).

Figure 11:
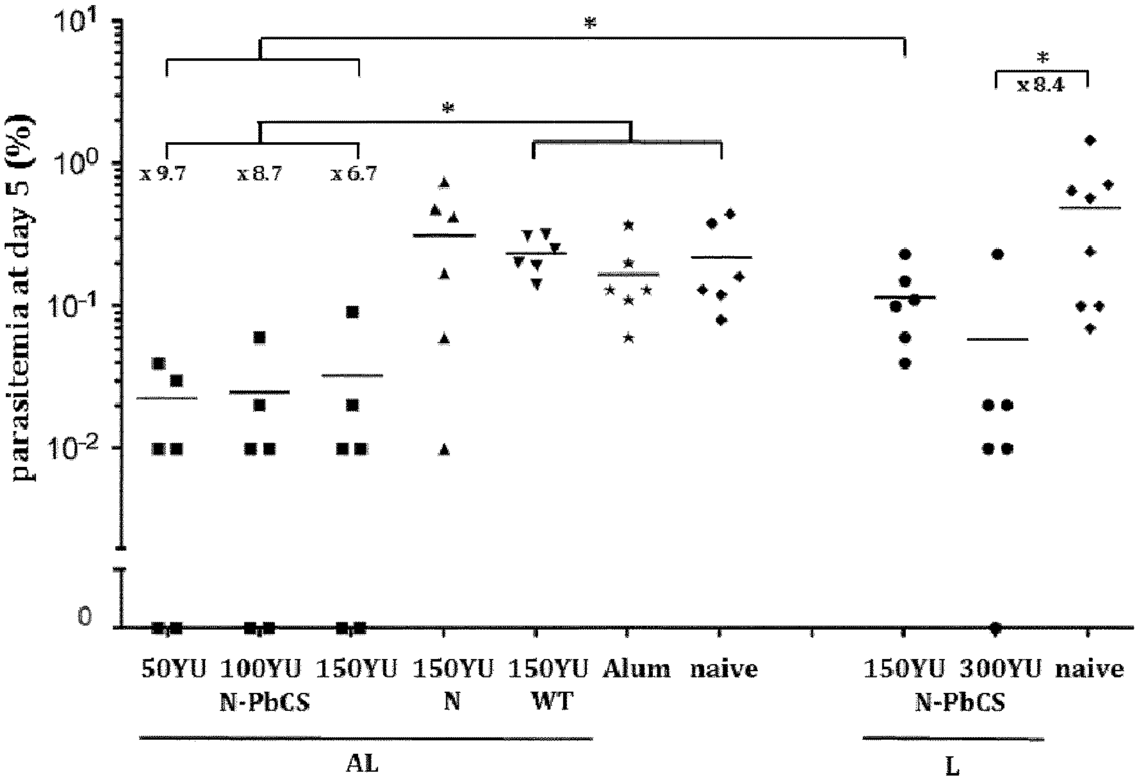

FIG. 11. Comparison in parasitemia at day 5 post-challenge. L—non-adjuvanted yeast lysate (experiment 3), AL—alum-adjuvanted yeast lysate (experiment 4). Alum—group of mice immunized with alum only. Bars correspond to means among parasitized mice in the group. Bars correspond to medians. Asterisk (*) indicates significant median differences ($p<0.05$, Mann-Whitney nonparametric test). Non-parasitized mice were excluded from calculation. Decrease in parasitemia in immunized groups in comparison with the respective naive group from the same experiment is indicated in folds.

Figure 12:
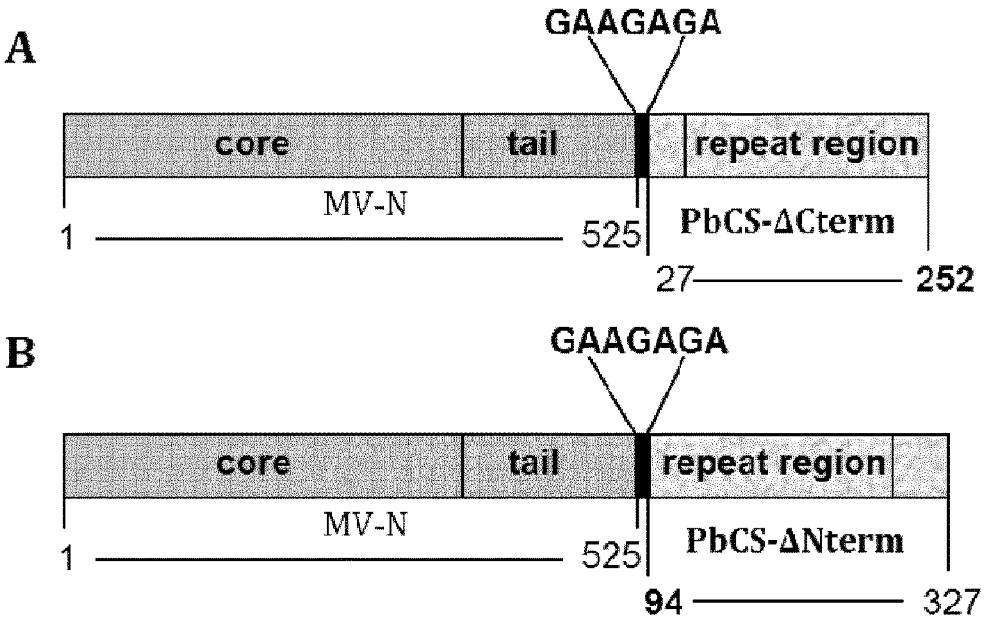

FIG. 12. Schematic representation of N-PbCS protein truncated at the C-terminal (A) or N-terminal (B) ends of PbCS. MV-N—dark grey, PbCS—light grey. Amino acids numbering are given according to N from the MV Schwarz vaccine strain and PbCS from the Pb ANKA strain. The peptide linker "GAAGAGA" has the amino acid sequence of SEQ ID NO: 27.

Figure 13:
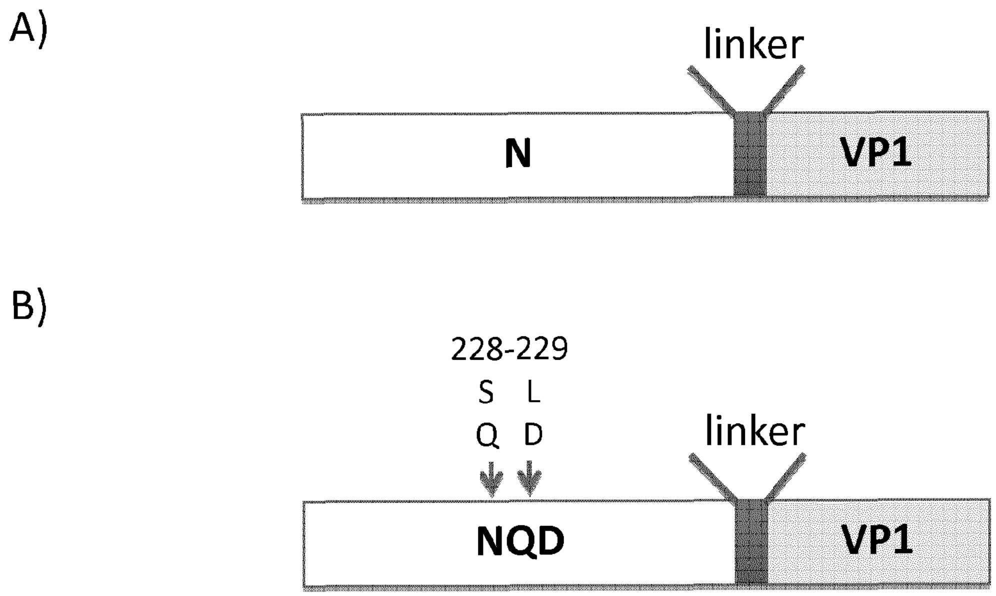

FIG. 13. Schematic representation of the N-VP1 fusion protein (A) and of the NQD-VP1 fusion protein (B). NQD mutant is described in Karlin et al, *Virology* 302, 420-432 (2002). Mutations and their amino acids positions are given.

FIG. 14. Characterization of *P. pastoris* GS115 yeast expression N-VP1. ELISA quantification of N and VP1 proteins in ultracentrifugation fractions and pellets of GS115 lysates expressing N-VP1 (A) or NQD-VP1 (B) (normalized mean values from duplicates of ultracentrifugation tubes). Grey zone indicates the Mix sample pooled for electron microscopy analysis (fractions 18-26 of each tube). Values correspond to optical densities at $OD_{450\ nm/620\ nm}$. SB: suspension buffer. Electron microscopy analysis of yeast lysates from GS115 expressing N (C) or N-VP1 (D). N-VP1 sample corresponds to the pooled Mix (S1 and S2 duplicates) from panel A. Black arrows highlight RNP rod structures.

Figure 15:
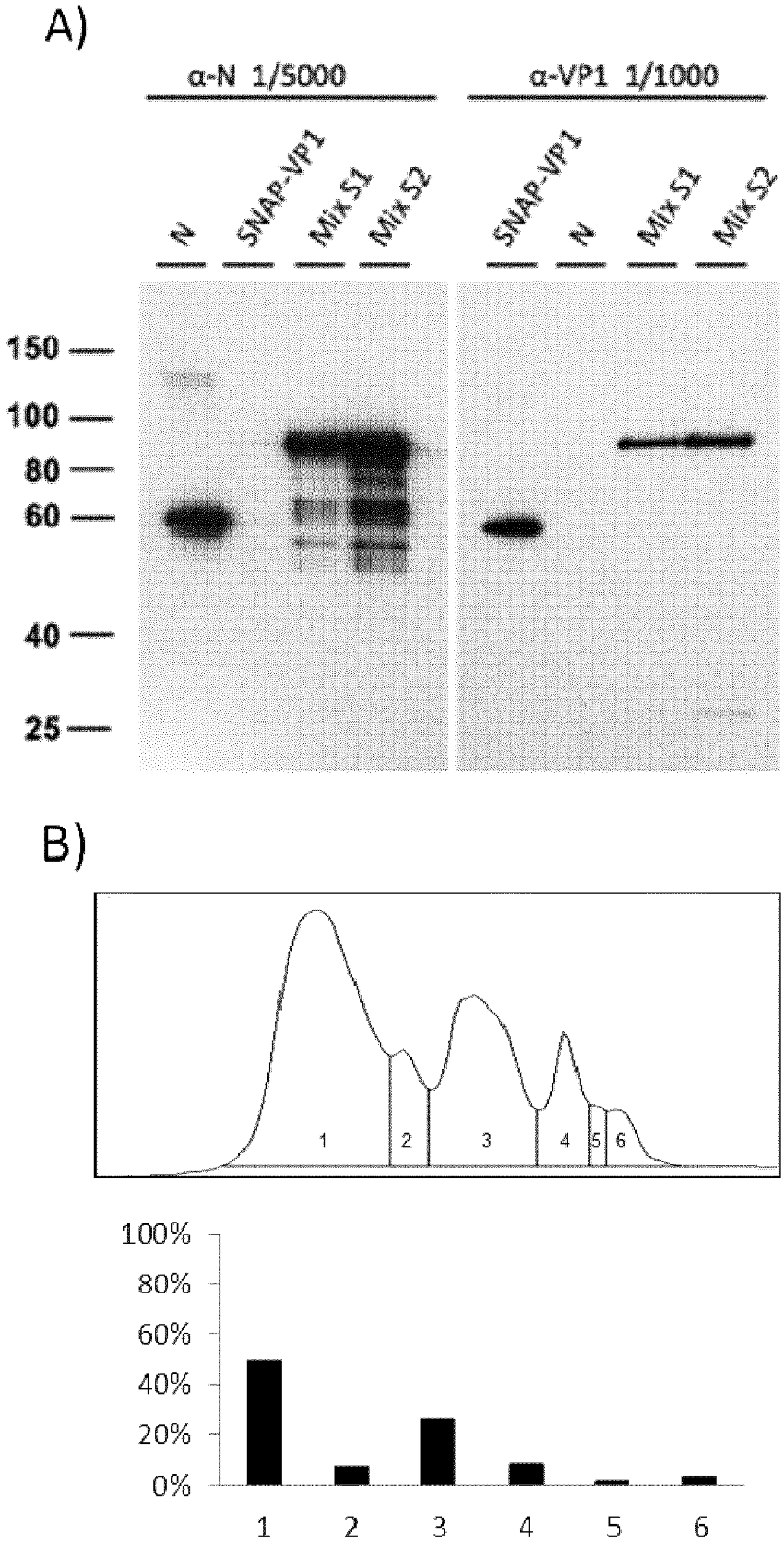

FIG. 15. Characterization of *P. pastoris* GS115 N-VP1 yeast lysate MIX sample. (A)—Western blot analysis of pooled Mix sample obtained following GS115 N-VP1 yeast lysate ultracentrifugation (S1 and S2 represent fractions 18-26 from two independent ultracentrifugation tubes). N—purified recombinant N protein. SNAP-VP1—purified recombinant SNAP-tagged VP1 protein. (B)—Graphic representation (top panel) of mean intensity of N-VP1 bands (MixS1 and MixS2) detected by anti-N antibody from panel A. The histogram shows area of each peak with respect to total area of the plot (in percentage) representative of global band intensity.

Figure 16:
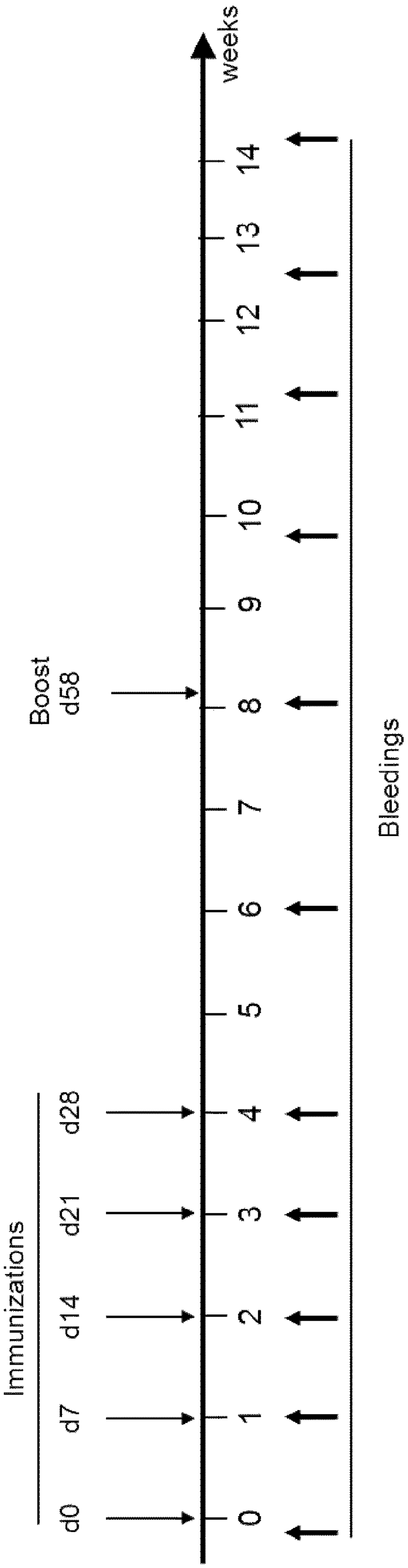

FIG. 16. Schematic representation of the immunization protocol. Immunization schedule is given in days (d) and bleeding time points in weeks. Immunization protocol A corresponded to weekly immunizations (d0, d7, d14, d21 and d28), while protocol B to bi-weekly immunizations (d0, d14 and d28). Boosting doses were administered at d58.

Figure 17:
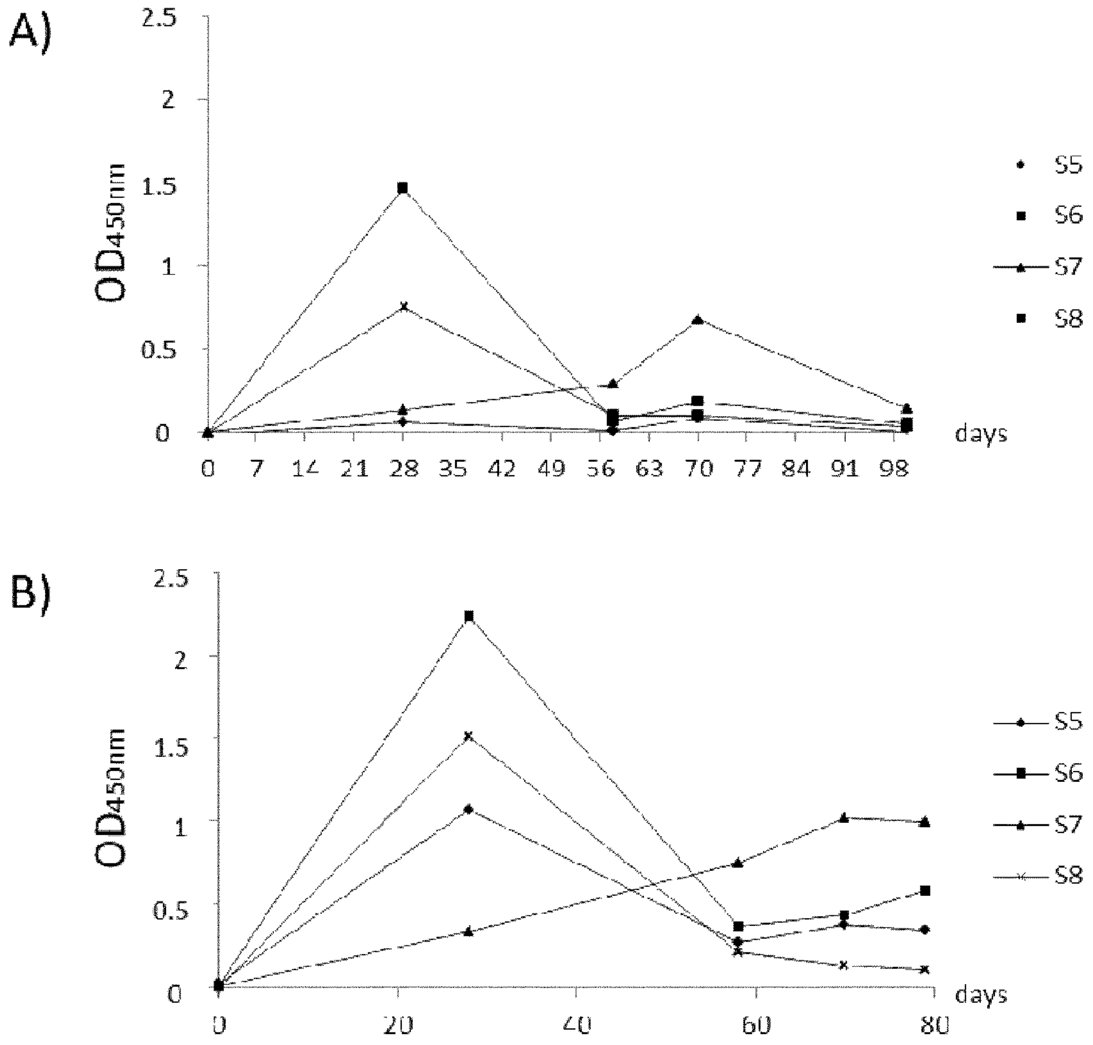

FIG. 17. ELISA analysis of anti-VP1 antibody responses in C57Bl/6 mice. Mice were immunized subcutaneously with 30 YU of *P. pastoris* expressing N-VP1 and following protocol B. S5, S6, S7 and S8 are independent mice. Data correspond to 1/100 diluted mouse sera and are given in panel (A). Panel (B) details data given in panel (A) for the first 80 days of follow up. OD: optical density at 450 nm (reference wavelength: 600 nm).

Figure 18:
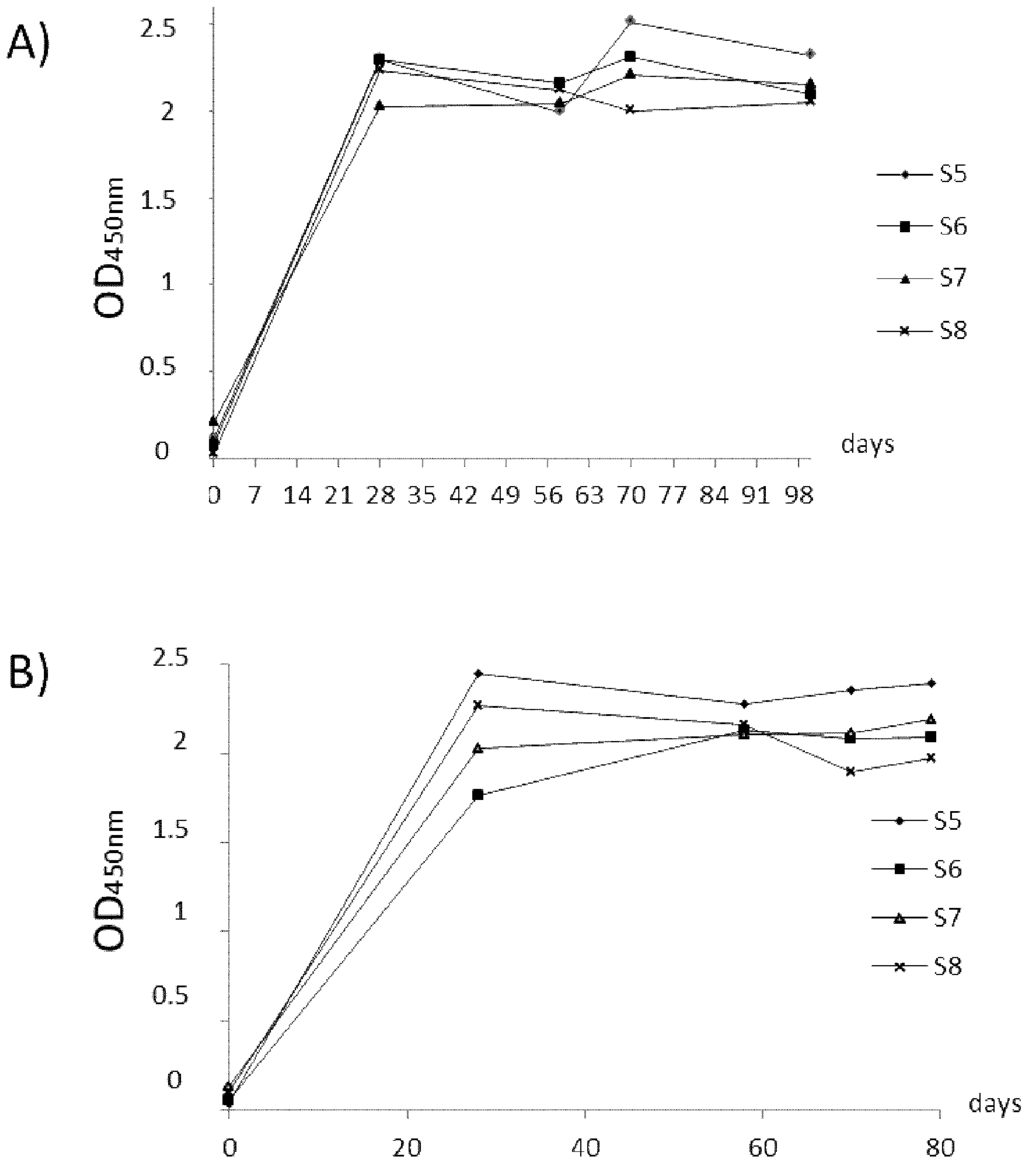

FIG. 18. ELISA analysis of anti-N antibody responses in C57Bl/6 mice. Mice were immunized subcutaneously with 30 YU of *P. pastoris* expressing N-VP1 and following protocol B. S5, S6, S7 and S8 are independent mice. Data correspond to 1/100 diluted mouse sera and are given in panel (A). Panel (B) details data given in panel (A) for the first 80 days of follow up. OD: optical density at 450 nm (reference wavelength: 600 nm).

Figure 19:
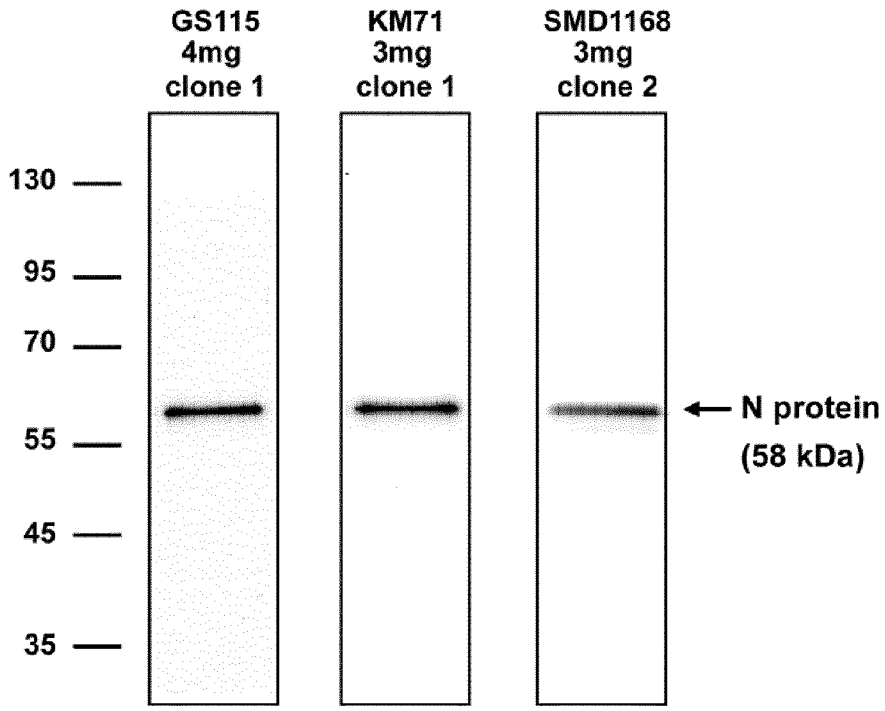

FIG. 19. Expression of N protein in GS115, KM71 and SMD1168 *P. pastoris* strains. Concentrations of Geneticin in selection plates for the specific clones, and clone numbers, are indicated. Yeast lysates were diluted 1/600 before loading on western blot.

Figure 20:
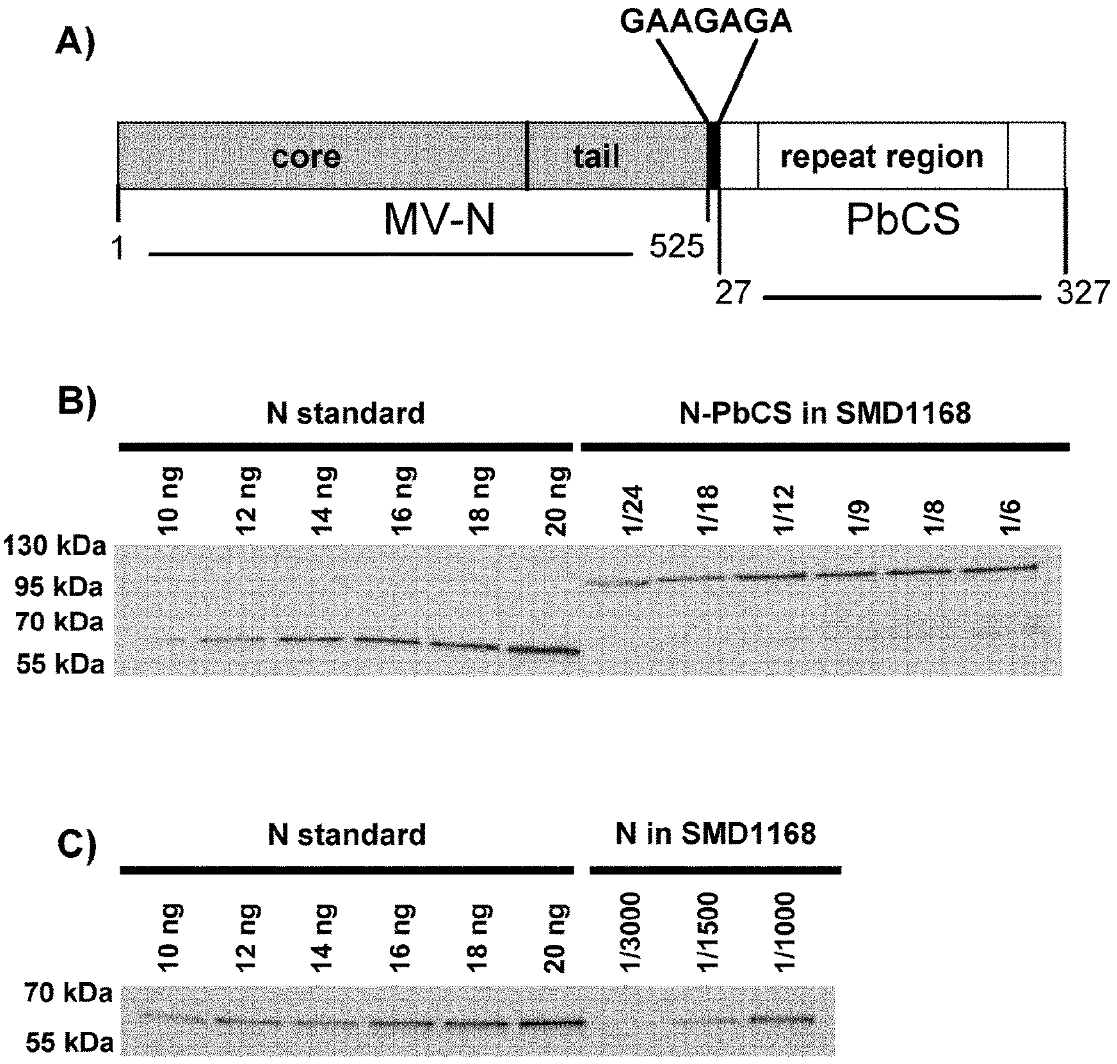

FIG. 20. Expression of N-PbCS in *P. pastoris*. (A) Schematic representation of N-PbCS fusion protein. MV-N (grey) is composed of a core domain in N-terminal and an unstructured tail domain in C-terminal (Longhi S, 2012, *Adv Exp Med Biol* 725: 126-141). The GAAGAGA linker is in black. PbCS (white) corresponds to the central repeat region flanked by major portions of the N-terminal and C-terminal domains of the protein (Plassmeyer M L et al., 2009, *J Biol Chem* 284: 26951-26963). Amino acids numbering are given according to N from the MV Schwarz vaccine strain and PbCS from the Pb ANKA strain (sequence details in FIG. 21). (B) Quantitative western blot analysis of SMD1168 expressing N-PbCS or (C) N. In (B) and (C), yeast lysates were diluted as indicated, the MV-N protein was used as a standard with increasing concentrations and western blots were probed with an anti-N antibody.

FIG. 21. Optimized nucleotide sequence of the N (SEQ ID No: 2) (A) and PbCS (SEQ ID No: 15) (B) proteins for expression in GS115, KM71 and SMD1168 *P. pastoris* strains. The nucleotide sequence of the linker between N and PbCS (SEQ ID No: 26) is given in bold in the box (B); (C) Kyte-Doolitle hydropathy profile (DNA Strider1.4f18) of N-PbCS: negative values correspond to hydrophilic amino acid motifs.

Figure 22:
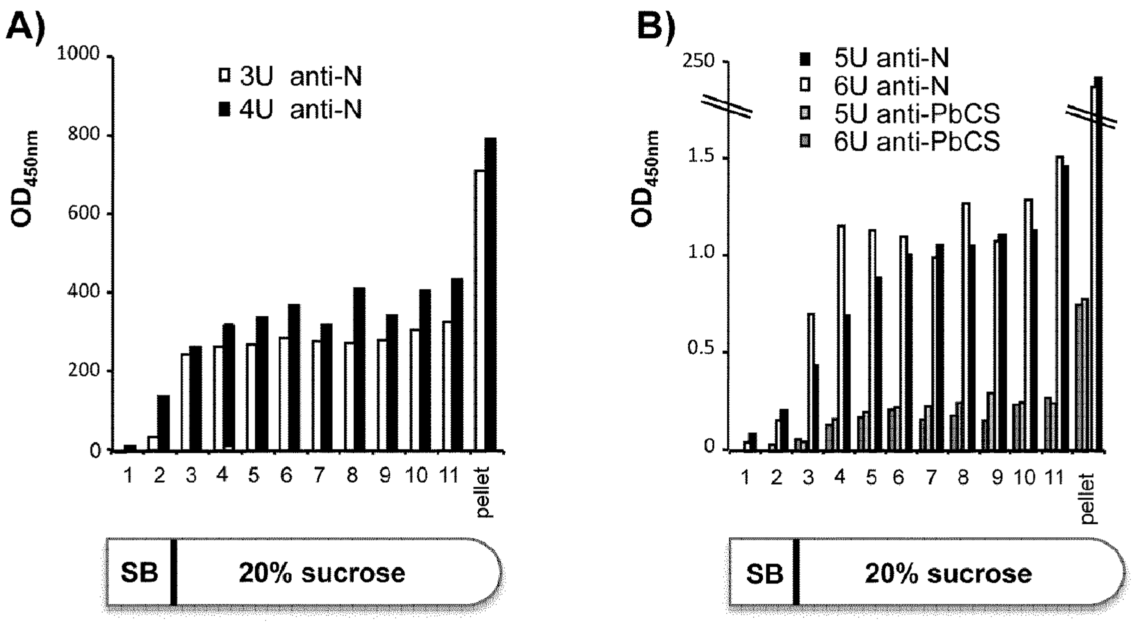

FIG. 22. ELISA quantification of N or PbCS proteins in ultracentrifugation (U) fractions and pellets of SMD1168 lysates expressing N alone at 871 ng/YU (A) or N-PbCS at 12 ng/YU (B). Yeast cultures, lysates and ultracentrifugations were performed in duplicate (3U and 4U for N expressing yeast, and 5U and 6U for N-PbCS yeast). Values correspond to optical densities at $OD_{460\ nm}$ (taking $OD_{620\ nm}$ as reference) multiplied by sample dilutions. SB: suspension buffer.

Figure 23:
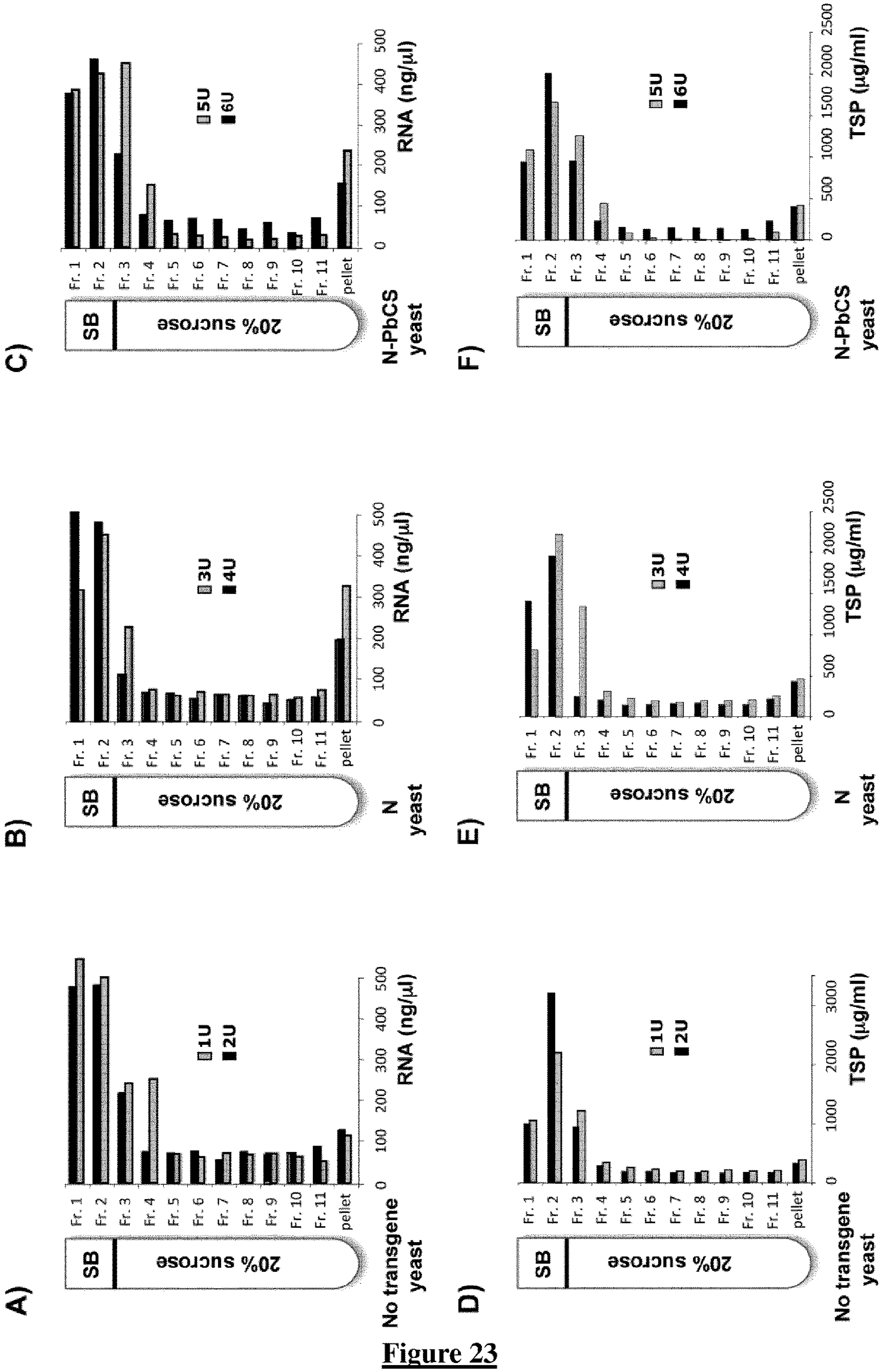

FIG. 23. Total RNA (A, B and C) and Total Soluble Protein (TSP; D, E and F) in fractions (Fr) and pellets from ultracentrifuged samples (U) in duplicate. (A and D) SMD1168 *P. pastoris* transformed with pPIC3.5K without insert; (B and E) SMD1168 *P. pastoris* expressing N; (C and F) SMD1168 *P. pastoris* expressing N-PbCS. SB: suspension buffer. PCR analysis targeting the gene insert demonstrated the absence of genomic DNA (of nucleus origin) in samples analysed by NanoDrop™ for total RNA content.

Figure 24:
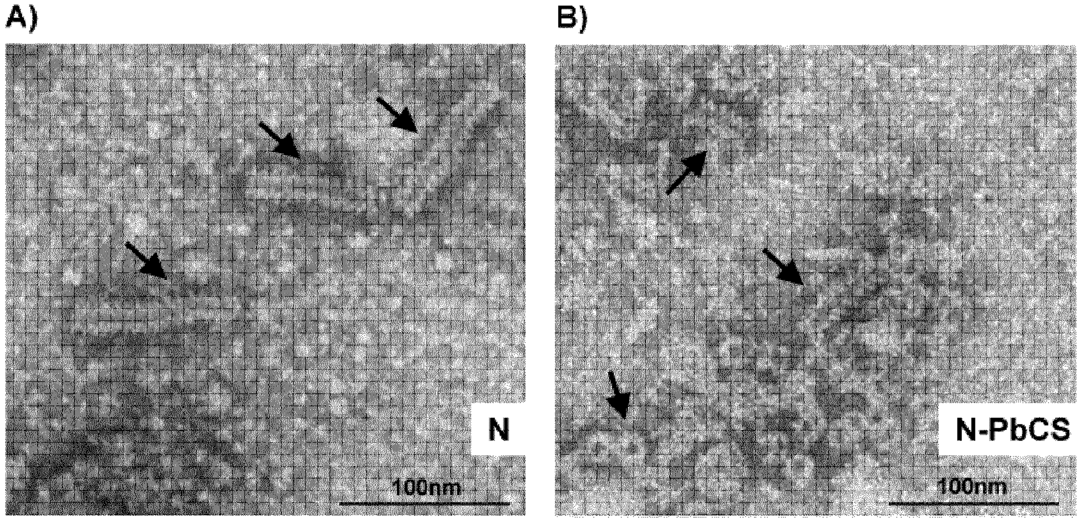

FIG. 24. Electron microscopy analysis of yeast lysates from SMD1168 *P. pastoris* expressing N (A) or N-PbCS (B). Scale bars are indicated. Black arrows highlight RNP rod and ring structures.

Figure 25:
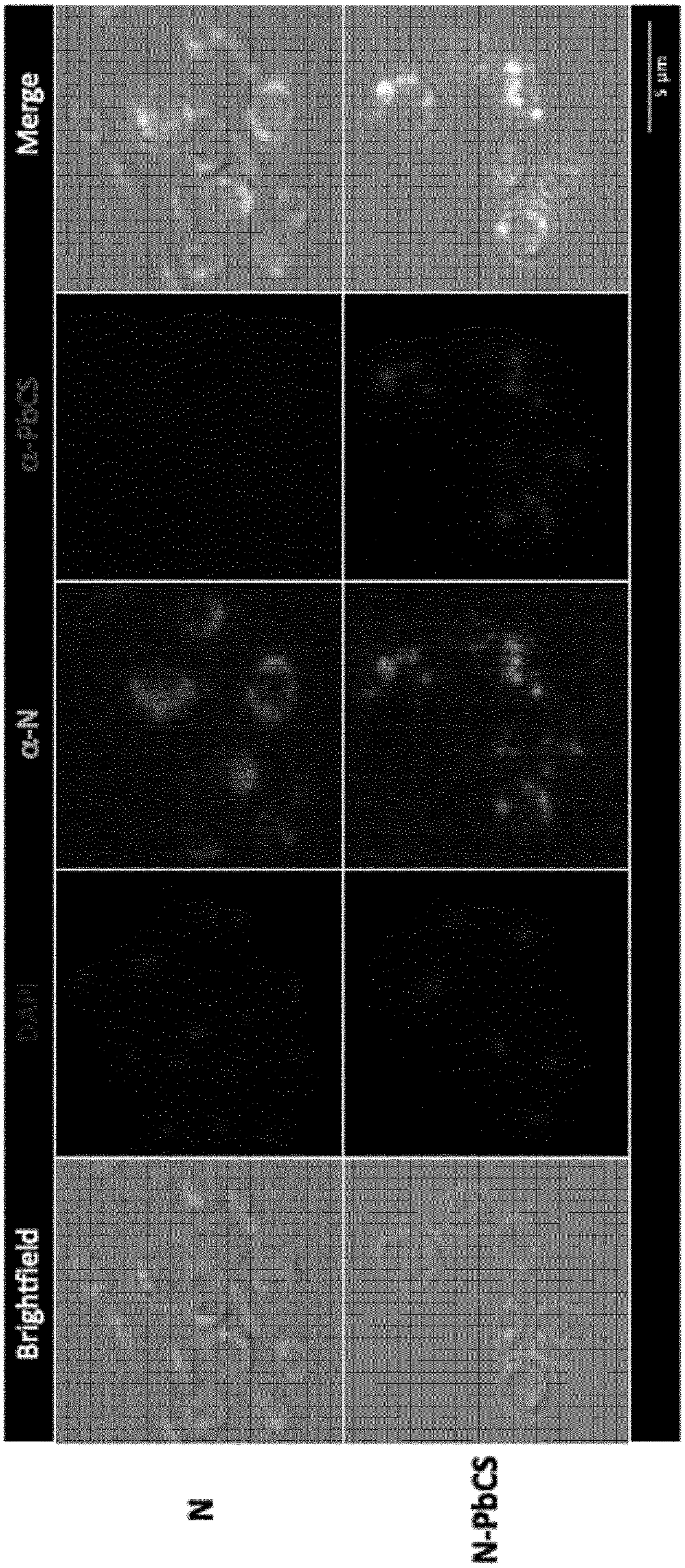

FIG. 25. Immunofluorescence analysis of N or N-PbCS expression in yeasts (N staining, third column; PbCS staining, fourth column; and nuclei, second column). Each image is the maximal intensity projection of three consecutive focal planes spaced 0.5 μm apart.

Figure 26:
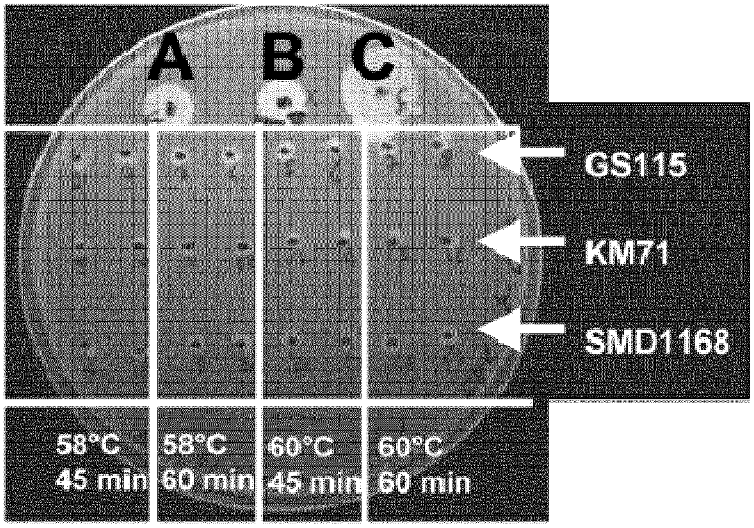

FIG. 26. Tests of *P. pastoris* reproductive activity on YPD plates following heat-inactivation. Each spot corresponds to 1 YU ($5\times10^7$ cells), out of 250 YU samples, loaded on YPD/agar plate and cultured over 7 days at 30° C. GS115 heat-treated samples are numbered on horizontal lines from 1 to 8, KM71 from 9 to 16 and SMD1168 from 17 to 24. (A) GS115, (B) KM71, and (C) SMD1168 samples were not submitted to heat-treatment, while all the other spots were submitted to 58° C. for 45 minutes (1,2, 9, 10, 17, 18) or 60 minutes (3, 4, 11, 12, 19, 20), and to 60° C. for 45 minutes (5, 6, 13, 14, 21, 22) or 60 minutes (7, 8, 15, 16, 23, 24). Untreated samples actively grew (A, B and C), while all heat-inactivated samples (from 1 to 24) were completely arrested in their reproductive activity (visible spots correspond to 1 YU loaded on plates).

Figure 27:
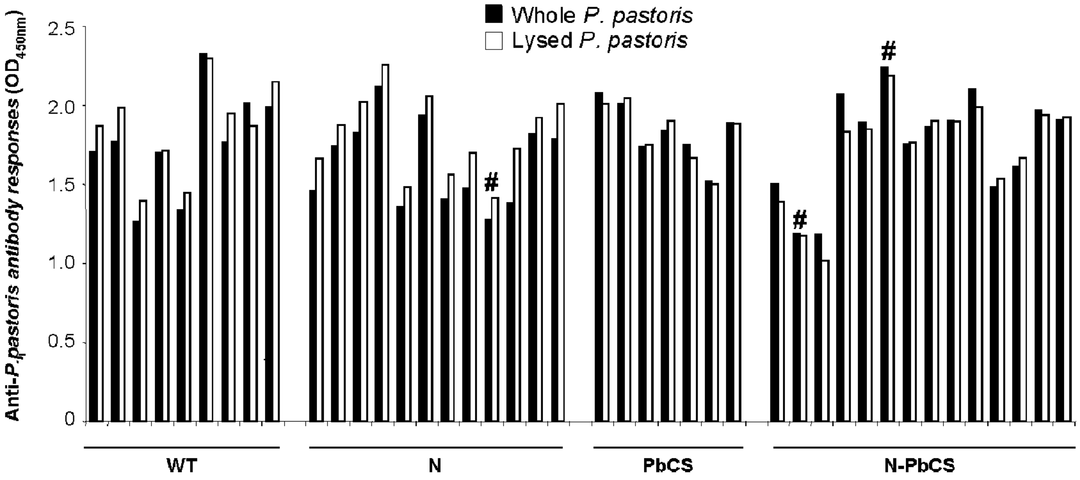

FIG. 27. Anti-*P. pastoris* IgG responses in immunized mice. Heat-inactivated wild type *P. pastoris* (25 YU) was directly coated (black bars) or coated following lysis (white bars). Results ($OD_{450\ nm}$) correspond to 1/1,000 dilution of serum samples from the WT, N, PbCS and N-PbCS immunized mouse groups. The naive group did not show cross-reacting antibodies recognizing *P. pastoris* (data not shown). Hash sign (#) highlights immunized mice that show negative anti-N responses (FIG. 4A).

EXAMPLES

Example 1

Recombinant Yeast Production and Characterization.

The N, PbCS and the PbCS nucleotide sequences were synthesized and optimized for expression in *P. pastoris* (GeneScript™), and cloned within EcoRI and NotI restriction sites into the pPIC3.5K plasmid (Invitrogen) for yeast expression under the control of the methanol-inducible AOX1 promoter. In the N-PbCS fusion protein, a linker of 7 amino acids (GAAGAGA) was inserted between the N and PbCS genes. GS115, KM71 and SMD1168 yeast strains were transformed by electroporation and plated on RDB plates (histidine-deficient medium) for the first round of clone selection (HIS+ 8 clones). Screening of clones with multiple inserts was performed on YPD-Geneticin plates at a final antibiotic concentration of 0.25 to 4.0 mg/ml (G8168-100, Sigma-Aldrich). Details on yeast culture mediums and plates are given in Invitrogen User Manuals for *P. pastoris.*

Kinetics and levels of N, PbCS and N-PbCS protein expression were monitored upon methanol induction. Yeast clones were cultured in BMG medium over weekend, then transferred to the BMM medium and protein production was induced and maintained by adding 0.5% methanol to cultures every 24 h. Before lysis, yeast cells were quantified by spectrophotometer analysis at $OD_{600\ nm}$. Collected culture samples were lysed every 24 h using acid-washed glass beads (425-600 μm; G8772 Sigma-Aldrich) and Breaking Buffer (Invitrogen). Following mechanic lysis, yeast extracts were centrifuged at 134 g for 10 minutes, and then supernatants clarified by centrifugation at 371 g for 15 minutes. Western blot (WB) was performed in denaturing conditions on 4-12% Bis-Tris polyacrylamide gels with XT MOPS buffer (Criterion 345-0123, Bio-Rad) using the Color Plus™ Prestained Protein Ladder (7-200 kDa; P7711 BioLabs), nitrocellulose membranes (Hybond™-C Extra RPN303E; Amersham Biosciences), and as primary antibodies the anti-N clones 25 or 120 (Buckland R et al., 1989, *J Gen Virol* 70 (Pt 2): 435-441) or the anti-PbCS antibody obtained through the Malaria Research and Reference Reagent Resource Center (MR4) as part of the BEI Resources Repository, NIAID, NIH: Mus musculus (B cell); Mus musculus (myeloma) 3D11, MRA-100, deposited by V Nussenzweig. Primary antibodies were at 1/1,000 dilution overnight at 4° C. and the secondary HRP-conjugated sheep anti-mouse IgG antibody (GE Healthcare UK Limited, NA931V) at 1/5,000 dilution for 1h30 at room temperature. In quantitative WB, selected clones were induced in BMM and cultures stopped at 54 h. Yeast was quantified (yeast unit; YU) by spectophotometer analysis ($OD_{600\ nm}$) and lysed. Lysed samples were diluted as indicated, and loaded on gel in parallel to the N standard protein (GenScript) at predefined quantities (10 to 20 ng). The anti-N clone 25 was used as primary antibody. N and N-PbCS band intensities were quantified by the Luminescent Image Analyzer LAS-1000plus (FUJIFILM) and reported on the N standard curve. Total soluble proteins (TSP) in lysates were measured by Bio-Rad Bradford Assay.

Size of MV RNPs expressed in *P. pastoris.*

After methanol induction for 54 h, yeast cultures were stopped on ice and samples (4,325 YU) were lysed and resuspended in 2 ml suspension buffer (SB: TrisHCl 25 mM pH 7.5, NaCI 50 mM, EDTA 2 mM in UltraPure™ DNase/RNase-Free Distilled Water) supplemented with anti-protease cocktail (Roche) and rRNasin RNase Inhibitor (Promega). The 2 ml samples were loaded on 9 ml 20% sucrose cushion in SB and centrifuged in SW41 Ti rotor for 1 h at 36,000 rpm at 4° C. Fractions of 1 ml were collected using the Masterflex® L/S® compact pump sampling machine (Cole-Parmer). Pellets were resuspended in 1 ml SB. Each aliquot including the pellet was analyzed for total soluble proteins (TSP), total RNA and N or N-PbCS protein concentrations by Bio-Rad Bradford Assay, NanoDrop™ 1000 Spectrophotometer, and anti-N or anti-PbCS sandwich ELISA. PCR analysis on lysed yeast cultures before and after centrifugation at 134 g and on clarified lysates was performed by a classical protocol using Taq DNA polymerase from Invitrogen and the 5' AOX1 (Invitrogen) and the 3' NOPT-INTER (5'-TTGTTCAGTCTGACCAGTCTC) (SEQ ID NO: 44) primers resulting in a 437-nucleotide band on recombinant yeast genome. Anti-N and anti-PbCS sandwich ELISA were performed by coating in sodium carbonate buffer (pH 9.6) 0.5 μg/ml of the mouse anti-N (MAB8906 Millipore) or 1/2,000 dilution of the MR4-100 anti-PbCS monoclonal antibody, and using the anti-N rabbit polyclonal IgG antibody (ABIN346975 Antibodies-Online GMBH) at 1/10,000 in 1xPBS as primary antibody, and the anti-rabbit IgG-HRP (NA934V Amersham Biosciences) at 1/7,000 dilution in 1xPBS as secondary antibody. Anti-N ELISA positive controls were SMD1168 expressing N protein, lysed and diluted at 1/200, 1/400 and 1/800 in 1×PBS. Anti-PbCS ELISA positive control was N-PbCS SMD1168 lysate (1/200) before loading on ultracentrifugation tube. ELISA plates were read with the EnSpire 2300 Multilabel Reader (Perkin Elmer) at OD450nm, using OD620nm as reference wavelength. Fractions and pellets collected from ultracentrifugation tubes with no yeast (SB only loaded on 20% sucrose) showed negative background of reagents in all the performed tests (ELISA, NanoDrop™ and Bradford).

A sedimentation calculation routine according to classical Svedberg equations has been used to predict the distance (cm) at which the protein of interest migrates from the upper surface of solutions in ultracentrifugation tubes. The calculation takes into account: (i) the protein mass and structure to estimate the vbar and Sw20 sedimentation parameters; (ii) ultracentrifugation tube characteristics and rotor diameter; (iii) sucrose percentage and volume for each solution phase; (iv) ultracentrifugation time; and (vi) rotation speed (rpm).

Electron Microscopy.

SMD1168 yeasts expressing N or N-PbCS were lysed and clarified as described above. EM was directly performed on N clarified lysate, while the N-PbCS clarified lysate was concentrated by ultracentrifugation on 20-60% sucrose gradient for 1 h30 at 32,000 rpm (SW32 Ti). The fractions at the interphase were collected, and further ultracentrifuged on 30% sucrose cushion for 4 h at 32,000 rpm (SW32 Ti) to collect the pellet. Samples were spotted on glow discharged carbon coated grids (EMS, USA) and negatively stained with NanoW™ (Nanoprobes, USA) (Desfosses A et al., 2011, *J Virol* 85: 1391-1395). Samples were then observed at 120 kV with a Philips/FEI CM 12 transmission electron microscope. Images were recorded using a KeenView™ camera (OSIS, Germany) and ITEM software (OSIS, Germany). RNP length and diameter were estimated as the average measures of 50 particles counted manually. Measurement standard deviation was 5%.

Immunofluorescence Analysis.

After induction of protein expression, 50 YU per sample were fixed by 3.7% formaldehyde. Cell wall was digested by zymolyase (Sigma-Aldrich: L2524-50KU), and cells were fixed again by methanol/acetone and attached to microscope slides as described in Keeling et al. (Keeling J W, Miller R K, 2011, *Methods Mol Biol* 782: 231-244). Cells were labeled with a rabbit polyclonal anti-MV-N (Covalab pab0035; 1/500 dilution) or MRA-100 mouse anti-PbCS monoclonal antibodies (1/1,000 dilution), then Alexa 488 goat anti-rabbit IgG (H+L) (Invitrogen A-11008; 1/500 dilution) or CY3-AffinityPure F(ab')2 Frag goat anti-mouse IgG (Jackson ImmunoReasearch 115-166-072; 1/1,000 dilution) as secondary antibodies. Brightfield and fluorescence images were acquired on a motorized inverted wide field fluorescence microscope. The system was controlled by the AxioVision software (Release 4.8.2.0, Zeiss) and was composed of a motorized inverted microscope (AxioObserver Z.1, Zeiss) equipped with a halogen illuminator (HAL100, Zeiss), a metal halide illuminator (HXP120, Zeiss) and a CCD camera (AxioCam M R, Zeiss). DAPI, Alexa Fluor and Cy3 were detected with specific filter sets. Stacks of 6 focal planes spaced 0.5 μm apart were acquired with a 100× oil objective (EC Plan-Neofluar 100×/1,30 Oil Iris, Zeiss). Images were then processed with the ImageJ software (Schneider C A et al., 2012, *Nat Methods* 9: 671-675).

Heat-Inactivation of *P. pastoris.*

GS115, KM71 or SMD1168 yeast strains were cultured in YPD medium at 30° C. and 250 YU were pelleted at 134 g for 10 minutes, medium was carefully removed and the yeast pellet treated at indicated temperatures and time points in a water bath. Heat-inactivation was stopped by transferring samples on ice. One YU of each sample was then plated on YPD/agar and cultured for 7 days at 30° C. The viability test was performed by adding 20 μl of methylene blue solution (Sigma-Aldrich; 0.05 mmol-1 3 in PBS pH 7.2) to the same volume of yeast cell suspensions and dead cell counting was performed under optical microscopy. For immunizations, whole SMD1168 wild-type yeast or yeast expressing N, PbCS or N-PbCS (54 h cultures) were heat-inactivated at 60° C. for 45 minutes and resuspended in 1×PBS at 30 YU/50 μl.

Mice Immunization, Flow Cytometry, Survival Rate and ELISA Analyses.

Six week old C56Bl/6 females were housed and included in experimental protocol groups following the European Directive 2010/63/EU. The experimental protocol was submitted and approved by the Ethic Comity Ile-de-France—Paris 1 (advise n$^{er}$ 2012-0009). Mice were daily monitored from arrival up to death (study endpoint). Mice were injected subcutaneously (50 μl) in correspondence of inguinal lymph nodes and bleedings (100 μl) were performed 3 days before the first immunization (day minus 3) or 6 h before next immunizations. Following the last bleeding (d42), mice were challenged at d43 with 6,000 sporozoites per mouse (1 μl, injected intradermally in the posterior footpad). Sporozoites were freshly collected by salivary gland dissection from *Anopheles stephensi* infected with Pb ANKA strain expressing the GFP ($GFP^+$) under the control of the hsp70 promoter [63]. Post challenge (c+), every day from $c^+3$ to $c^+7$, blood samples (2 μl) were taken from tails, diluted in 600 μl×PBS and analyzed in plates by Fluorescence Activated Cell Sorting (FACS; MacsQuant®, Miltenyi Biotec). Doublets and clusters of red blood cells (RBCS) were excluded from counts. Single $GFP^+$ RBCS (infected RBC, iRBCs) among total RBCS were estimated and data analyzed by the MACSQuantify™ Software. Post-challenge death was daily registered till total mouse extinction ($c^+29$). Mice weren't intentionally sacrificed before study endpoint, as the death score was necessary for determining the effect of vaccination on eventually enhanced resistance to cerebral malaria and/or prolonged survival. No alleviating treatment was acceptable for evaluating vaccine efficiency in this preclinical study. For IgG quantification in blood, sera from bleedings were separated from blood samples by Capiject® T-MG Capillary Blood collection System (Terumo Medical Corporation) and stored at −20° C. till ELISA tests. Anti-N IgG ELISA was performed by coating in wells 50 μg of >70% pure recombinant N protein (Genscript) and using the monoclonal mouse anti-N primary antibody (MAB8906, Millipore) at 1/5,000 and 1/20,000 dilutions in 1×PBS, Tween 0.05% and BSA 0.5% for positive controls. The anti-PbCS IgG ELISA was performed by coating in wells 50 μg of recombinant PbCS protein produced at the Recombinant Protein and Antibodies Production Core Facility of the Institut Pasteur, using the BioPod F800 microfermentor battery (Fogale Nanotech) (Frachon E et al., 2006, *Appl Environ Microbiol* 72: 5225-5231). The anti-PbCS monoclonal antibody from the MR4-100 reagent was used for positive controls at 1/4,000 and 1/10,000 dilutions. The anti-*P. pastoris* IgG ELISA was performed by coating 25 YU of whole or lysed wild type *P. pastoris* per well in sodium carbonate buffer (pH 9.6). Yeast was previously cultured, inactivated and lysed as described. Saturation of wells by whole or lysed yeast was defined by ELISA performed using an anti-*P. pastoris* rabbit polyclonal antibody (BP2240, Acris Antibodies) at 1/200 dilution and the anti-rabbit IgG-HRP (NA934V Amersham Biosciences) at 1/10,000 dilution. In all ELISA on serum samples, serial dilutions (1/100, 1/1,000, 1/10,000 and 1/100,000 for anti-N and anti-PbCS ELISA; 1/300 and 1/1,000 for anti-*P. pastoris* ELISA), the HRP-conjugated sheep anti-mouse IgG secondary antibody (NA931V, GE Healthcare UK Limited) at 1/5,000 dilution in 1×PBS, and the 3,3',5,5'-Tetramethylbenzidine substrate (TMB; Sigma-Aldrich) were used. ELISA development was stopped after 5 minutes with 2N H2SO4 and plates were read at $OD_{460\ nm}$, using $OD_{620\ nm}$ as reference wavelength. In ELISA determination of IgG isotypes, the polyclonal goat anti-mouse ads-HRP IgG (1030-05: dilution 1/8,000), IgG1 (1070-05; dilution 1/4,000), IgG2a (1080-05; dilution 1/4,000) and IgG2b (1090-05; dilution 1/4,000) from Southern Biotech were used as secondary antibodies. Sera were diluted by two folds from 1/50 to a maximum of 1/614,400. Titers were determined as the inverse of the highest sample dilution for which the $OD_{450\ nm}$ signal was greater than the cut off (the mean optical density plus 3 times the standard deviation of pre-immune control sera from mice under study). Mann-Whitney nonparametric and Spearman tests were performed using GraphPad Prism version 5.0b for Mac OS X, GraphPad Software, San Diego Calif. USA (www.graphpad.com).

Example 2

Intrinsic Properties of the RNP-Yeast Vaccine Platform

Comparison of Recombinant RNP Yeast Lysate and Whole Heat-Inactivated Yeast Formulations.

Antigen delivery within whole heat-inactivated yeast has proved highly efficient. The yeast cell wall components represent PAMPs (pathogen associated molecular patterns), which are recognized as danger signals by the immune system, notably by dendritic cells, making yeast a potent delivery vector (Neumann A. K. et al., 2010, *PLoS Pathog* 6, e1000760; Stubbs, A. C. et al., 2001, *Nat. Med.* 7, 625-629). To investigate the adjuvancy provided by internal yeast components, the inventors evaluated N-PbCS RNP delivery within yeast lysates and compared it to the whole yeast vaccine formulation. Yeast lysates (obtained by classical mechanic lysis with glass beads and partial removal of membrane and nucleus fractions) were produced, and recombinant protein content was measured by quantitative western blot. The established laboratory conditions for yeast lysate production proved highly reproducible.

Figure 1:
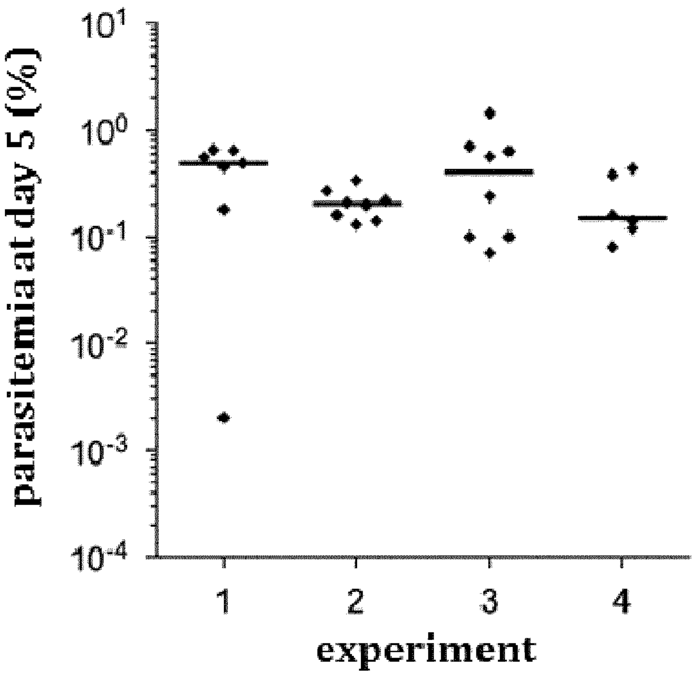
FIG. 1. Parasitemia at day 5 post challenge in naive mice from four independent experiments. Blood parasitemia is expressed in log 10 scale as the percentage of infected red blood cells (iRBCs) out of total RBCS. Median values of parasitemia are comparable among all groups of mice, as determined by the Mann-Whitney nonparametric test ($p>0.05$). The four independent experiments are named 1, 2, 3 and 4 on the x-axis.

To be able to compare protective efficacy results among different challenge experiments, the inventors evaluated the reproducibility of challenge in naïve mice using separate lots of *P. berghei* sporozoites in four experiments performed at different time points. Parasitemia at day 5 after challenge in all four groups was statistically comparable, according to analysis by Mann-Whitney nonparametric test (FIG. 1). Thus, the infectivity of sporozoite batches was reproducible, allowing the inventors to compare results obtained in independent challenge experiments.

Figure 2:
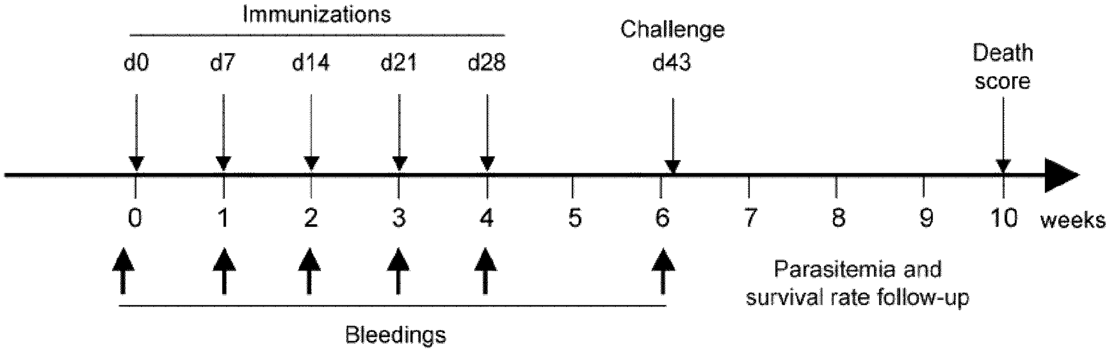
FIG. 2. Schematic representation of the immunization protocol. Immunization and challenge schedule are given in days (d) and bleeding time points in weeks.
Figure 3:
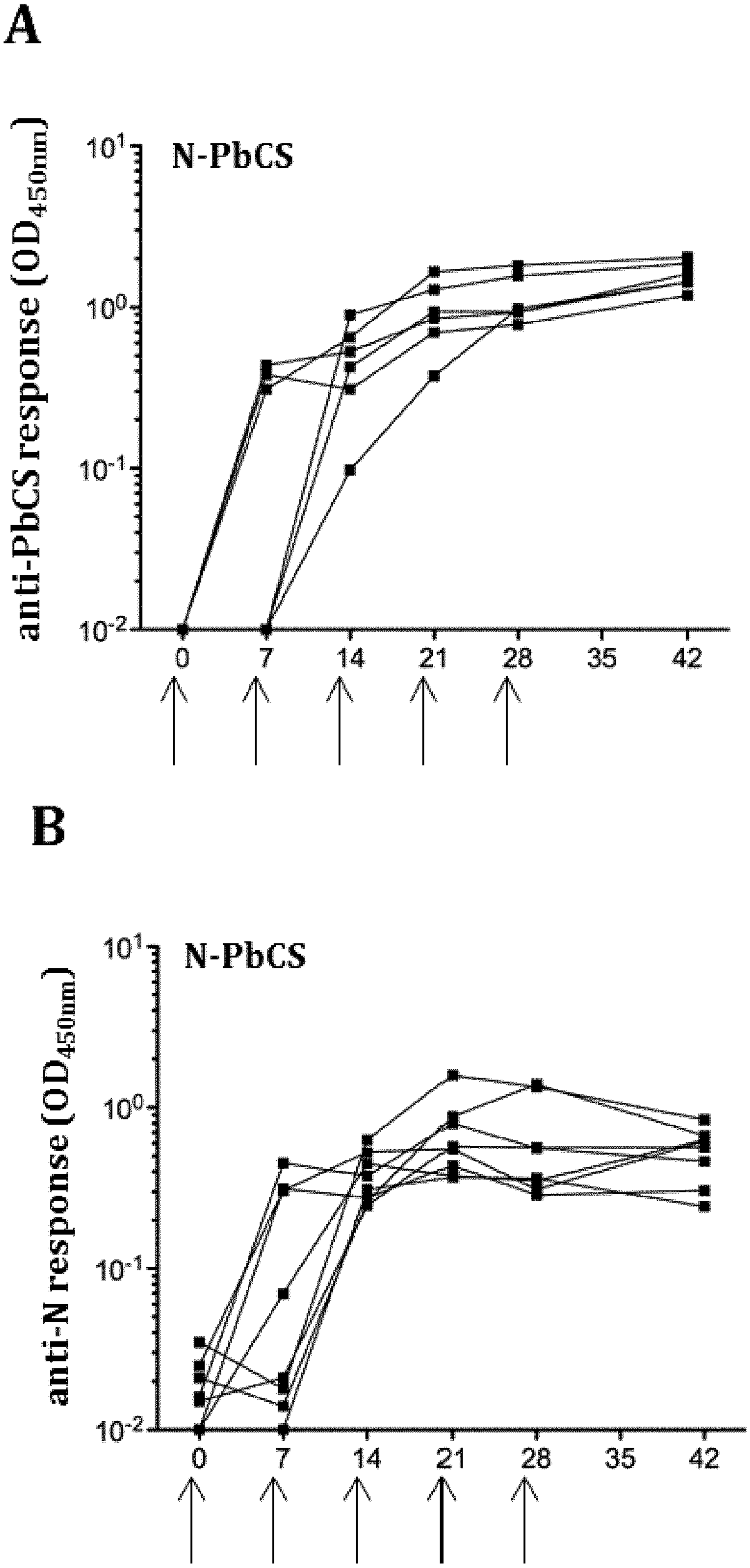
FIG. 3. Humoral responses elicited in mice after immunization with 30 YU N-PbCS non-adjuvanted yeast lysate. (A)—Kinetics of anti-PbCS IgG responses. (B)—Kinetics of anti-N IgG responses. $OD_{450\ nm}$ are expressed in $\log_{10}$ scale. Black arrows indicate immunization schedule. Mouse sera used at dilution $10^3$.
Figure 4:
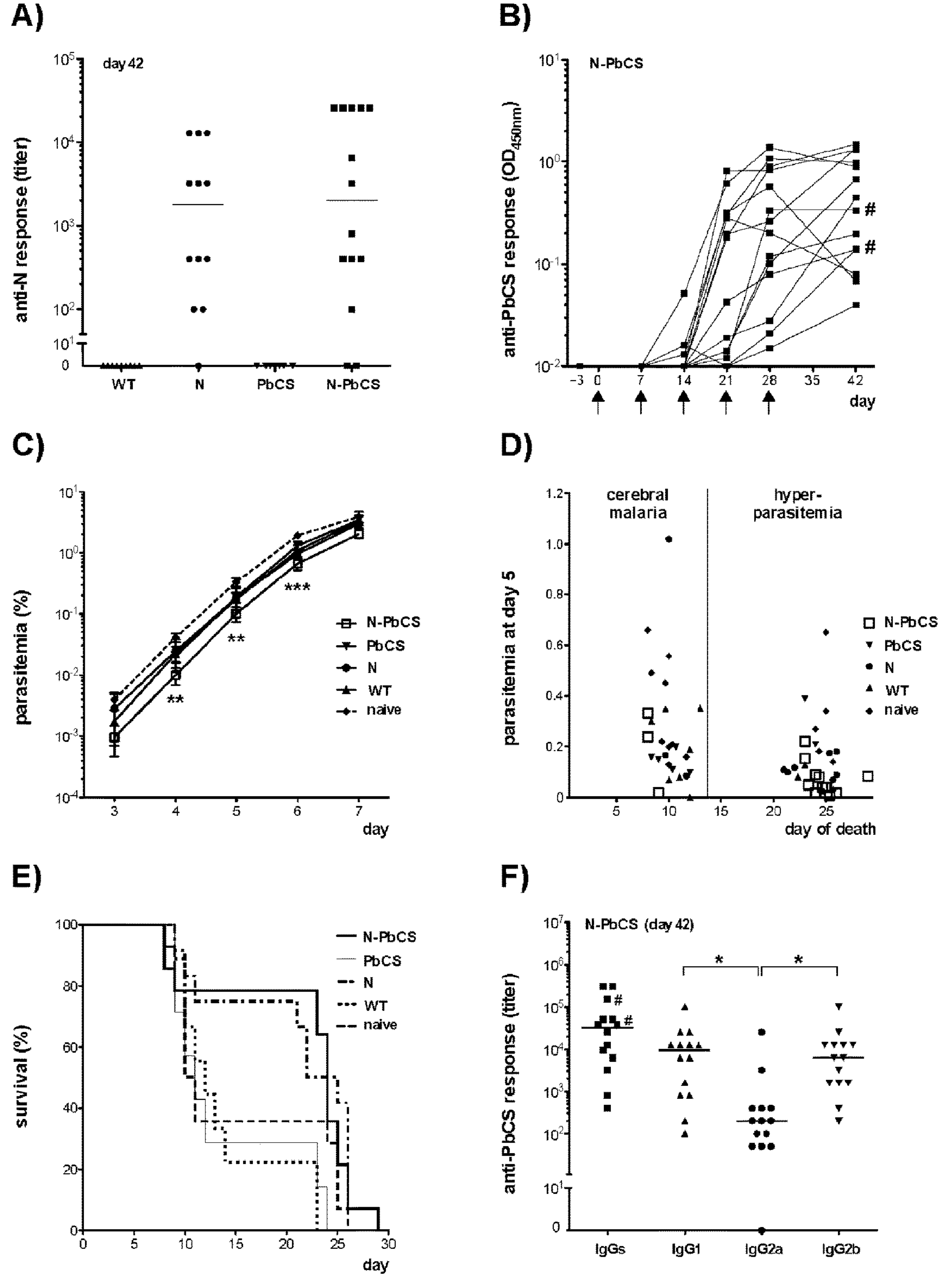
FIG. 4. Parasitemia delay and humoral response following immunization and challenge. (A) Anti-N IgG titers in mice serums collected at day 42 after immunization with WT yeast or yeasts expressing N or N-PbCS. Titers are expressed from 0 to $10^1$ in arithmetic scale, and from $10^2$ to $10^5$ in logarithmic ($\log_{10}$) scale. Specific symbols for N-PbCS mice indicate the same animals as in A, B and F panels. Median values were compared by the Wicoxon Two Sample Test ($p=0.4558$). (B) Kinetics of anti-PbCS IgG responses in mice immunized with N-PbCS yeasts. $OD_{450\ nm}$ are expressed in $\log_{10}$ scale. Black arrows indicate immunization schedule. Hash sign (#) indicates anti-N antibody negative mice in panel 10A. (C) Mean and standard deviations $\log_{10}$ values of the parasitemia of mice immunized by N-PbCS, N or WT yeast, and of naive (not immunized) mice following infection with 6,000 $GFP^+$ Pb sporozoites. Blood parasitemia is expressed in $\log_{10}$ scale as the percentage of infected red blood cells (iRBCs) out of total RBCS along the first 7 days follow up. Asterisks (*) indicate the significance level of the Mann-Whitney nonparametric test: one star corresponds to $p<0.05$ and two stars to $p<0.005$. (D) Inverse correlation between the day of death (x axis) and the percentage of iRBCs per total RBCS (y axis; arithmetic scale) per mouse. The cause of death is given in the upper part of the graph. (E) Survival curves of immunized mice after challenge with 6,000 $GFP^+$ Pb sporozoites. (F) Isotyping of humoral IgG responses at day 42 in mice immunized with N-PbCS. Bars correspond to median values per group. Titers are given in $log_{10}$ scale. Asterisks (*) indicate significant median differences ($p<0.05$; Mann-Whitney nonparametric test). Hash sign (#) indicates anti-N antibody negative mice in panel 10A.
Figure 5:
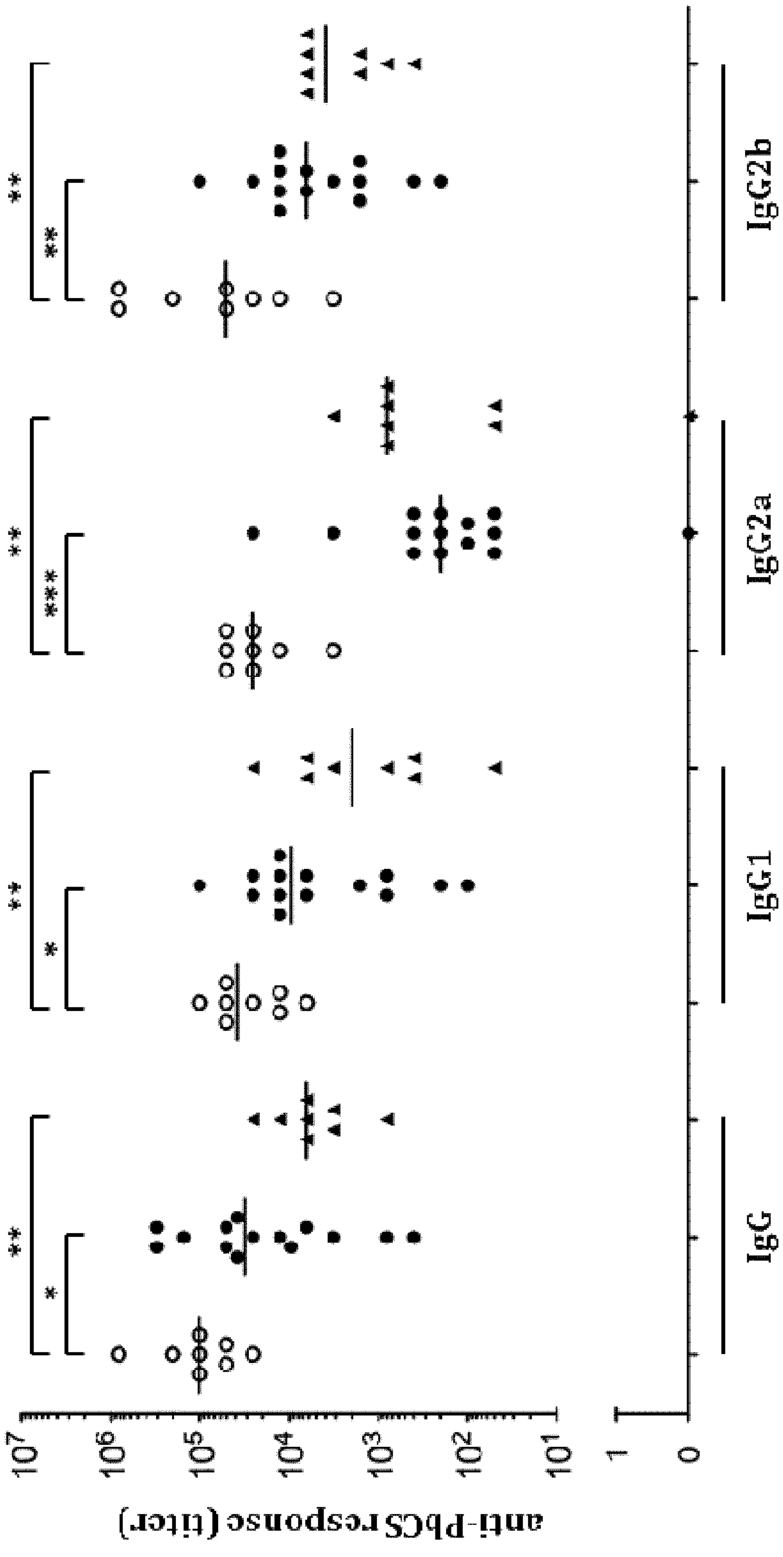
FIG. 5. Isotyping of humoral IgG responses at day 42 in immunized mice. Mice immunized with 30 YU N-PbCS yeast lysate (○), 30 YU N-PbCS whole heat-inactivated yeast (●) or 30 YU PbCS yeast lysate (▲). The bars correspond to median values per group. Asterisks (*) indicate significant median differences (one symbol for $p<0.05$, two for $p<0.005$, three for $p<0.0005$, Mann- Whitney nonparametric test).

The same immunization schedule and mice groups as for whole recombinant yeast were used for testing the N-PbCS RNP delivery within non-adjuvanted yeast lysates (FIG. 2). Anti-PbCS antibody responses appeared after 1-2 immunizations (FIG. 3A), while with whole heat-inactivated yeast they followed the 2nd-4th immunizations (FIG. 4B). Five immunizations with 30 YU of N-PbCS yeast lysates induced more homogeneous anti-PbCS antibody titers and higher titer levels (105) comparing to N-PbCS immunization within whole heat-inactivated yeast (3×104), as determined at the pre-challenge time point (FIG. 5). Moreover, different antibody isotype profiles (notably for IgG2a) between these two formulations indicated that the adjuvancy provided by lysed or whole yeast formulations has a different effect on Th1 and Th2 polarization of anti-PbCS immune responses. Anti-N responses detected in the N-PbCS lysate immunized group were apparent after 1-2 immunizations and reached the plateau level after the third one, maintaining this level following subsequent immunizations up to the pre-challenge time-point, while in mice immunized with whole heat-inactivated N-PbCS yeast anti-N antibodies appeared after 2-4 immunizations and in some mice continued to grow until the pre-challenge time point (data not shown).

Surprisingly, anti-PbCS responses were present even in mice immunized with yeast lysates carrying non-multimerized PbCS (which was not the case for the equivalent whole heat-inactivated formulation), however at a 2-log lower level than with the multimerized PbCS in lysate (FIG. 5) and 1-log lower, than with the multimerized PbCS in whole yeast formulation.

Figure 6:
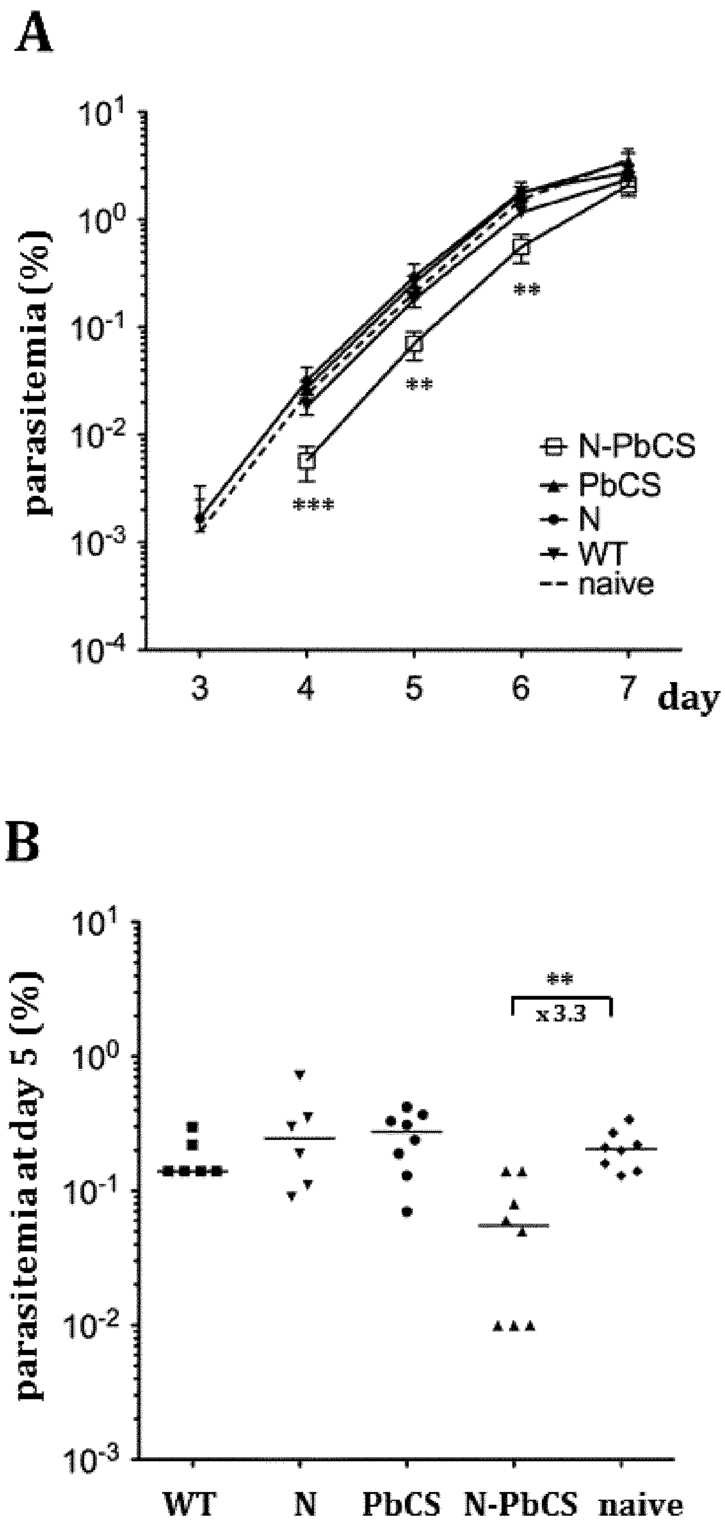
FIG. 6. Experimental challenge of immunized mice. (A)—Mean and standard deviations $log_{10}$ values of parasitemia in mice immunized with N-PbCS, PbCS, N or WT non-adjuvanted yeast lysates, and in non-immunized mice following infection with 8,000 $GFP^+$ P berghei sporozoites (experiment 2). Asterisks (*) indicate significant median differences (two symbols for $p<0.005$, three for $p<0.0005$; Mann- Whitney nonparametric test). (B)—Parasitemia at day 5 post-challenge. Bars correspond to medians. Asterisks (*) indicate significant median differences ($p<0.005$, Mann-Whitney -Whitney nonparametric test). Decrease in parasitemia in N-PbCS immunized group in comparison with the naive group is indicated in folds.

However, when immunized mice were challenged, non-multimerized PbCS mice showed no delay in parasitemia, indicating that the elicited anti-PbCS humoral responses were not protective against *P. berghei* infection, and that, for the whole yeast formulation, multimerized delivery of PbCS in yeast lysate was required to induce antigen-specific protective immune responses (FIG. 6A). Indeed, upon challenge with 8,000 *P. berghei* sporozoites, immunization with N-PbCS yeast lysate resulted in significant parasitemia delay with respect to the naive group (3.3-fold) (FIG. 6B). Comparable parasitemia delay was obtained by whole heat-inactivated yeast delivery of N-PbCS (4-fold).

These results indicated that yeast lysates deprived of the yeast cell wall provided adjuvancy, but as they represented only a part of the whole yeast delivery platform, they seemed to stimulate the immune system in a different manner. However, despite the fact that N-PbCS yeast lysates were more efficient in inducing anti-PbCS humoral responses rather than whole heat-inactivated N-PbCS yeast, the differences in anti-PbCS antibody titers and IgG isotype profiles between the two formulations were not predictive of differential impact of vaccination on parasitemia and the two formulations resulted in the same benefit against the *P. berghei* challenge.

PbCS Antigen Dose Escalation.

Delivery of N-PbCS RNPs within whole yeast cells was limited by the amount of yeast (30 YU) that could be safely administered to mice without causing serious local inflammation at the injection site (data not shown). The preliminary studies carried out by the inventors showed that three bi-weekly administrations of 30 YU of whole heat-inactivated yeast proved insufficient for inducing strong anti-PbCS antibodies and had no beneficial effect against challenge, while five weekly administrations of the same dose significantly reduced parasitemia and clinical outcomes as described above. As yeast lysates can be concentrated, delivery of RNPs within the yeast lysate formulation allowed to increase the dose of N-PbCS RNPs and to evaluate the efficacy of higher doses of N-PbCS on parasitemia.

Figure 7:
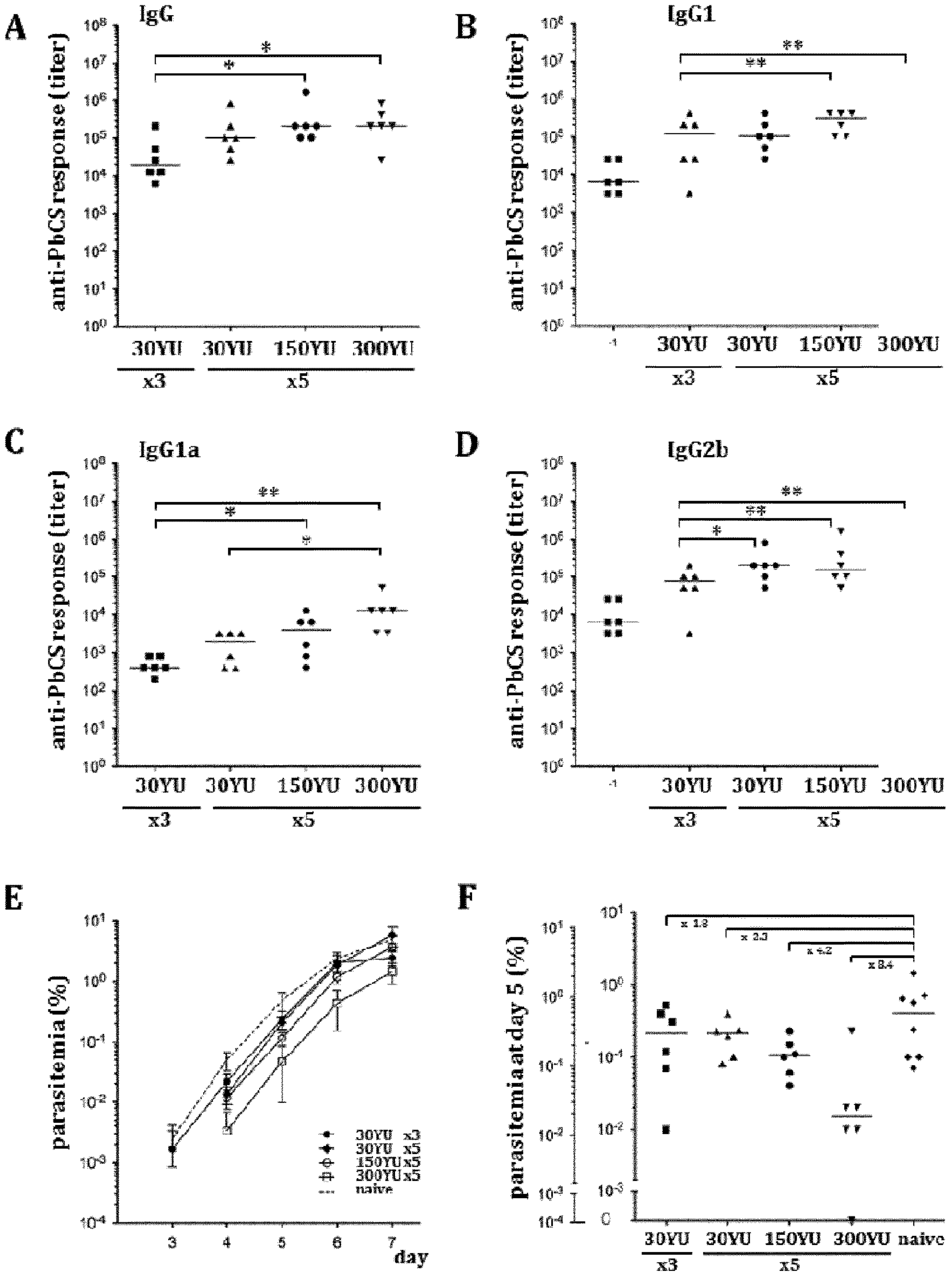
FIG. 7. Immunogenicity of N-PbCS at 30 YU, 150 YU and 300 YU in yeast lysates. Isotyping of humoral IgG responses at day 42: (A) IgG, (B) IgG1, (C) IgG2a and (D) IgG2b. The bars correspond to median values per group. Antibody titers of the non-parasitized mouse are encircled. (E)—Mean and standard deviations log10 values of parasitemia in mice immunized with N-PbCS at different doses and regimens and in non-immunized mice following infection with 10,000 GFP+ *P. berghei* sporozoites (experiment 3). (F)—Parasitemia at day 5 post-challenge. Bars correspond to medians. Decrease in parasitemia in immunized groups in comparison with the naive group is indicated in folds.

Comparison between five weekly doses of 30 YU, 150 YU and 300 YU of N-PbCS yeast lysates did not demonstrate a dose-dependent effect in N-PbCS humoral responses IgG titers being comparable and reaching 3×105, which seemed to be a plateau (FIGS. 7A,B,C,D). Moreover, comparison between three bi-weekly (30 YU×3) and five weekly (30 YU×5) immunizations with the same antigen/lysate dose showed that weekly injections were necessary to trigger earlier (from day 7) anti-N and anti-PbCS antibodies responses, as it was the case with the whole yeast formulation (data not shown). Indeed, at the pre-challenge time point (day 43) the anti-PbCS titers were increased by 1-log in the five weekly immunizations protocol comparing to the three bi-weekly immunizations protocol (2×105 and 1.9×104 median values, respectively) (FIG. 7A).

Parasitemia delay was dose-dependent, with three immunizations of 30 YU N-PbCS yeast lysate having no effect on parasitemia comparing to the naive group of mice, and five immunizations with 30 YU, 150 YU and 300 YU resulting in a 2.3-fold, 4.2-fold and 8.4-fold (non-parasitized mouse excluded from calculation) decrease in parasitemia at day 5, respectively (FIGS. 7E,F). Moreover, one mouse in the 300 YU group maintained negative parasitemia during all the study follow up (30 days post-challenge) and developed no clinical signs of malaria, indicating sterile protection against *P. berghei* infection. It was noted that mice receiving three or five immunizations with 30 YU of N-PbCS yeast lysate, presented less cases of cerebral malaria than mice receiving 150 YU and 300 YU (data not shown). However, the number of mice per group are insufficient to determine whether this effect was statistically significant.

Figure 8:
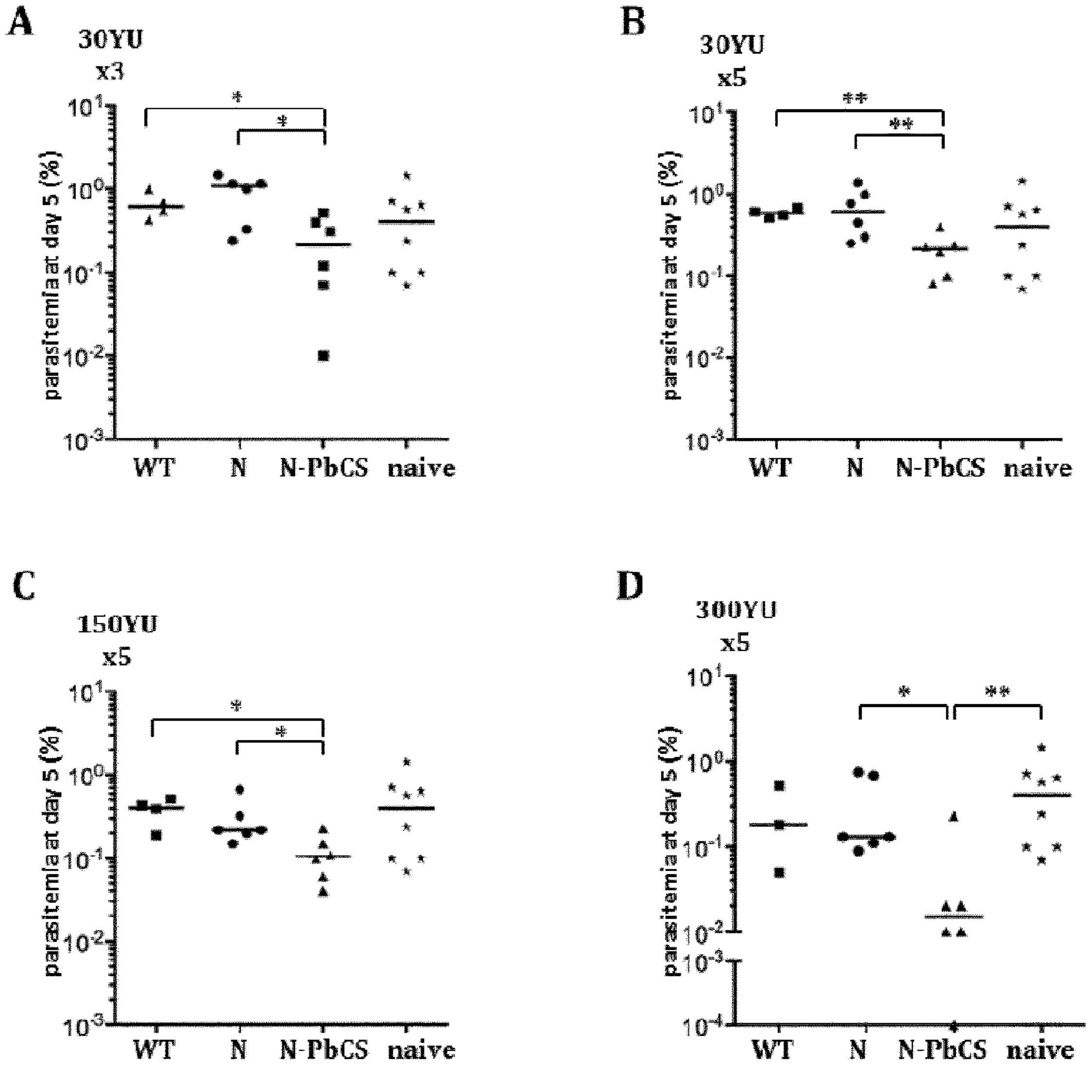
FIG. 8. Parasitemia at day 5 post-challenge. Groups of mice immunized with the following formulations and non-immunized mice from the same experiment.

Higher doses of yeast lysates (150 YU and 300 YU) were prepared by pooling several yeast lysate preparations, as pure RNP concentration was not technically possible. As a result the "yeast background" was increased proportionally in these formulations. Nevertheless, control groups of mice immunized with comparable doses of N and WT yeast were present all along the study, and no significant effect of N and WT yeasts was detected (FIG. 8).

The present data showed that higher doses of PbCS delivered on N-based RNPs enhanced protective efficacy of the vaccine candidate against *P. berghei* infection.

Preliminary Attempts to Decipher Immune Mechanisms Involved.

As described above, increased doses of N-PbCS obtained in yeast lysates provided better protection against challenge. In parallel, preliminary experiments with three mice immunized with 30 YU N-PbCS lysates adjuvanted with alum (aluminum hydroxide) showed that total anti-PbCS IgG responses were comparable to those induced by the equivalent non-adjuvanted lysate formulation (FIG. 9). However IgG antibody profiles induced by the two compared formulations differed (FIG. 9). Higher titers of IgG1 and lower titers of IgG2a and IgG2b indicated potentiation of Th2 responses by alum, in accordance with its intrinsic antibody stimulating properties (Gupta, R. K. et al., 2000, *Vaccine Adjuvants*). In the present model direct evidence of anti-PbCS T cell response implication could not be provided, as in C57Bl/6 mice no T cell epitopes from PbCS were identified, so implication of T cell responses was evaluated indirectly by anti-PbCS IgG isotyping.

To evaluate if experimental conditions could be found to induce sterile protection by immunizing with N-PbCS RNPs, high doses (50 YU, 100 YU and 150 YU) of N-PbCS yeast lysates (215 ng, 430 ng and 645 ng of PbCS, respectively) were administered to mice by three injections in a bi-weekly regimen in the presence of 50 μg per dose of alum adjuvant. The bi-weekly regiment was chosen, as our preliminary results indicated that five weekly immunizations with alum were not well tolerated by mice and resulted in increased susceptibility to challenge (data not shown). Immunization with alum-adjuvanted N-PbCS yeast lysates elicited a 1-log increase in anti-PbCS antibody titers in comparison to the highest responses obtained with 150 YU and 300 YU N-PbCS yeast lysates in the absence of alum adjuvant (FIG. 10). Notably, anti-PbCS antibody responses induced by all the alum-formulated doses (50 YU, 100 YU and 150 YU) have reached the same median titer at day 42 (106), which seemed to be the plateau of the anti-PbCS antibody response. In each of these groups two out of six mice were sterilely protected against challenge with 10,000 *P. berghei* sporozoites, while the other four demonstrated a significant decrease in parasitemia (9.7-fold, 8.7-fold and 6.7-fold at day 5 post-challenge in groups immunized with 50 YU, 100 YU and 150 YU, respectively, non-parasitized mice excluded from calculation) (FIG. 11). Among the three tested doses, the minimal dose (50 YU) of N-PbCS yeast lysates adjuvanted with was sufficient to induce PbCS-mediated protection. Notably, the unspecific benefit on parasitemia control previously observed with whole recombinant yeast expressing N was not identified in the group immunized with alum-adjuvanted N lysate.

As previously observed, there was no correlation between anti-PbCS antibody titers and sterile protection, as groups of mice represented relatively uniform outcomes in antibody titers, and sterilely protected mice did not show highest anti-PbCS titers. The decrease in parasitemia observed among the non-sterilely protected mice immunized with adjuvanted and non-adjuvanted N-PbCS lysates did not demonstrate the advantage of one formulation versus the other, assuming that high doses of N-PbCS had the most significant impact on protective efficacy in all vaccine candidates.

In conclusion, the inventors evaluated three different formulations for delivery of N-PbCS RNPs vaccine: whole recombinant yeast, yeast lysate without alum and yeast lysate adjuvanted with alum. Both lysate formulations allowed scaling up of the administered amount of the PbCS antigen, which could only be preliminarily optimized in whole recombinant yeast formulation. Significant parasitemia decrease (4-fold) was obtained by immunization with 30 YU (130 ng PbCS) of whole recombinant yeast, and this decrease could reach 8.4-fold by using 300 YU (1300ng PbCS) of yeast lysate without alum. N-PbCS RNPs (50-150 YU corresponding to 215-645ng PbCS) in combination with alum adjuvant produced sterile protection in some mice (two out of six) and significantly reduced parasitemia in other individuals from the same immunized group to the same extent as the in non-adjuvanted 300 YU group.

Multivalent Approach for Increased Efficiency of the RNP-Based Vaccine Candidate.

Immunization with N-PbCS RNPs delivered within whole heat-inactivated yeast provided uncontestable beneficial effect against *P. berghei* challenge, however was not protective. With results obtained in all the performed experiments, the inventors determined that the dose of N-PbCS in the heat-inactivated formulation was sub-optimal. By increasing the dose of N-PbCS in the lysate monovalent formulation, protective efficacy was enhanced, but could not bypass a certain threshold. This result was in accordance with multiple pre-clinical and clinical studies, which demonstrated that monovalent vaccine candidates based on the CS protein were not able to provide complete sterile protection against malaria (Schwartz et al., 2012, *Malaria Journal,* 11, 11). Thus, the inventors evaluated the possibility of using the recombinant RNP platform in whole heat-inactivated yeast for multimerizing other *Plasmodium* antigens and producing multivalent vaccine formulations.

To this aim five *P. berghei* proteins PbTRAP, PbSPECT, PbSPECT2, PbSUB1 and PbSUB2, which have functional and structural homologues in human-infecting *Plasmodium* species, were expressed in fusion with N in SMD1168 *P. pastoris* yeast using the same experimental strategy as for the PbCS gene. While TRAP from *P. falciparum* has already been evaluated in several subunit vaccine candidates (20% efficacy against infection in ChAd-MVA prime-boost formulation in human trials) (Ewer et al., 2013, *Nat. Commun.,* 4, 2836), to the knowledge of the inventors the other four proteins have never been tested for immunogenicity in pre-clinical or clinical trials. These *P. berghei* proteins were selected for explorative purposes based on their functional relevance during the pre-erythrocytic and erythrocytic stages of *Plasmodium* infection.

Selection of recombinant yeast clones expressing the highest amount of N-PbTRAP, N-PbSPECT, N-PbSPECT2, N-PbSUB1 and N-PbSUB2 fusion proteins was performed at different induction time points, similarly to N and N-PbCS selection. The optimal induction timing and the highest level of expression of these proteins were variable, but as for the PbCS antigen, the fusion protein yields were lower than the expression level of N alone and eventually of the antigen alone (Table 1).

TABLE 1

Expression of *P. berghei* proteins in SMD1168 *P. pastoris* yeast alone or in fusion with MV N.

| Antigen | Molecular weight | Level of expression | Induction time |
|---|---|---|---|
| N-PbTRAP | 114 kDa | 12 ng/YU | 54 h |
| N-PbSPECT | 79 kDa | 152 ng/YU | 78 h |
| N-PbSPECT2 | 118 kDa | 15 ng/YU | 54 h |
| PbSPECT2 | 60 kDa | 509 ng/YU | 54 h |
| N-PbSUB1 | 123 kDa | 12 ng/YU | 78 h |
| PbSUB1 | 65 kDa | 435 ng/YU | 54 h |
| N-PbSUB2 | 127 kDa | 23 ng/YU | 30 h |
| PbSUB2 | 69 kDa | 684 ng/YU | 30 h |

Immunogenicity and protective efficacy of the five obtained fusion proteins were first evaluated in monovalent formulations. Different parameters were tested to identify the optimal immunization protocols for each antigen, such as formulation (whole heat-inactivated yeast or alum-adjuvanted yeast lysate), dose (3 YU, 30 YU in both formulations, and 150 YU in alum-adjuvanted lysate) and administration schedule (three or five immunizations, weekly or bi-weekly) (Table 2). Due to the high variability of parameters, only 3 mice per group were used for screening them, and in three cases, when results were ambiguous, the experiment was re-conducted with 6 mice to verify the data (3+6 mice, Table 2). Depending on the immunization protocol, anti-TRAP and anti-SPECT2 antibodies could be detected at variable levels at pre-challenge time points. No anti-SPECT, anti-SUB1 and anti-SUB2 antibodies were detected among the evaluated immunization protocols by "homemade" ELISA (performed as described in Jacob et al., 2014, *PLoS ONE* 9,e86658, using *P. berghei* proteins recombinantly produced in *E. coli*). Levels of elicited anti-N antibodies were highly variable, depending on the formulation and the fused antigen.

Independently from humoral responses and immunization parameters used, neither of the antigen-formulation settings were protective against *P. berghei* challenge as judged by the absence of parasitemia delay in immunized groups at days 3 to 7 post-challenge comparing to groups of non-immunized naive mice (Table 2). Although the tested monovalent formulations did not afford protection, two combinations of heat-inactivated yeast expressing different N-antigens were evaluated. The first combination consisted of the mix of 15 YU N-PbSPECT2, 3 YU N-PbSUB1 and 15 YU N-PbSUB2 expressing yeasts, and the second consisted of 15 YU N-PbCS, 15 YU N-PbSPECT2 and 3 YU N-PbSUB1 expressing yeasts. Both combinations were administered in the whole heat-inactivated formulation (33 YU per immunization) in five weekly administrations. None of them were protective against *P. berghei* challenge. Thus the five *P. berghei* proteins evaluated in fusion with N with different yeast formulation (whole yeast or yeast lysate) did not provide any benefit with respect to parasitemia either in monovalent or in multivalent formulation. Identification of Plasmodium proteins with stronger antigenic properties is required to produce a multivalent vaccine candidate on the basis of recombinant RNPs delivered in whole heat-inactivated yeast. Nevertheless, the present study demonstrated that the yeast-RNP platform was potentially suited for designing multivalent vaccines by expression of a wide variety of antigens in fusion with MV N in yeast and mixing of these recombinant yeasts.

TABLE 2

Immunogenicity and protective efficacy of N-PbTRAP, N-PbSPECT, N-PbSPECT2, N-PbSUB1 and N-PbSUB2 monovalent formulations in mice.

| | Immunization parameters | | | | | Number | Readout | | |
|---|---|---|---|---|---|---|---|---|---|
| Antigen | Dose | Formulation | Adjuvant (alhydrogel) | Number of injections | Periodicity of injections | of mice per group | Anti-antigen anti-bodies | Anti-N anti-bodies | Parasitemia decrease |
| N-PbTRAP | 3YU | HI | no | 3 | bi-weekly | 3 | +/− | − | none |
| | 3YU | HI | no | 5 | weekly | 3 | +/− | +/− | none |
| | 30YU | HI | no | 3 | bi-weekly | 3 | +/− | +/− | none |
| | 30YU | HI | no | 5 | weekly | 3 | +/− | +/− | none |
| | 3YU | AL | yes | 3 | bi-weekly | 3 | − | + | none |
| | 3YU | AL | yes | 5 | weekly | 3 | − | + | none |
| | 30YU | AL | yes | 3 | bi-weekly | 3 | +/− | + | none |
| | 30YU | AL | yes | 5 | weekly | 3 | − | + | none |
| N-PbSPECT | 3YU | HI | no | 3 | bi-weekly | 3 | − | +/− | none |
| | 3YU | HI | no | 5 | weekly | 3 | − | +/− | none |
| | 30YU | HI | no | 3 | bi-weekly | 3 | − | + | none |
| | 30YU | HI | no | 5 | weekly | 3 | − | + | none |
| | 3YU | AL | yes | 3 | bi-weekly | 3 | − | +/− | none |
| | 30YU | AL | yes | 3 | bi-weekly | 3 | − | + | none |
| N-PbSPECT2 | 3YU | HI | no | 3 | bi-weekly | 3 | − | + | none |
| | 30YU | HI | no | 3 | bi-weekly | 3 + 6 | − | + | none |
| | 3YU | AL | yes | 3 | bi-weekly | 3 | − | − | none |
| | 30YU | AL | yes | 3 | bi-weekly | 3 | − | + | none |
| | 150YU | AL | yes | 3 | bi-weekly | 6 | +/− | + | none |
| N-PbSUB1 | 3YU | HI | no | 3 | bi-weekly | 3 | − | − | none |
| | 3YU | HI | no | 5 | weekly | 3 + 6 | − | +/− | none |
| | 30YU | HI | no | 3 | bi-weekly | 3 | − | − | none |
| | 30YU | HI | no | 5 | weekly | 3 | − | − | none |
| | 3YU | AL | yes | 3 | bi-weekly | 3 | − | +/− | none |
| | 30YU | AL | yes | 3 | bi-weekly | 3 | − | + | none |
| | 150YU | AL | yes | 3 | bi-weekly | 6 | − | + | none |
| N-PbSUB2 | 3YU | HI | no | 3 | bi-weekly | 3 | − | − | none |
| | 3YU | HI | no | 5 | weekly | 3 | − | − | none |
| | 30YU | HI | no | 3 | bi-weekly | 3 | − | − | none |
| | 30YU | HI | no | 5 | weekly | 3 + 6 | − | − | none |
| | 3YU | AL | yes | 3 | bi-weekly | 3 | − | +/− | none |
| | 30YU | AL | yes | 3 | bi-weekly | 3 | − | + | none |
| | 150YU | AL | yes | 3 | bi-weekly | 6 | − | +/− | none |

HI—heat-inactivated yeast,
AL—alum-adjuvanted yeast lysate.
Antibody responses are highlighted« + » if detected in all mice, « +/− » if detected in some mice and « − » if not detected in any mice from the group.

Expression Optimization for Whole Heat-Inactivated Yeast Delivery: N-PbCS and N-PfCS.

Mice immunization with N-PbCS yeast lysates had clearly demonstrated the correlation of N-PbCS dose with the beneficial outcome. Relatively high throughput selection of *P. pastoris* SMD1168 clones expressing N-PbCS was tried by screening N-PbCS clones by ELISA rather than by western blot. By this methodology, up to 80 clones were tested, but this attempt resulted in clones all with similar levels of N-PbCS expression to the clone used in this study. This suggested that either higher throughput selection should be performed or that intrinsic properties of the PbCS protein and of yeast were responsible for the plateau level of N-PbCS expression (primary amino acid structure or toxicity for the yeast cell). To test the second hypothesis, the inventors evaluated the production of truncated versions of PbCS in fusion with N. As the central repeated portion of the protein was highly immunogenic, the N- and C-terminal domains of PbCS were alternatively deleted from the N-PbCS fusion gene (FIG. 12). SMD1168 yeasts were transformed with one of the two truncated PbCS forms (PbCS-ENterm or PbCS-ECterm) in fusion to N as previously described. The N-truncated clone of N-PbCS (N-PbCS-ENterm) could not be obtained in SMD1168, while the C-truncated version (N-PbCS-ECterm) was expressed in the best selected clone at 237 ng/YU, which is 20-fold higher than the full-length N-PbCS (12 ng/YU) (Table 3). This result indicated that the amino acid composition of distinct protein domains impacted the level of expression of the fusion protein.

The inventors then evaluated the expression level of PfCS, the CS antigen from the human-infecting *P. falciparum* parasite, in fusion with N in *P. pastoris*. N-PfCS was successfully expressed in GS115 and KM71 at 97 ng/YU (Table 3), which is nearly 1-log higher than N-PbCS used in pre-clinical studies described above (Jacob et al., 2014, *PLoS ONE* 9, e86658). This suggested that expression of proteins in fusion with N in *P. pastoris* was sequence and yeast strain specific, and that further PbCS and PfCS sequence optimization were required for producing yeast clones with higher expression levels in the context of optimizing whole recombinant yeast evaluation as malaria vaccine candidate.

TABLE 3

Optimization of PbCS and PfCS expression in fusion with MV N in *P. pastoris* yeast.

| Antigen | Molecular weight | Level of expression GS115 | KM71 | SMD1168 | Induction time |
|---|---|---|---|---|---|
| N | 58 kDa | 1246 ng/YU | 1139 ng/YU | 871 ng/YU | 54 h |
| N-PbCS | 91 kDa | N-A | N-A | 12 ng/YU | 54 h |
| PbCS | 32 kDa | - | - | 16 ng/YU | 54 h |
| N-PbCS-ΔCterm | 83 kDa | - | - | 237 ng/YU | 54 h |
| N-PbCS-ΔNterm | 86 kDa | - | - | N/A | |
| N-PfCS | 93 kDa | 97 ng/YU | 97 ng/YU | - | 54 h |

« - » indicates that protein expression in the given conditions was not attempted, « N/A » indicated that protein expression could not be obtained due to rapid degradation.

Example 3

Whole Recombinant Yeast Against Other Infectious Diseases: The Example of *Enterovirus* 71 (EV-71).

Due to its immunogenic properties and auto-adjuvancy, the inventors suggested that the yeast-RNP platform could be applied to a variety of pathologies affecting humans. To prove this, the inventors investigated the efficiency of this new vaccine platform against infection by the *enterovirus* 71 (EV71). EV71 is the cause of hand-foot-and-mouth disease (HFMD), which seriously affects children under 5 years of age causing neurological complications and leading to fatalities (Solomon et al., 2010, *The Lancet Infectious Diseases,* 100, 778-790). The major antigenic VP1 capsid protein (Chen et al., 2008, *Vaccine,* 26, 2882-2889; Wu et al., 2001, *Vaccine,* 20, 895-904) of the EV-71 virus, was fused C-terminal to N (FIG. 13) as previously described for PbCS. *P. pastoris* was transformed, and contrarily to N-PbCS, N-VP1 was expressed in the GS115 strain at 94 ng/YU, but was degraded in the SMD1168 strain (Table 4), suggesting once again that sequence specificity and optimal yeast strain had to be evaluated experimentally for every given antigen. The possibility of fusing EV71 VP1 to N and maintaining RNP formation was validated by electron microcopy analysis, on fractions included in the Mix sample, following yeast lysis and ultracentrifugation (FIGS. 14A, C and D). The presence of VP1 on recombinant RNPs was demonstrated by western blot analysis on the Mix sample visualized by electron microscopy (FIG. 15).

TABLE 4

Expression of EV-71 protein VP1 in *P. pastoris* yeast alone or in fusion with MV N.

| Antigen | Molecular weight | Level of expression SMD1168 | GS115 | Induction time |
|---|---|---|---|---|
| N-VP1 | 91 kDa | N/A | 94 ng/YU | 30 h |
| HtVP1 | 33 kDa | — | 3 ng/YU | 30 h |
| VP1 | 32 kDa | — | 5 ng/YU | 54 h |

Neutralizing anti-VP1 antibodies correlate with protection from EV-71 (Lee et al., 2010, *Expert Rev Vaccines* 9, 149-156; Wu et al., 2001, *Vaccine,* 20, 895-904). Immunization protocols with whole N-VP1 recombinant yeast are ongoing and serums are collected for evaluation of anti-VP1 humoral responses. As EV-71 infection occurs through the oral route, this virus provides a perfect model for testing the relevance of oral immunization with whole yeast carrying N-VP1 RNPs, in order to elicit mucosal immunity directly at the site of viral infection.

Immunization with Recombinant *P. pastoris* Recombined to Produce RNPs Exposing on their Surface the VP1 Protein The schematic representation of the immunization protocols are disclosed on FIG. 16. To summarize, immunization of mice (C57BL/6) with heat-inactivated *P. pastoris* yeast expressing the VP1 protein as a fusion protein in RNPs according to the invention, was carried out either subcutaneously or orally according to distinct regimens disclosed in the figure as protocol A or B. The administered doses of yeast were 0, 0.3, 3 and 30 YU depending on the experiment. Following multi doses administration according to the A or B protocols, boosting doses were administered at day 58.

ELISA was performed in order to determine the anti-VP1 titers resulting from the various experiments and the best results are reported in FIG. 17; anti-N antibody titers were also measured in the same immunization context (FIG. 18).

When administered sub-cutaneously, the heat-inactivated yeast provided a higher immunization at a dose of 30 YU, i.e. at the highest tested dose, with the lowest number of injections (according to protocol B). The same conclusion was achieved for both N and VP1 antigens. By contrast, oral immunization did not raise a clear response against the VP1 protein (background signal was observed and the boost a day 58 did not show a clear effect). Against the N protein, the lowest dose administered (0.3 YU) provided the best result when it was administered with the lowest number of administration (protocol B).

Example 4

Cleavage Sites of Proteases in Yeast

In yeast cells, proteases recognize specific cleavage sites in expressed heterologous proteins. These proteases and their cleavage sites are not yet described. Different *P. pastoris* strains (i.e. GS115 vs SMD118) possess specific proteases. Hence, once a recombinant protein is expressed in a specific yeast strain, it may undergo degradation by *P. pastoris*-strain-associated-proteases. Experimentation performed on many N—X fusion proteins (where X is the antigen of interest) showed that in function of X, the N—X digestion profile (as revealed following N—X induction, yeast lysis, and anti-N and anti-X WB) was X-specific, highly reproducible in the same yeast strain at the same time point of protein induction, and few protein bands were revealed. It was not clear if this profile corresponded to reality inside intact yeast cells, as to analyze this profile, yeast had to be lysed. Proteases may act following lysis and lysate manipulation (even if an anti-protease cocktails is used during lysis). But in any case, the protein digestion profile corresponded to protease cleavage at highly specific sites.

In both whole and lysate yeast formulations, all variants in length (if real) of the N—X protein were present in the vaccine batch and hence protease activity was irrelevant once the vaccine platforms were calibrated for parameters used to produce the vaccine batch.

But, one may always keep in mind that it may be possible to increase N—X full-length production inside yeast and/or vaccine immunogenicity by changing the *P. pastoris* production strain or by modifying empirically the protein sequence in correspondence of protease cleavage sites to change the digestion profile of the N—X protein. Mapping of cleavage sites may be performed by mass spectrometry and protein sequencing analyses of the N—X protein bands. Neutralization of cleavage sites will increase N—X full-length relative production.

Results

Expression of Measles Virus Nucleoprotein in *P. pastoris*.

The nucleotide sequence encoding the nucleoprotein (N) of measles virus vaccine (MV) Schwarz strain (Combredet C et al., 2003, *J Virol* 77: 11546-11554) was optimized for expression in *P. pastoris* and cloned into the pPIC3.5K plasmid under the control of the methanol-inducible AOX1 promoter. Three strains of *P. pastoris* (the commonly used GS115 and KM71, as well as SMD1168, which is deficient in proteinase A activity) were transformed with the recombinant plasmid and 10 positive clones per strain were amplified. A first kinetic study of N expression was performed by western blot analysis of yeast lysates. The optimal time point for N expression was found to be 54 hours (h) after methanol induction for the three *P. pastoris* strains. The best N-expressing clone for each strain was then selected by western blot analysis of yeast lysates collected 54 h after induction. These clones showed the highest expression of full-length undegraded N of comparable weights (FIG. 19). The N expression was further characterized in the GS115, KM71, and SMD1168 best clones by Bradford analysis and quantitative western blot. The N protein was expressed at the predicted apparent molecular weight with no visible degradation or processing. The amount of N protein expressed was around 1 μg per yeast unit (YU). In the GS115 and KM71 strains, N production accounted for as much as 24% of total soluble proteins (TSP), while this was only 14% in the SMD1168 strain (Table 5). The expression levels in GS115 and KM71 were in the same range as previously shown for these strains (Slibinskas R et al., 2004, *J Biotechnol* 107: 115-124).

TABLE 5

Amount of N protein expressed in *P. pastoris* GS115, KM71 and SMD1168 strains. One YU corresponds to $10^7$ yeast cells.

| | *P. pastoris* strain | | |
|---|---|---|---|
| | GS115 | KM71 | SMD1168 |
| N protein amount per YU (μg) | 1.25 | 1.14 | 0.87 |
| Total soluble protein (TSP) per YU (μg) | 5.11 | 4.63 | 5.98 |
| N protein/TSP (%) | 24 | 24 | 14 |

Expression of N-PbCS in SMD1168 *P. pastoris*.

To test the possibility of using MV-N-based RNPs as carrier to multimerize heterologous antigens in malaria vaccine prototypes, the inventors fused the circumsporozoite (CS) antigen (Nussenzweig V, Nussenzweig R S, 1985, *Cell* 42: 401-403) from Pb (ANKA strain) to the C-terminus of MV-N through a linker of 7 amino acids (FIG. 20A; FIG. 21; Kyte J, Doolittle R F, 1982, *J Mol Biol* 157: 105-132). The choice of using Pb opens access to the mouse animal model to evaluate the immunogenicity and efficacy of the vaccine prototype by vaccination and parasite challenge (Scheller L F et al., 1994, *Infect Immun* 62: 4844-4847 ; Craig A G et al., 2012, *PLoS Pathog* 8: e1002401). GS115, KM71 and SMD1168 *P. pastoris* strains were transformed by pPIC3.5K bearing the N-PbCS encoding gene under the control of the AOX1 methanol-inducible promoter. Induction of N-PbCS in GS115 and KM71 strains resulted in the rapid degradation of the fusion protein (data not shown), while the full-length fusion protein was correctly produced in SMD1168 strain (FIG. 20B). The maximum expression of N-PbCS was obtained at 54 h after induction. In the best N-PbCS expressing clone selected by qualitative and quantitative western blot, the expression level of fusion protein (12 ng/YU) was 73 times lower than N alone (871 ng/YU) in the same strain (Table 5; FIG. 20C). Thus, full length N-PbCS fusion protein could only be expressed in SMD1168 *P. pastoris* and at a nearly 2-log lower level than the N protein alone. In order to obtain control yeast with the monomeric form of the *Plasmodium* antigen, an SMD1168 clone expressing PbCS alone was generated and selected as previously described. PbCS yeast showed a comparable expression level of the antigen alone (16 ng/YU) to that of the N-PbCS fusion protein (12 ng/YU). The replication kinetics of recombinant SMD1168 yeasts expressing N, PbCS or N-PbCS were strictly comparable in all tested culture media (YPD, BMG and BMM), and no macroscopic phenotype difference was observed between recombinant and wild-type SMD1168 yeasts.

Production of High Molecular Weight N-Based Ribonucleoproteins in *P. pastoris*.

The MV-N nucleoprotein has the capacity to auto-assemble around RNA in the cytoplasm of mammalian, bacterial or yeast cells (Bourhis J M et al., 2006, *Virology* 344: 94-110; Warnes A et al., 1995, *Gene* 160: 173-178; Slibinskas R et al., 2004, *J Biotechnol* 107: 115-124). To assess whether N and N-PbCS were assembled into high-molecular weight RNPs in SMD1168 *P. pastoris*, yeast lysates were ultracentrifuged on 20% sucrose and the presence of N and PbCS proteins was quantified in fractions and pellets (FIG. 22). Although N multimerization may impact the affinity of RNPs of different size for anti-N antibodies used for quantification, a comparison of N amounts can be performed among fractions at similar levels in N and N-PbCS samples. For both recombinant yeasts, the profile of N and N-PbCS distribution on sucrose showed the presence of monomeric or oligomeric N in the upper fractions, multimeric forms in the middle fractions and highly multimeric RNPs in the pellets. Notably, the inventors estimated by calculation routine that RNPs present in the pellets were heavier than 36,502 kDa, assembling more than 628 N molecules. The 2-log difference in read out between the two recombinant yeasts relates to the 2-log difference in N expression level between N and N-PbCS yeasts (871 ng/YU versus 12 ng/YU).

Remarkably, in N-PbCS recombinant yeast, N was predominantly found in the pellet. Quantitative western blot analysis of N-PbCS pellets demonstrated that RNPs were mainly constituted of N (70-80%) and that full length N-PbCS protein represented 10-20% of total N. In addition, recombinant RNPs contained 10% of degraded N-PbCS proteins (data not shown). The imbalanced profile of N-PbCS yeast may be due to RNP pull down by interaction of PbCS antigen with subcellular elements or alternatively to RNPs stabilization by N-PbCS fusion resulting in highly multimeric RNPs. Heterologous antigen expression did not modify yeast RNA and TSP patterns as compared to wild-type yeasts (FIG. 23). Theses profiles were maintained independently of yeast amounts loaded on sucrose (data not shown).

To look for the structure of RNPs, yeast lysates were observed by electron microscopy (EM). In the N recombinant SMD1168 yeast, the inventors found numerous RNPs with herringbone shape of 20-22 nm diameter and variable rod length of 30 to 200 nm (FIG. 24A). This finding was similar to that previously described in recombinant *P. pas-*

*toris* GS115 strain (Slibinskas R et al., 2004, *J Biotechnol* 107: 115-124) and in mammalian cells infected by MV (Griffin D E, 2001, *Fields Virology*. Philadelphia: *Lippincott Williams & Wilkins Publications*. pp. 1401-1441). In the N-PbCS sample, RNPs appeared less rigid than N-only RNPs with length spanning from 30 to 70 nm. Most N-PbCS RNPs were detected in microenvironments where discrete rings were visible next to rod structures (FIG. 24B). Because of the lower expression level of N-PbCS as compared to N, the N-PbCS clarified lysate was submitted to two ultracentrifugation rounds to concentrate N-PbCS structures, while N sample was not. This explains the differences observed in average rod length in both samples, as previously observed (Slibinskas R et al., 2004, *J Biotechnol* 107: 115-124). Moreover, after the first round of ultracentrifugation, the inventors selected the fractions containing RNPs of around 333 N molecules, which represented the major population as compared to shorter or longer RNP structures present in the other ultracentrifugation fractions or pellet. This assumption was made taking into account that 1 N molecule associates with 6 RNA ribonucleotides (Griffin D E, 2001, *Fields Virology*. Philadelphia: *Lippincott Williams & Wilkins Publications*. pp. 1401-1441), and that eukaryotic mRNAs have an average size of 2 kb (Jackson D A, Pombo A, Iborra F, 2000, *FASEB J* 14: 242-254). RNP selection was then performed on the basis of a sedimentation calculation routine (see Methods). The presence of lighter and heavier N-PbCS RNPs in lysate as well as of N-PbCS fusion protein in selected RNPs was put in evidence by anti-PbCS/anti-N sandwich ELISA on all 1 ml fractions taken from the top to the bottom of tubes from both ultracentrifugation rounds (data not shown).

Immunofluorescence analysis of N or N-PbCS recombinant SMD1168 yeasts showed that RNPs localized in large and compact cytoplasmic inclusions, as previously observed for N alone in GS115 *P. pastoris* (Slibinskas R et al., 2004, *J Biotechnol* 107: 115-124), and that N inclusions co-localized with PbCS in N-PbCS yeasts (FIG. 25).

Heat-Inactivation of *P. pastoris*.

The development of *P. pastoris* for whole recombinant yeast vaccine, as an alternative to *S. cerevisiae*, needed a set up of a protocol of heat-inactivation ensuring the death of vegetative yeast cells before their use. A recombinant *S. cerevisiae* previously tested in Phase IIb trial was heat-inactivated at 56° C. for 1 h (Haller A A et al., 2007, *Vaccine* 25: 1452-1463). As this protocol only partially inactivated *P. pastoris* GS115, the inventors evaluated a series of inactivation temperatures and time of treatment to achieve complete impairment of yeast growth. The inventors tested *P. pastoris* GS115, KM71, and SMD1168. Yeast survival after heat treatments was analyzed by culture both on plates and in liquid medium for 7 days at 30° C. The total loss of reproductive capacity was associated to the lack of metabolic activities, as assessed by methylene blue viability test. Complete growth impairment for the three strains was obtained following heat-inactivation at 58-60° C. for 45-60 minutes (Table 6). For the next experiments, the inventors used 60° C. for 45 minutes.

TABLE 6

Heat-inactivation of *P. pastoris* GS115, KM71 and SMD1168.

| First round Temperature (° C.) | Time (minutes) | GS115 inactivation |
|---|---|---|
| 43 | 30 | - |
| 56 | 60 | - |
| 60 | 30 | - |
| 65 | 30 | - |
| 65 | 40 | - |
| 66 | 15 | - |
| 68 | 5 | - |
| 68 | 10 | YES |
| 68 | 15 | YES |
| 95 | 5 | YES |

| Second round Temperature (° C.) | Time (minutes) | GS115 inactivation | KM71 inactivation |
|---|---|---|---|
| 56 | 60 | - | - |
| 56 | 120 | YES | - |
| 60 | 60 | YES | YES |
| 60 | 120 | YES | YES |
| 65 | 60 | YES | YES |
| 65 | 120 | YES | YES |

| Third round Temperature (° C.) | Time (minutes) | GS115 inacti-vation | KM71 inacti-vation | SMD1168 inacti-vation | Yeast viability (methylene blue) |
|---|---|---|---|---|---|
| 58 | 45 | YES | YES | YES | n.v. |
| 58 | 60 | YES | YES | YES | n.v. |
| 60 | 45 | YES | YES | YES | n.v. |
| 60 | 60 | YES | YES | YES | n.v. |

The hyphen (-) corresponds to incomplete inactivation and "n.v." to not-viable yeast. Results of these experiments are shown in FIG. 26.

Evaluation of the Immunogenicity and Efficacy of Whole Recombinant N-PbCS SMD1168 Yeast Vaccine in the *Plasmodium berghei*—C57Bl/6 Mouse Model.

To evaluate the immunogenicity and efficacy of whole recombinant SMD1168 *P. pastoris* expressing MV-N-based RNPs as carrier of PbCS antigen, the inventors used the C56Bl/6 mouse model of Pb infection, a highly stringent animal model for severe rodent malaria (Scheller L F et al., 1994, *Infect Immun* 62: 4844-4847). Immunizations were performed by five subcutaneous injections (once every week) of 30 YU heat-inactivated SMD1168 *P. pastoris* expressing N-PbCS in the absence of accessory adjuvants (FIG. 2). This dose contained 360 ng of N-PbCS corresponding to around 230 ng of N and 130 ng of PbCS antigens. The second group of mice was immunized similarly with 30 YU of recombinant SMD1168 expressing N only (diluted with wild-type SMD1168 yeast to adjust the amounts of N and of yeast material with respect to the N-PbCS group). The third group received 30 YU of wild-type (WT) SMD1168, and the fourth group was kept unvaccinated but housed in parallel (naive). Bleedings were performed every week during immunization and just before challenge (day 42) to determine antibody responses. All groups of mice were challenged at day 43 with 6,000 $GFP^+$ Pb sporozoites and parasitemia and mouse survival rate were monitored. $GFP^+$ Pb sporozoites provide the same growth rate and infectivity as the wild type parasite throughout the Pb life cycle (Ishino T et al., 2006, 59: 1175-1184), and were used to facilitate parasitemia determination by flow cytometry. To enlarge mouse sampling and validate results from the first experiment, an additional immunization study was performed following the protocol described above. In this second immunization round, a new group of 8 mice was added: the PbCS group that was immunized with PbCS recombinant yeast expressing the *Plasmodium* antigen in its monomeric form. Independently from the immunization round, data were comparable, showing the robustness of outputs despite two independent sporozoite and recombinant yeast preparations. Consequently, immunization groups from both rounds were pooled (FIG. 4 and FIG. 27).

Anti-N IgG antibodies became detectable after the third injection in mice immunized with N or N-PbCS yeasts and reached highest titers at day 42. The anti-N response at day 42 (FIG. 4A) was statistically comparable in both N and N-PbCS immunized groups, excluding immune interference between N and PbCS antigens in anti-N humoral response. All immunized mice showed anti-*P. pastoris* antibody responses (FIG. 27), while naive mice did not present anti-*P. pastoris* cross reacting antibody responses (data not shown). Interestingly, the two N-PbCS mice that were negative for anti-N antibodies (FIG. 4A) had anti-PbCS responses at $4\times10^4$ and $1.5\times10^5$ titers (FIGS. 4B and 4F). In the PbCS group, the anti-PbCS antibody response was at the limit of detection all over the follow up (data not shown), while in the N-PbCS group it was detected after 2-4 immunizations and still increased in half of the animals after the last injection (FIG. 4B). Median titer reached $3\times10^4$ at day 42 when immunization was completed (FIG. 4F). Comparison between PbCS and N-PbCS groups clearly shows that multimerization of the Plasmodium antigen on MV N RNPs rescued antigen specific antibody responses.

Two weeks after the last immunization, immunized mice were challenged with 6,000 $GFP^+$ Pb sporozoites and the parasitemia (proportion of parasite-containing RBCS) was determined at early time points during parasite exponential growth (FIG. 4C). From day 3 to 6 after challenge, the parasitemia was comparable in the N, PbCS and WT control groups where iRBC reduction was non statistically different from values of the naive group, while parasitemia was significantly reduced in the N-PbCS group (notably, around 4-fold at day 5 post-challenge; $p<0.05$ at days 4 and 5, and $p<0.005$ at day 6; Mann-Whitney nonparametric test). Comparison between parasitemia in the N-PbCS and PbCS groups shows again that multimerization of PbCS on RNPs made the difference. The inventors observed that mice dying early (day 7-14) presented clinical signs of experimental cerebral malaria, whereas after day 20 mice died as a consequence of hyper-parasitemia (up to 35-55% of iRBCs/RBCs at day 20, and 60-70% at day 25). The parasitemia at day 5 and the day of death showed a significant inverse correlation (Spearman test; $p<0.005$): a low parasitemia (0-0.2%) preferentially resulted in a late death, while a higher parasitemia (>0.2%) resulted in a more rapid death associated with experimental cerebral malaria (FIG. 4D). Immunization with N-PbCS yeasts increased survival since 10 out of 14 mice were still alive at day 22 post challenge, while most of the mice from PbCS, WT and naive groups died around day 11 (FIG. 4E). Surprisingly, the N group showed a comparable survival rate to the N-PbCS group, despite the complete absence of antibody cross-reactions between N and PbCS, and different impact of N and N-PbCS immunizations on parasitemia. In the N-PbCS group, mice with the highest anti-PbCS IgG levels had the most prolonged survival, although antibody titers were not predictive of early or late animal death outcome (Mann-Whitney nonparametric test).

As IgG subclasses mediate different immune effector functions depending on their structures (Nimmerjahn F, Ravetch J V, 2008, *Nat Rev Immunol* 8: 34-47), the inventors determined the IgG subclass responses to PbCS in N-PbCS immunized mice before challenge (FIG. 4F). There was no Th1 or Th2 polarization of the humoral immune response since the IgG1 response was statistically comparable to IgG2b, and the relevant difference between IgG1 and IgG2a ($p<0.05$) was compensated in the Th2/Th1 bias by the IgG2b response (Mann-Whitney nonparametric test). Remarkably, the detection of significant IgG1 and IgG2a/b humoral responses underlines the elicitation of both Th1 and Th2 cytokine environments after vaccination with the whole recombinant N-PbCS yeast in the absence of adjuvants.

In the present work, fusion of PbCS to MV-N resulted in antigen multimerization into RNP structures that were localized in the cytoplasm of recombinant yeasts. Injected subcutaneously in the absence of accessory adjuvants and at low antigen dose (130 ng PbCS per injection), the N-PbCS *P. pastoris* induced a significant delay in the emergence of parasitemia as well as prolonged survival of recipient C57Bl/6 mice following a stringent challenge consisting in the intradermal injection of a high number (6,000) of infectious Pb sporozoites. Comparison among N, PbCS and N-PbCS groups indicates that multimerization of PbCS on RNPs was necessary to significantly decrease parasitemia and increase survival in mice. But as far as survival is concerned, the N protein seems to contribute together with *Plasmodium* antigen multimerization to the outcome. Anti-PbCS IgG responses reflected unbiased contribution of Th1 and Th2 immune responses, indicating broad elicitation of the immune system in the absence of accessory adjuvants.

The inventors assumed that the CS proteins from Pb (infecting mice) and *P. falciparum* (infecting humans) shared conformational and functional properties, although they present around 60% divergent amino acids sequences (Plassmeyer M L et al., 2009, *J Biol Chem* 284: 26951-26963). To determine whether CS expression in *P. pastoris* depends on specific protein sequence, the inventors generated MV-N fusion proteins with equivalent CS domains from *P. falciparum* (strain 3D7; PfCS) and from PbCS. Full length N-PfCS (92.73 kDa) was produced in *P. pastoris* GS115 and KM71 at 97 ng/YU (data not shown), while N-PbCS (91.32 kDa) was not produced in GS115 or KM71 strains, and only at lower yield in SMD1168 strain (12 ng/YU). These data indicated that primary amino acid sequence determined the efficiency of N-CS fusion protein expression in *P. pastoris*. Yeast proteases are major actors in foreign protein degradation. As only general knowledge is available on protease targets essentially from *S. cerevisiae*, the outcome of the production system of the invention would not be predictable from the available prior knowledge. The better production yield observed for PfCS as compared to PbCS in *P. pastoris* was considered by the inventors to be favorable for developing a human vaccine relying on this strategy. The administration regimen was an important issue for whole inactivated yeast. In this study, the inventors showed that three injections at one-week interval were necessary to elicit detectable anti-CS antibody response in most mice. In preliminary experiments, the inventors observed that three injections at two-week interval (d0, d14, d28) did not induce anti-CS antibodies or parasitemia delay (data not shown). This might be due to the low expression level of N-PbCS in SMD1168 strain (12 ng/YU) or to the intrinsic feature of whole recombinant *P. pastoris*. Increasing antigen production yield by further selection of expressing clones was obviously required. However, frequent boosts might be needed to elicit robust long-term immune responses. Multiple doses with whole recombinant yeast were tested as administration protocols for therapeutic vaccination with myostatin (Zhang T et al., 2011, *Vaccine* 29: 8412-8416), K-Ras oncoprotein (Lu Y et al., 2004, *Cancer Res* 64: 5084-5088) or HCV NS3 and Core (GI-5005; Haller A A et al., 2007, *Vaccine* 25: 1452-1463). Notably in this last study, up to 13 weekly doses of whole recombinant yeast showed no yeast neutralization in mouse or toxicity in rabbit, and cellular immune responses increased in parallel with injection frequency (Haller A A et al., 2007, *Vaccine* 25: 1452-1463). However, for logistic and economic reasons, no more than three vaccine administrations can be scheduled for preventive immunization of infants living in areas of malaria endemicity.

In conclusion, the inventors provide *P. pastoris* yeast as an alternative vaccine production and delivery system to multimerize antigens of *Plasmodium*. PbCS was selected given the availability of the stringent C57Bl/6 mouse model of infection by Pb sporozoites, allowing the evaluation of vaccine efficacy in vivo. The CS antigen was multimerized by fusion to MV-N known to auto-assemble in yeast in large size RNPs. Expressed in *P. pastoris* SMD1168, the N-PbCS protein generated highly multimeric and heterogenic RNPs bearing the PbCS antigen on their surface. Electron microscopy and immunofluorescence analyses revealed the shape of these RNPs and their localization in peripheral cytoplasmic inclusions. Subcutaneous immunization of C57Bl/6 mice with heat-inactivated, whole *P. pastoris* expressing N-PbCS RNPs provided significant protection against intradermal challenge with a high dose of parasites. Thus, in the absence of accessory adjuvants, a very low amount of PbCS antigen expressed in whole unpurified yeast significantly decreased clinical damages associated with Pb infection in a highly stringent challenge model, providing a proof of concept of the intrinsic adjuvancy of this vaccine strategy.

Intrinsic Adjuvancy and Efficacy of the Whole Yeast-RNP Vaccine Platform.

The crucial step of the present study was to examine whether N maintains its ability to form RNPs upon fusion with another protein, for instance with PbCS. The inventors expressed the N-PbCS fusion protein in *P. pastoris* yeast and proved that indeed N was capable of forming RNPs upon fusion of PbCS C-terminal to its Ntail domain. Recombinant N-PbCS RNPs had a "herring-bone"-like structure similar to RNPs produced by N alone, and were localized in compact inclusions in the yeast cytoplasm. PbCS fusion to N resulted in a 70-fold decrease in expression level with respect to N alone, rendering N-PbCS yield to 12 ng/YU. Despite this reduction, the inventors demonstrated that in the absence of accessory adjuvant, whole recombinant yeast expressing these RNPs resulted in significant parasitemia delay and benefited on clinical outcome following immunization and challenge.

Recombinant RNPs represent the main antigenic component of the designed vaccine platform and can be regarded as a nanoparticulate subunit vaccine. In accordance with other studies showing the advantage of multimerized antigen delivery (Bachmann et al., 2010, *Nature,* 10, 787-796), RNPs proved a potent vector, which increased PbCS immunogenicity. Non-multimerized PbCS induced lower (by yeast lysate delivery) or none (by whole heat-inactivated yeast delivery) humoral responses, and in both cases immunizations with non-multimerized PbCS were not protective against *P. berghei* challenge. On the contrary, multimerized PbCS induced strong humoral responses and provided parasitemia delay or sterile protection depending on the dose and formulation. It is important to mention, that after heat-treatment the yeast cell wall became difficultly degradable by mechanical lysis, preventing analysis of RNPs in heat-inactivated yeast. However, beneficial effects of immunization with yeast carrying N-PbCS RNPs, but not PbCS in its monomeric state, provided indirect evidence that PbCS was indeed multimerized in yeast.

Immunogenicity of whole heat-inactivated *P. pastoris* yeast expressing N-PbCS RNPs was highlighted by strong antibody responses following immunization and infection delay upon challenge. Although the evaluated formulation/immunization protocol (5 weekly immunizations with 30 YU of heat-inactivated *P. pastoris* yeast expressing N-PbCS) was not sterilely protective against *P. berghei* infection, it significantly delayed parasitemia development, proving that PbCS-dependent parasite arrest has occurred during the liver infection stage. This effect was achieved with as little as 130 ng of PbCS equivalent in 30 YU of N-PbCS expressing yeast, which is a very low dose of antigens (e.g. 5 μg of RTS,S are used in mice per injection in combination with ASO1 adjuvant in GSK pre-clinical trials, containing 1 μg of the CS antigen). Moreover, immunization with N-PbCS expressing yeast significantly decreased incidence of cerebral malaria. This effect is highly valuable for the subsequent development of a human vaccine candidate, as cerebral malaria is a major cause of permanent consequences of malaria infection or deaths in humans. Susceptibility to cerebral malaria was shown to correlate with allergic inflammatory responses during infection (Macheri, 2012, *BBA,* 1822, 49-56). According to this notion, mechanisms responsible for cerebral malaria escape induced by vaccination with whole heat-inactivated yeast expressing N-PbCS RNPs have to be addressed. As mice immunized with N-expressing yeast also showed parasitemia decrease, although at a less extent than N-PbCS immunized mice, and cerebral malaria escape as well, N itself seems to have a non-specific beneficial effect on parasitemia and cerebral malaria escape, which has to be studied.

As the dose of RNPs delivered within whole yeast is limited by the maximal amount of yeast that can be administered to mice (30 YU) without causing irreversible inflammations at the infection site, delivery of higher doses of RNPs was performed by means of a yeast lysate formulation. Indeed, with increasing doses of non-adjuvanted yeast lysates (30, 150 and 300 YU) a clear dose-dependent effect was detected in parasitemia delay. In the group immunized with the highest dose of 300 YU N-PbCS yeast lysate, one animal out of six was parasite-free during all the follow up and developed no clinical symptoms of infection, indicating sterile protection. Mice immunized with 3 or 5 injections of 30 YU yeast lysate carrying N-PbCS showed higher rates of protection against cerebral malaria comparing to mice immunized with 150 YU and 300 YU. However, larger groups of mice are required for statistical analysis.

Removal of the yeast cell wall and delivery of RNPs within the yeast lysate also let the inventors evaluate the potential adjuvant effect of yeast internal components. Heat-inactivated yeast contains cell wall PAMPs (pathogen-associated molecular patterns) recognized as danger signals by cells of the immune system, which although may be modified to some extent upon heat-inactivation. On the contrary, the yeast lysate is substantially deprived of yeast surface PAMPs, but represents a formulation of yeast proteins and nucleic acids of foreign nature, which could be recognized as danger signals by mammalian cells. 30 YU of N-PbCS carrying yeast were evaluated in both whole heat-inactivated and non-adjuvanted lysed formulations. It appeared that yeast lysates induced slightly higher antibody responses against N and PbCS. Antibodies appeared after 2-3 immunizations with yeast lysates, while with heat-inactivated yeast it took 3-4 immunizations to launch the humoral response. Nevertheless, protective efficiency in decreasing parasite infection of N-PbCS RNPs in both delivery formulations was comparable, as at day 5 post challenge parasitemia was reduced by 4-fold in mice immunized with the heat-inactivated formulation and by 3.3-fold less in mice immunized with yeast lysate.

Both humoral and cellular responses are considered to play a role in CS-mediated protection against *P. falciparum* infection in humans (Kai et al., 2011, PLoS ONE; Kumar et al., 2006, Nature, 444, 937-940; Moorthy et al., 2008, Malaria Journal, 8, 312). As no T cell epitopes against PbCS have been identified in C57Bl/6 mice, which would allow performing an easy T cell assay, induction of cellular responses in the present study was sought for indirectly by isotyping IgG antibody responses. IgG isotype profiles are known to correlate with the establishment of Th1 and Th2 cytokine environments (IgG2b and IgG2a respectively) (Nimmerjahn et al., 2008, *Nature,* 8, 34-47). Moreover, to evaluate if experimental conditions could be ameliorated in order to induce sterile protection by immunization with N-PbCS RNPs, aluminum hydroxide gel (alum) adjuvant was added to the yeast lysate formulation. As alum possesses antibody-stimulating properties (Gupta et al., 2000, *Vaccine Adjuvants*), implication of anti-PbCS humoral responses in protection was evaluated.

A preliminary study on a small group of three mice showed no significant difference in protection provided by 30 YU of N-PbCS delivered in whole heat-inactivated yeast and alum-adjuvanted yeast lysates (data not shown). As anti-PbCS humoral responses as well as parasitemia decrease were previously shown to be dose dependent, a series of higher doses was evaluated in formulation with alum (50 YU, 100 YU and 150 YU). Interestingly, all the three doses administered three times bi-weekly produced comparable results: nearly 10-fold increase in anti-PbCS antibody titers (106) comparing to maximally obtained previously (2×105, 300 YU N-PbCS yeast lysate) and sterile protection in two out of six mice in each group. With regard to the overall high levels of antibody titers, individual levels of anti-PbCS antibodies in mice were not predictive of sterile protection. Consistent with other studies, the inventors showed that anti-PbCS antibodies played a limited role in protection against Plasmodium infection, as 50 YU of N-PbCS-carrying yeast lysates formulated with alum induced plateauing titers of anti-PbCS antibodies, which were unpredictive of protection.

While N-PbCS delivered within 30 YU of whole heat-inactivated yeast, non-adjuvanted or alum-adjuvanted yeast lysates provided similar level of parasitemia decrease irrespective of anti-PbCS antibody titers, the inventors have considered that further development of the whole heat-inactivated yeast formulation should be prioritized. Whole heat-inactivated yeast formulation is advantageous from the manufacturing and economical points of view, as preparation of yeast lysates could significantly increase the cost of the vaccine and limit its potential application in the developing world. Moreover, whole inactivated yeast offers the possibility of lyophilized transportation in the absence of cold-chain, and oral route of administration, which would have a great impact on facilitating vaccine distribution and administration. The use of hydrogel as an adjuvant for stimulating humoral responses is not advantageous with this vaccine platform, as adjuvant-free formulations were almost as efficient in stimulating antibody responses, which do not correlate with protection. With growing public inacceptance of vaccination due to societal intolerance to side effects of vaccines and their adjuvant components, which are often associated to these side effect problems, whole yeast RNP formulation represents an optimal vaccine strategy to pursue as it allows induction of antigen-specific immune responses in the absence of accessory adjuvants.

This study provided proof-of-concept of recombinant RNPs produced in whole heat-inactivated yeast as an efficient antigen delivery platform for preventive vaccines. However, regarding development of a malaria vaccine, it has to be further optimized. As protective efficacy of N-PbCS RNPs is dose dependent, optimizing N-PbCS expression in yeast is a key to a more efficient whole heat-inactivated vaccine formulation. Secondly, to improve the vaccine formulation, investigation of the underlying mechanisms of immunogenicity of whole yeast delivery of recombinant RNPs has to be pursued. It was demonstrated in a number of studies, that whole yeast cells are efficiently uptaken by dendritic cells, which results in efficient presentation of recombinantly expressed antigens within MHC class I and class II molecules and induction of CD4+ and CD8+ T cell responses. In the context of malaria, induction of T cell-mediated immunity seems to play a major role in protection. Interactions of the whole recombinant yeast with DCs, as the first step in induction of immune responses, has to be investigated. By comparing DC activation and mobility in the presence of purified N-PbCS RNPs, or delivered in yeast-lysate or whole heat-inactivated yeast, an optimal ratio in the antigen and whole yeast components could be established. In addition, to demonstrate more directly the induction of cellular responses, this platform has to be evaluated in the context of another antigen with defined T cell epitopes.

The invention claimed is:

1. Multimeric ribonucleoproteins (RNPs) having a quaternary structure containing at least 200 fusion proteins assembled with a cellular ribonucleic acid (RNA), wherein the fusion protein comprises a nucleoprotein (N) of a non-segmented negative-strand RNA virus of the Paramyxoviridae family fused directly or indirectly with a heterologous polypeptide carrying one or a plurality of epitopes and wherein the cellular RNA is transcribed from the genome of a cell.

2. The multimeric RNPs according to claim 1, wherein the non-segmented negative-strand RNA virus of the Paramyxoviridae family is a measles virus.

3. The multimeric RNPs according to claim 1, wherein the heterologous polypeptide is from a parasite.

4. The multimeric RNPs according to claim 1, wherein the heterologous polypeptide is fused to the C-terminus of the nucleoprotein (N).

5. The multimeric RNPs according to claim 1, which are high-molecular weight RNPs, assembling from 200 to 1000 fusion proteins obtained between a nucleoprotein (N) and a heterologous polypeptide.

6. A recombinant yeast comprising the RNPs of claim 1.

7. The recombinant yeast according to claim 6, which is prepared from a strain of *Pichia pastoris* or *Saccharomyces cerevisiae.*

8. An inactivated recombinant yeast, which results from heat-inactivation at 58-60° C. for 45-60 minutes of the recombinant yeast according to claim 6.

9. A yeast lysate, which is a lysate of the recombinant yeast according to claim 6.

10. An immunogenic composition comprising multimeric RNPs according to claim 1.

11. A subunit vaccine platform comprising multimeric RNPs according to claim 1.

12. A multivalent immunogenic composition comprising a mixture of recombinant yeasts according to claim 6 or lysates thereof, wherein in the mixture, at least two clones of recombinant yeasts or yeast lysates are present, one clone expressing a heterologous polypeptide that is different from the heterologous polypeptide of the other(s) clone(s).

13. A process for the preparation of multimeric RNPs having a quaternary structure containing at least 200 fusion proteins assembled with a cellular ribonucleic acid (RNA), wherein the fusion protein comprises a nucleoprotein (N) of a non-segmented negative-strand RNA virus of the Paramyxoviridae family fused directly or indirectly with a heterologous polypeptide carrying one or a plurality of epitopes and wherein the cellular RNA is transcribed from the genome of a cell, characterized in that it comprises the steps of:

(i) obtaining recombinant yeast according to claim 6 or lysates thereof, and (ii) recovering the multimeric RNPs from said yeast or yeast lysate.

14. A method of inducing a protective immune response against a heterologous polypeptide in a host, comprising administering an immunogenic composition comprising the RNPs of claim 1 to the host.

15. A method of inducing a protective immune response against a heterologous polypeptide in a host, comprising administering an immunogenic composition comprising recombinant yeast expressing the RNPs of claim 1 to the host.

16. The multimeric RNPs according to claim 2, wherein the measles virus is a Schwarz strain meales virus or a Moraten strain meales virus.

17. The multimeric RNPs according to claim 3, wherein the parasite is from a protozoan parasite of the genus *Plasmodium*.

18. The multimeric RNPs according to claim 3, wherein the parasite is from a virus of the Picornaviridiae family.

* * * * *

SEQUENCE LISTING

```
<160> NUMBER OF SEQ ID NOS: 44

<210> SEQ ID NO 1
<211> LENGTH: 1575
<212> TYPE: DNA
<213> ORGANISM: Artificial Sequence
<220> FEATURE:
<223> OTHER INFORMATION: Native nucleotide sequence of the
      polynucleotide encoding the nucleoprotein of Schwarz/Moraten MV

<400> SEQUENCE: 1

atggccacac ttttaaggag cttagcattg ttcaaaagaa acaaggacaa accacccatt      60

acatcaggat ccggtggagc catcagagga atcaaacaca ttattatagt accaatccct     120

ggagattcct caattaccac tcgatccaga cttctggacc ggttggtgag gttaattgga     180
```

```
aacccggatg tgagcgggcc caaactaaca ggggcactaa taggtatatt atccttattt    240

gtggagtctc caggtcaatt gattcagagg atcaccgatg accctgacgt tagcataagg    300

ctgttagagg ttgtccagag tgaccagtca caatctggcc ttaccttcgc atcaagaggt    360

accaacatgg aggatgaggc ggaccaatac ttttcacatg atgatccaat tagtagtgat    420

caatccaggt tcggatggtt cgggaacaag gaaatctcag atattgaagt gcaagaccct    480

gagggattca acatgattct gggtaccatc ctagcccaaa tttgggtctt gctcgcaaag    540

gcggttacgg ccccagacac ggcagctgat tcggagctaa gaaggtggat aaagtacacc    600

caacaaagaa gggtagttgg tgaatttaga ttggagagaa aatggttgga tgtggtgagg    660

aacaggattg ccgaggacct ctccttacgc cgattcatgg tcgctctaat cctggatatc    720

aagagaacac ccggaaacaa acccaggatt gctgaaatga tatgtgacat tgatacatat    780

atcgtagagg caggattagc cagttttatc ctgactatta agtttgggat agaaactatg    840

tatcctgctc ttggactgca tgaatttgct ggtgagttat ccacacttga gtccttgatg    900

aacctttacc agcaaatggg ggaaactgca ccctacatgg taatcctgga gaactcaatt    960

cagaacaagt tcagtgcagg atcataccct ctgctctgga gctatgccat gggagtagga   1020

gtggaacttg aaaactccat gggaggtttg aactttggcc gatcttactt tgatccagca   1080

tattttagat tagggcaaga gatggtaagg aggtcagctg gaaaggtcag ttccacattg   1140

gcatctgaac tcggtatcac tgccgaggat gcaaggcttg tttcagagat tgcaatgcat   1200

actactgagg acaagatcag tagagcggtt ggacccagac aagcccaagt atcatttcta   1260

cacggtgatc aaagtgagaa tgagctaccg agattggggg gcaaggaaga taggagggtc   1320

aaacagagtc gaggagaagc cagggagagc tacagagaaa ccgggcccag cagagcaagt   1380

gatgcgagag ctgcccatct tccaaccggc acacccctag acattgacac tgcaacggag   1440

tccagccaag atccgcagga cagtcgaagg tcagctgacg ccctgcttag gctgcaagcc   1500

atggcaggaa tctcggaaga acaaggctca gacacggaca cccctatagt gtacaatgac   1560

agaaatcttc tagac                                                     1575
```

```
<210> SEQ ID NO 2
<211> LENGTH: 1575
<212> TYPE: DNA
<213> ORGANISM: Artificial Sequence
<220> FEATURE:
<223> OTHER INFORMATION: Optimized nucleotide sequence of the
      polynucleotide encoding the nucleoprotein of Schwarz/Moraten MV

<400> SEQUENCE: 2
```

```
atggccacgt tattgagatc tttagccctt tttaagagga acaaggacaa acccccaatt     60

acaagtggtt ctggtggagc tattcgtggt attaagcaca ttattatcgt gcccattcca    120

ggggattcaa gtatcaccac ccgaagtaga ttgttggaca gattggtccg acttataggg    180

aacccagacg ttagtggacc caagctgacc ggggctctga tcggaatctt atctttgttc    240

gttgaatctc caggacagtt aatccaaagg attacagacg atccagacgt ctctattagg    300

cttctagagg ttgttcagtc tgaccagtct caatccggtc ttaccttcgc ttcaagaggt    360

accaatatgg aggacgaagc cgatcaatat ttctcacatg acgatcctat ctcctccgac    420

caatcaagat ttggttggtt cggaaacaaa gagatctctg acattgaggt tcaggaccca    480

gaaggattta acatgatact gggaactatc cttgcacaaa tctgggtgct gctggctaaa    540

gccgttactg ctccagacac cgctgctgat tccgaattac gaagatggat taaatacact    600
```

-continued

```
caacaacgta gagtagttgg tgaatttaga ttggagagaa agtggttgga tgttgtgaga    660

aacagaattg cagaagacct atcactgaga cgatttatgg tcgctcttat actggatatt    720

aagaggacac caggaaacaa gccaaggatt gcagaaatga tctgtgatat agatacttac    780

atcgttgagg ccgggttggc ttcctttatt ctaactataa aatttggtat cgagacaatg    840

tacccagcat tgggattgca tgagttcgcc ggagaactgt caacattgga gtcattgatg    900

aatctatacc agcaaatggg tgaaacagct ccatatatgg tcattctgga aaactccatt    960

caaaacaagt tttcagccgg ttcataccca ttattgtggt cttacgccat gggagtcggt   1020

gtagagctgg aaaactctat gggtggcctt aatttcggca gatcttattt tgatcccgct   1080

tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcaacggaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagat                                                    1575
```

```
<210> SEQ ID NO 3
<211> LENGTH: 525
<212> TYPE: PRT
<213> ORGANISM: Artificial Sequence
<220> FEATURE:
<223> OTHER INFORMATION: Amino acid sequence of the nucleoprotein of
      Schwarz/Moraten MV

<400> SEQUENCE: 3

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
```

```
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525
```

<210> SEQ ID NO 4
<211> LENGTH: 1575
<212> TYPE: DNA
<213> ORGANISM: Artificial Sequence
<220> FEATURE:
<223> OTHER INFORMATION: Native nucleotide sequence of the polynucleotide encoding the nucleoprotein of Rubeovax MV

<400> SEQUENCE: 4

```
atggccacac ttttaaggag cttagcattg ttcaaaagaa acaaggacaa accacccatt      60

acatcaggat ccggtggagc catcagagga atcaaacaca ttattatagt accaatccct     120
```

```
ggagattcct caattaccac tcgatccaga cttctggacc ggttggtcag gttaattgga    180
aacccggatg tgagcgggcc caaactaaca ggggcactaa taggtatatt atccttattt    240
gtggagtctc caggtcaatt gattcagagg atcaccgatg accctgacgt tagcataagg    300
ctgttagagg ttgtccagag tgaccagtca caatctggcc ttaccttcgc atcaagaggt    360
accaacatgg aggatgaggc ggaccaatac ttttcacatg atgatccaat tagtagtgat    420
caatccaggt tcggatggtt cgagaacaag gaaatctcag atattgaagt gcaagaccct    480
gagggattca acatgattct gggtaccatc ctagcccaaa tttgggtctt gctcgcaaag    540
gcggttacgg ccccagacac ggcagctgat tcggagctaa gaaggtggat aaagtacacc    600
caacaaagaa gggtggttgg tgaatttaga ttggagagaa aatggttgga tgtggtgagg    660
aacaggattg ccgaggacct ctccttacgc cgattcatgg tcgctctaat cctggatatc    720
aagagaacac ccggaaacaa acccaggatt gctgaaatga tatgtgacat tgatacatat    780
atcgtagagg caggattagc cagttttatc ctgactatta agtttgggat agaaactatg    840
tatcctgctc ttggactgca tgaatttgct ggtgagttat ccacacttga gtccttgatg    900
aacctttacc agcaaatggg ggaaactgca ccctacatgg taatcctgga gaactcaatt    960
cagaacaagt tcagtgcagg atcataccct ctgctctgga gctatgccat gggagtagga   1020
gtggaacttg aaaactccat gggaggtttg aactttggcc gatcttactt tgatccagca   1080
tattttagat tagggcaaga gatggtaagg aggtcagctg gaaaggtcag ttccacattg   1140
gcatctgaac tcggtatcac tgccgaggat gcaaggcttg tttcagagat tgcaatgcat   1200
actactgagg acaagatcag tagagcggtt ggacccagac aagcccaagt atcatttcta   1260
cacggtgatc aaagtgagaa tgagctaccg agattggggg gcaaggaaga taggagggtc   1320
aaacagagtc gaggagaagc cagggagagc tacagagaaa ccgggcccag cagagcaagt   1380
gatgcgagag ctgcccatct tccaaccggc acacccctag acattgacac tgcaacggag   1440
tccagccaag atccgcagga cagtcgaagg tcagctgacg ccctgcttag gctgcaagcc   1500
atggcaggaa tctcggaaga acaaggctca gacacggaca cccctatagt gtacaatgac   1560
agaaatcttc tagac                                                     1575
```

<210> SEQ ID NO 5
<211> LENGTH: 1575
<212> TYPE: DNA
<213> ORGANISM: Artificial Sequence
<220> FEATURE:
<223> OTHER INFORMATION: Optimized nucleotide sequence of the polynucleotide encoding the nucleoprotein of Rubeovax MV

<400> SEQUENCE: 5

```
atggccacgt tattgagatc tttagccctt tttaagagga acaaggacaa acccccaatt     60
acaagtggtt ctggtggagc tattcgtggt attaagcaca ttattatcgt gcccattcca    120
ggggattcaa gtatcaccac ccgaagtaga ttgttggaca gattggtccg acttataggg    180
aacccagacg ttagtggacc caagctgacc ggggctctga tcggaatctt atctttgttc    240
gttgaatctc caggacagtt aatccaaagg attacagacg atccagacgt ctctattagg    300
cttctagagg ttgttcagtc tgaccagtct caatccggtc ttaccttcgc ttcaagaggt    360
accaatatgg aggacgaagc cgatcaatat ttctcacatg acgatcctat ctcctccgac    420
caatcaagat ttggttggtt cgagaacaaa gagatctctg acattgaggt tcaggaccca    480
gaaggattta acatgatact gggaactatc cttgcacaaa tctgggtgct gctggctaaa    540
```

-continued

```
gccgttactg ctccagacac cgctgctgat tccgaattac gaagatggat taaatacact    600

caacaacgta gagtagttgg tgaatttaga ttggagagaa agtggttgga tgttgtgaga    660

aacagaattg cagaagacct atcactgaga cgatttatgg tcgctcttat actggatatt    720

aagaggacac caggaaacaa gccaaggatt gcagaaatga tctgtgatat agatacttac    780

atcgttgagg ccgggttggc ttcctttatt ctaactataa aatttggtat cgagacaatg    840

tacccagcat tgggattgca tgagttcgcc ggagaactgt caacattgga gtcattgatg    900

aatctatacc agcaaatggg tgaaacagct ccatatatgg tcattctgga aaactccatt    960

caaaacaagt tttcagccgg ttcataccca ttattgtggt cttacgccat gggagtcggt   1020

gtagagctgg aaaactctat gggtggcctt aatttcggca gatcttattt tgatcccgct   1080

tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcaacggaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagat                                                    1575
```

```
<210> SEQ ID NO 6
<211> LENGTH: 525
<212> TYPE: PRT
<213> ORGANISM: Artificial Sequence
<220> FEATURE:
<223> OTHER INFORMATION: Amino acid sequence of the nucleoprotein of
      Rubeovax MV

<400> SEQUENCE: 6

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
```

-continued

```
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525
```

<210> SEQ ID NO 7
<211> LENGTH: 1575
<212> TYPE: DNA
<213> ORGANISM: Artificial Sequence
<220> FEATURE:
<223> OTHER INFORMATION: Native nucleotide sequence of the polynucleotide encoding the nucleoprotein of AIK-C MV

<400> SEQUENCE: 7

-continued

```
atggccacac ttttaaggag cttagcattg ttcaaaagaa acaaggacaa accacccatt     60

acatcaggat ccggtggagc catcagagga atcaaacaca ttattatagt accaatccct    120

ggagattcct caattaccac tcgatccaga cttctggacc ggttggtcag gttaattgga    180

aacccggatg tgagcgggcc caaactaaca ggggcactaa taggtatatt atccttattt    240

gtggagtctc caggtcaatt gattcagagg atcaccgatg accctgacgt tagcataagg    300

ctgttagagg ttgtccagag tgaccagtca caatctggcc ttaccttcgc atcaagaggt    360

accaacatgg aggatgaggc ggacaaatac ttttcacatg atgatccaat tagtagtgat    420

caatccaggt tcggatggtt cgagaacaag gaaatctcag atattgaagt gcaagaccct    480

gagggattca acatgattct gggtaccatc ctagcccaaa tttgggtctt gctcgcaaag    540

gcggttacgg ccccagacac ggcagctgat tcggagctaa gaaggtggat aaagtacacc    600

caacaaagaa gggtagttgg tgaatttaga ttggagagaa aatggttgga tgtggtgagg    660

aacaggattg ccgaggacct ctccttacgc cgattcatgg tcgctctaat cctggatatc    720

aagagaacac ccggaaacaa acccaggatt gctgaaatga tatgtgacat tgatacatat    780

atcgtagagg caggattagc cagttttatc ctgactatta agtttgggat agaaactatg    840

tatcctgctc ttggactgca tgaatttgct ggtgagttat ccacacttga gtccttgatg    900

aacctttacc agcaaatggg ggaaactgca ccctacatgg taatcctgga gaactcaatt    960

cagaacaagt tcagtgcagg atcataccct ctgctctgga gctatgccat gggagtagga   1020

gtggaacttg aaaactccat gggaggtttg aactttggcc gatcttactt tgatccagca   1080

tattttagat tagggcaaga gatggtaagg aggtcagctg gaaaggtcag ttccacattg   1140

gcatctgaac tcggtatcac tgccgaggat gcaaggcttg tttcagagat tgcaatgcat   1200

actactgagg acaagatcag tagagcggtt ggacccagac aagcccaagt atcatttcta   1260

cacggtgatc aaagtgagaa tgagctaccg agattggggg gcaaggaaga taggagggtc   1320

aaacagagtc gaggagaagc cagggagagc tacagagaaa ccgggcccag cagagcaagt   1380

gatgcgagag ctgcccatct tccaaccggc acacccctag acattgacac tgcatcggag   1440

tccagccaag atccgcagga cagtcgaagg tcagctgacg ccctgcttag gctgcaagcc   1500

atggcaggaa tctcggaaga acaaggctca gacacggaca cccctatagt gtacaatgac   1560

agaaatcttc tagac                                                    1575
```

<210> SEQ ID NO 8
<211> LENGTH: 1575
<212> TYPE: DNA
<213> ORGANISM: Artificial Sequence
<220> FEATURE:
<223> OTHER INFORMATION: Optimized nucleotide sequence of the polynucleotide encoding the nucleoprotein of AIK-C MV

<400> SEQUENCE: 8

```
atggccacgt tattgagatc tttagccctt tttaagagga acaaggacaa acccccaatt     60

acaagtggtt ctggtggagc tattcgtggt attaagcaca ttattatcgt gcccattcca    120

ggggattcaa gtatcaccac ccgaagtaga ttgttggaca gattggtccg acttataggg    180

aacccagacg ttagtggacc caagctgacc ggggctctga tcggaatctt atctttgttc    240

gttgaatctc caggacagtt aatccaaagg attacagacg atccagacgt ctctattagg    300

cttctagagg ttgttcagtc tgaccagtct caatccggtc ttaccttcgc ttcaagaggt    360

accaatatgg aggacgaagc cgataagtat ttctcacatg acgatcctat ctcctccgac    420
```

-continued

```
caatcaagat ttggttggtt cgagaacaaa gagatctctg acattgaggt tcaggaccca    480

gaaggattta acatgatact gggaactatc cttgcacaaa tctgggtgct gctggctaaa    540

gccgttactg ctccagacac cgctgctgat tccgaattac gaagatggat taaatacact    600

caacaacgta gagtagttgg tgaatttaga ttggagagaa agtggttgga tgttgtgaga    660

aacagaattg cagaagacct atcactgaga cgatttatgg tcgctcttat actggatatt    720

aagaggacac caggaaacaa gccaaggatt gcagaaatga tctgtgatat agatacttac    780

atcgttgagg ccgggttggc ttcctttatt ctaactataa aatttggtat cgagacaatg    840

tacccagcat tgggattgca tgagttcgcc ggagaactgt caacattgga gtcattgatg    900

aatctatacc agcaaatggg tgaaacagct ccatatatgg tcattctgga aaactccatt    960

caaaacaagt tttcagccgg ttcataccca ttattgtggt cttacgccat gggagtcggt   1020

gtagagctgg aaaactctat gggtggcctt aatttcggca gatcttattt tgatcccgct   1080

tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcatctgaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagat                                                    1575
```

<210> SEQ ID NO 9
<211> LENGTH: 525
<212> TYPE: PRT
<213> ORGANISM: Artificial Sequence
<220> FEATURE:
<223> OTHER INFORMATION: Amino acid sequence of the nucleoprotein of AIK-C MV

<400> SEQUENCE: 9

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Lys Tyr Phe Ser His Asp Asp Pro Ile Ser Ser Asp Gln Ser Arg Phe
    130                 135                 140

Gly Trp Phe Glu Asn Lys Glu Ile Ser Asp Ile Glu Val Gln Asp Pro
```

```
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Ser Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525
```

<210> SEQ ID NO 10
<211> LENGTH: 1575
<212> TYPE: DNA
<213> ORGANISM: Artificial Sequence
<220> FEATURE:
<223> OTHER INFORMATION: Native nucleotide sequence of the
polynucleotide encoding the nucleoprotein of Zagreb MV

<400> SEQUENCE: 10
atggccacac ttttaaggag cttagcattg ttcaaaagaa acaaggacaa accacccatt 60
acatcaggat ccggtggagc catcagagga atcaaacaca ttattatagt accaatccct 120
ggagattcct caattaccac tcgatccaga cttctggacc ggttggtcag gttaattgga 180
aacccggatg tgagcgggcc caaactaaca ggggcactaa taggtatatt atccttattt 240
gtggagtctc caggtcaatt gattcagagg atcaccgatg accctgacgt tagcataagg 300
ctgttagagg ttgtccagag tgaccagtca caatctggcc ttaccttcgc atcaagaggt 360
accaacatgg aggatgaggc ggaccaatac ttttcacatg atgatccaat tagtagtgat 420
caatccaggt tcggatggtt cgagaacaag gaaatctcag atattgaagt gcaagaccct 480
gagggattca acatgattct gggtaccatc ctagctcaaa tttgggtctt gctcgcaaag 540
gcggttacgg ccccagacac ggcagctgat tcggagctaa gaaggtggat aaagtacacc 600
caacaaagaa gggtagttgg tgaatttaga ttggagagaa aatggttgga tgtggtgagg 660
aacaggattg ccgaggacct ctccttacgc cgattcatgg tcgctctaat cctggatatc 720
aagagaacac ccggaaacaa acccaggatt gctgaaatga tatgtgacat tgatacatat 780
atcgtagagg caggattagc cagttttatc ctgactatta agtttgggat agaaactatg 840
tatcctgctc ttggactgca tgaatttgct ggtgagttat ccacacttga gtccttgatg 900
aacctttacc agcaaatggg ggaaactgca ccctacatgg taatcctgga gaactcaatt 960
cagaacaagt tcagtgcagg atcataccct ctgctctgga gctatgccat gggagtagga 1020
gtggaacttg aaaactccat gggaggtttg aactttggcc gatcttactt tgatccagca 1080
tattttagat tagggcaaga gatggtaagg aggtcagctg gaaaggtcag ttccacattg 1140
gcatctgaac tcggtatcac tgccgaggat gcaaggcttg tttcagagat tgcaatgcat 1200
actactgagg acaagatcag tagagcggtt ggacccagac aagcccaagt atcatttcta 1260
cacggtgatc aaagtgagaa tgagctaccg agattggggg gcaaggaaga taggagggtc 1320
aaacagagtc gaggagaagc cagggagagc tacagagaaa ccgggcccag cagagcaagt 1380
gatgcgagag ctgcccatct tccaaccggc acacccctag acattgacac tgcatcggag 1440
tccagccaag atccgcagga cagtcgaagg tcagctgacg ccctgcttag gctgcaagcc 1500
atggcaggaa tctcggaaga acaaggctca gacacggaca cccctatagt gtacaatgac 1560
agaaatcttc tagac 1575

<210> SEQ ID NO 11
<211> LENGTH: 1575
<212> TYPE: DNA
<213> ORGANISM: Artificial Sequence
<220> FEATURE:
<223> OTHER INFORMATION: Optimized nucleotide sequence of the polynucleotide encoding the nucleoprotein of Zagreb MV or of the nucleoprotein of Edmonston MV

<400> SEQUENCE: 11
atggccacgt tattgagatc tttagccctt tttaagagga acaaggacaa acccccaatt 60
acaagtggtt ctggtggagc tattcgtggt attaagcaca ttattatcgt gcccattcca 120
ggggattcaa gtatcaccac ccgaagtaga ttgttggaca gattggtccg acttataggg 180
aacccagacg ttagtggacc caagctgacc ggggctctga tcggaatctt atctttgttc 240
gttgaatctc caggacagtt aatccaaagg attacagacg atccagacgt ctctattagg 300

-continued

```
cttctagagg ttgttcagtc tgaccagtct caatccggtc ttaccttcgc ttcaagaggt    360

accaatatgg aggacgaagc cgatcaatat ttctcacatg acgatcctat ctcctccgac    420

caatcaagat ttggttggtt cgagaacaaa gagatctctg acattgaggt tcaggaccca    480

gaaggattta acatgatact gggaactatc cttgcacaaa tctgggtgct gctggctaaa    540

gccgttactg ctccagacac cgctgctgat tccgaattac gaagatggat taaatacact    600

caacaacgta gagtagttgg tgaatttaga ttggagagaa agtggttgga tgttgtgaga    660

aacagaattg cagaagacct atcactgaga cgatttatgg tcgctcttat actggatatt    720

aagaggacac caggaaacaa gccaaggatt gcagaaatga tctgtgatat agatacttac    780

atcgttgagg ccgggttggc ttcctttatt ctaactataa aatttggtat cgagacaatg    840

tacccagcat tgggattgca tgagttcgcc ggagaactgt caacattgga gtcattgatg    900

aatctatacc agcaaatggg tgaaacagct ccatatatgg tcattctgga aaactccatt    960

caaaacaagt tttcagccgg ttcataccca ttattgtggt cttacgccat gggagtcggt   1020

gtagagctgg aaaactctat gggtggcctt aatttcggca gatcttattt tgatcccgct   1080

tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcatctgaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagat                                                    1575
```

<210> SEQ ID NO 12
<211> LENGTH: 525
<212> TYPE: PRT
<213> ORGANISM: Artificial Sequence
<220> FEATURE:
<223> OTHER INFORMATION: Amino acid sequence of the nucleoprotein of Zagreb MV or of the nucleoprotein of Edmonston MV

<400> SEQUENCE: 12

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125
```

-continued

```
Gln Tyr Phe Ser His Asp Asp Pro Ile Ser Ser Asp Gln Ser Arg Phe
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Ser Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525
```

<210> SEQ ID NO 13
<211> LENGTH: 1575
<212> TYPE: DNA

<213> ORGANISM: Artificial Sequence
<220> FEATURE:
<223> OTHER INFORMATION: Native nucleotide sequence of the polynucleotide encoding the nucleoprotein of Edmonston MV

<400> SEQUENCE: 13

```
atggccacac ttttaaggag cttagcattg ttcaaaagaa acaaggacaa accacccatt     60
acatcaggat ccggtggagc catcagagga atcaaacaca ttattatagt accaatccct    120
ggagattcct caattaccac tcgatccaga cttctggacc ggttggtcag gttaattgga    180
aacccggatg tgagcgggcc caaactaaca ggggcactaa taggtatatt atccttattt    240
gtggagtctc caggtcaatt gattcagagg atcaccgatg accctgacgt tagcataagg    300
ctgttagagg ttgtccagag tgaccagtca caatctggcc ttaccttcgc atcaagaggt    360
accaacatgg aggatgaggc ggaccaatac ttttcacatg atgatccaat tagtagtgat    420
caatccaggt tcggatggtt cgagaacaag gaaatctcag atattgaagt gcaagaccct    480
gagggattca acatgattct gggtaccatc ctagcccaaa tttgggtctt gctcgcaaag    540
gcggttacgg ccccagacac ggcagctgat tcggagctaa gaaggtggat aaagtacacc    600
caacaaagaa gggtagttgg tgaatttaga ttggagagaa aatggttgga tgtggtgagg    660
aacaggattg ccgaggacct ctccttacgc cgattcatgg tcgctctaat cctggatatc    720
aagagaacac ccggaaacaa acccaggatt gctgaaatga tatgtgacat tgatacatat    780
atcgtagagg caggattagc cagttttatc ctgactatta agtttgggat agaaactatg    840
tatcctgctc ttggactgca tgaatttgct ggtgagttat ccacacttga gtccttgatg    900
aacctttacc agcaaatggg ggaaactgca ccctacatgg taatcctgga gaactcaatt    960
cagaacaagt tcagtgcagg atcataccct ctgctctgga gctatgccat gggagtagga   1020
gtggaacttg aaaactccat gggaggtttg aactttggcc gatcttactt tgatccagca   1080
tattttagat tagggcaaga gatggtaagg aggtcagctg gaaaggtcag ttccacattg   1140
gcatctgaac tcggtatcac tgccgaggat gcaaggcttg tttcagagat tgcaatgcat   1200
actactgagg acaagatcag tagagcggtt ggacccagac aagcccaagt atcatttcta   1260
cacggtgatc aaagtgagaa tgagctaccg agattggggg gcaaggaaga taggagggtc   1320
aaacagagtc gaggagaagc cagggagagc tacagagaaa ccgggcccag cagagcaagt   1380
gatgcgagag ctgcccatct tccaaccggc acacccctag acattgacac tgcatcggag   1440
tccagccaag atccgcagga cagtcgaagg tcagctgacg ccctgcttag gctgcaagcc   1500
atggcaggaa tctcggaaga acaaggctca gacacggaca cccctatagt gtacaatgac   1560
agaaatcttc tagac                                                    1575
```

<210> SEQ ID NO 14
<211> LENGTH: 909
<212> TYPE: DNA
<213> ORGANISM: Artificial Sequence
<220> FEATURE:
<223> OTHER INFORMATION: Native nucleotide sequence of the polynucleotide encoding the CS polypeptide of P. berghei

<400> SEQUENCE: 14

```
agcatccaag cccaaaggaa cttaaacgag ctatgttaca atgaaggaaa tgataataaa     60
ttgtatcacg tgcttaactc taagaatgga aaaatataca atcgaaatac agtcaacaga    120
ttacttgccg atgctcccga aggaaaaaaa aatgagaaaa aaaacgaaaa aatagagcgt    180
aataataaat tgaaacaacc accaccacca ccaaacccaa atgacccacc accaccaaac    240
```

```
ccaaatgacc caccaccacc aaacccaaat gacccaccac caccaaaccc aaatgaccca    300

ccaccaccaa acgcaaatga cccaccacca ccaaacgcaa atgacccagc accaccaaac    360

gcaaatgacc cagcaccacc aaacgcaaat gacccagcac caccaaacgc aaatgaccca    420

gcaccaccaa acgcaaatga cccaccacca ccaaacccaa atgacccagc accaccaaac    480

gcaaatgacc caccaccacc aaacccaaat gacccagcac caccacaagg aaataacaat    540

ccacaaccac agccacggcc gcagccacaa ccacagccac agccacaacc acagccacag    600

ccacaaccac agccacgacc acagccacaa ccacagccag gtggtaataa caataacaaa    660

aataataata atgacgattc ttatatccca agcgcggaaa aaatactaga atttgttaaa    720

cagatcaggg atagtatcac agaggaatgg tctcaatgta acgtaacatg tggttctggt    780

ataagagtta gaaaacgaaa aggttcaaat aagaaagcag aagatttgac cttagaagat    840

attgatactg aaatttgtaa aatggataaa tgttcaagta tatttaatat tgtaagcaat    900

tcatagtag                                                            909
```

<210> SEQ ID NO 15
<211> LENGTH: 909
<212> TYPE: DNA
<213> ORGANISM: Artificial Sequence
<220> FEATURE:
<223> OTHER INFORMATION: Optimized nucleotide sequence of the polynucleotide encoding the CS polypeptide of P. berghei

<400> SEQUENCE: 15

```
tccatccagg cccagagaaa cttgaacgaa ctttgctaca acgaaggaaa cgacaacaaa     60

ctttaccacg tcttgaactc taagaatggt aaaatctaca acagaaacac agttaacaga    120

ttgcttgctg atgccccaga aggaaagaaa aatgagaaga aaaacgaaaa gatcgagaga    180

aacaataagt tgaaacaacc tcctccacct ccaaatccaa acgatcctcc acctccaaat    240

cctaacgacc cacctccacc taaccctaat gacccacctc cacctaatcc taacgaccct    300

ccacctccaa atgctaatga cccacctcct ccaaatgcaa acgacccagc tcctccaaat    360

gccaacgatc ctgcacctcc aaatgctaac gacccagccc ctccaaatgc aaacgatcct    420

gcccctccaa atgccaatga tccacctcca cctaatccaa atgacccagc accaccaaat    480

gccaatgatc ctcctccacc taacccaaac gatcctgctc ctccacaggg taacaataac    540

cctcaaccac agcctagacc acaacctcag cctcagcctc agccacaacc acaaccacaa    600

cctcagccac aacctagacc acagcctcaa ccacagcctg gtggaaataa taataacaaa    660

aacaacaaca acgatgactc ttatattcca tccgccgaaa agatccttga gtttgtcaag    720

caaatcagag actcaatcac cgaagagtgg agtcaatgta atgttacttg cggttctgga    780

attagagtca gaaagagaaa aggttctaac aagaaagctg aagatttgac tcttgaggat    840

atcgacacag agatttgtaa gatggataag tgctcaagta ttttcaacat tgtcagtaac    900

tcatagtag                                                            909
```

<210> SEQ ID NO 16
<211> LENGTH: 301
<212> TYPE: PRT
<213> ORGANISM: Artificial Sequence
<220> FEATURE:
<223> OTHER INFORMATION: Amino acid sequence of the CS polypeptide of P. berghei

<400> SEQUENCE: 16

-continued

```
Ser Ile Gln Ala Gln Arg Asn Leu Asn Glu Leu Cys Tyr Asn Glu Gly
1               5                   10                  15

Asn Asp Asn Lys Leu Tyr His Val Leu Asn Ser Lys Asn Gly Lys Ile
            20                  25                  30

Tyr Asn Arg Asn Thr Val Asn Arg Leu Leu Ala Asp Ala Pro Glu Gly
        35                  40                  45

Lys Lys Asn Glu Lys Lys Asn Glu Lys Ile Glu Arg Asn Asn Lys Leu
    50                  55                  60

Lys Gln Pro Pro Pro Pro Pro Asn Pro Asn Asp Pro Pro Pro Pro Asn
65                  70                  75                  80

Pro Asn Asp Pro Pro Pro Pro Asn Pro Asn Asp Pro Pro Pro Pro Asn
                85                  90                  95

Pro Asn Asp Pro Pro Pro Pro Asn Ala Asn Asp Pro Pro Pro Pro Asn
            100                 105                 110

Ala Asn Asp Pro Ala Pro Pro Asn Ala Asn Asp Pro Ala Pro Pro Asn
        115                 120                 125

Ala Asn Asp Pro Ala Pro Pro Asn Ala Asn Asp Pro Ala Pro Pro Asn
    130                 135                 140

Ala Asn Asp Pro Pro Pro Pro Asn Pro Asn Asp Pro Ala Pro Pro Asn
145                 150                 155                 160

Ala Asn Asp Pro Pro Pro Pro Asn Pro Asn Asp Pro Ala Pro Pro Gln
                165                 170                 175

Gly Asn Asn Asn Pro Gln Pro Gln Pro Arg Pro Gln Pro Gln Pro Gln
            180                 185                 190

Pro Gln Pro Gln Pro Gln Pro Gln Pro Gln Pro Gln Pro Arg Pro Gln
        195                 200                 205

Pro Gln Pro Gln Pro Gly Gly Asn Asn Asn Asn Lys Asn Asn Asn Asn
    210                 215                 220

Asp Asp Ser Tyr Ile Pro Ser Ala Glu Lys Ile Leu Glu Phe Val Lys
225                 230                 235                 240

Gln Ile Arg Asp Ser Ile Thr Glu Glu Trp Ser Gln Cys Asn Val Thr
                245                 250                 255

Cys Gly Ser Gly Ile Arg Val Arg Lys Arg Lys Gly Ser Asn Lys Lys
            260                 265                 270

Ala Glu Asp Leu Thr Leu Glu Asp Ile Asp Thr Glu Ile Cys Lys Met
        275                 280                 285

Asp Lys Cys Ser Ser Ile Phe Asn Ile Val Ser Asn Ser
    290                 295                 300


<210> SEQ ID NO 17
<211> LENGTH: 951
<212> TYPE: DNA
<213> ORGANISM: Artificial Sequence
<220> FEATURE:
<223> OTHER INFORMATION: Native nucleotide sequence of the
      polynucleotide encoding the CS polypeptide of P. falciparum

<400> SEQUENCE: 17

ggatccagca gcaacacgcg tgttctgaac gaactgaact acgataacgc tggtaccaat      60

ctgtacaacg aactggaaat gaactactac ggtaaacagg aaaactggta cagcctgaaa     120

aaaaacagca gatctctagg cgaaaacgac gacggcaaca acaacaacgg tgataacggt     180

cgcgaaggta aagacgaaga caaacgcgac ggcaacaacg aagacaacga aaaacttcgc     240

aaaccgaaac acaaaaaact taagcagcca ggggatggta atccagatcc gaacgcgaat     300

ccgaacgtag acccgaacgc aaacccgaac gtagacccga acgcaaaccc gaacgtagac     360
```

-continued

```
ccgaacgcga atccgaacgc gaaccctaac gcgaacccga acgcgaaccc gaacgcgaac    420

ccgaacgcga acccgaacgc gaacccgaac gcgaacccga acgcgaaccc gaacgcgaac    480

ccgaacgcga acccgaacgc gaacccgaac gcgaacccga acgcgaaccc gaacgcgaac    540

ccgaacgcga acccgaacgc gaacccgaac gcgaacccga acgcgaaccc gaacgcgaac    600

ccgaacgcga acccgaacaa aaacaatcag ggtaatggcc agggtcacaa tatgccaaat    660

gacccaaacc gaaatgtaga tgaaaatgct aatgccaaca atgctgtaaa aaataataat    720

aacgaagaac caagtgataa gcacatagaa caatatttaa agaaaataca aaattctctt    780

tcaactgaat ggtccccatg tagtgtaact tgcggcaacg gtattcaggt gcgcatcaag    840

ccgggctctg ctaacaaacc taaggacgaa ctggattacg aaaacgatat cgaaaaaaag    900

atctgtaaga tggaaaagtg ttcctctgta ttcaacgtag ttaactcttc g             951
```

<210> SEQ ID NO 18
<211> LENGTH: 957
<212> TYPE: DNA
<213> ORGANISM: Artificial Sequence
<220> FEATURE:
<223> OTHER INFORMATION: Optimized nucleotide sequence of the polynucleotide encoding the CS polypeptide of P. falciparum

<400> SEQUENCE: 18

```
ggcagttctt ctaacactcg tgttctaaat gagttgaatt atgacaacgc aggaactaat     60

ttgtacaatg agctggagat gaattactac ggtaagcagg agaactggta ttctttgaaa    120

aagaatagta gatctctggg agaaaatgac gacgggaata ataacaatgg agataatggt    180

agagaaggta aagatgaaga taagagggat ggtaacaacg aagacaatga aaagcttcgt    240

aagccaaaac acaaaaagct taagcaacca ggtgatggta acccagatcc taatgctaac    300

ccaaacgtag accctaacgc aaatcccaac gtggatccaa atgccaatcc taacgtagat    360

cccaacgcaa accctaacgc aaatcctaat gctaatccca atgctaatcc aaacgcaaac    420

cctaatgcaa accccaatgc taacccaaat gctaacccaa acgccaaccc taatgctaac    480

cctaacgcca accctaacgc taatcctaac gcaaacccaa atgccaatcc aaacgccaat    540

cctaacgcta accctaatgc caaccctaac gccaatccaa acgctaatcc aaacgctaac    600

ccaaatgcaa atcctaacaa gaacaaccaa ggtaatggtc agggccataa catgccaaat    660

gatcctaatc gtaatgtcga tgaaaacgca aatgcaaata atgccgttaa aaacaacaac    720

aacgaagaac cttcagataa acacattgaa cagtacctta agaaaattca aaattccttg    780

tctacggaat ggtccccatg ctctgtcact tgtggtaatg gcatacaagt gagaattaag    840

cctggttctg caaacaaacc aaaagacgaa cttgattatg aaaacgatat cgaaaagaag    900

atttgcaaaa tggagaaatg ttcttcagta ttcaacgtgg ttaatagttc ctaatag       957
```

<210> SEQ ID NO 19
<211> LENGTH: 317
<212> TYPE: PRT
<213> ORGANISM: Artificial Sequence
<220> FEATURE:
<223> OTHER INFORMATION: Amino acid sequence of the CS polypeptide of P. falciparum

<400> SEQUENCE: 19

```
Gly Ser Ser Ser Asn Thr Arg Val Leu Asn Glu Leu Asn Tyr Asp Asn
1               5                   10                  15

Ala Gly Thr Asn Leu Tyr Asn Glu Leu Glu Met Asn Tyr Tyr Gly Lys
```

```
            20                  25                  30

Gln Glu Asn Trp Tyr Ser Leu Lys Lys Asn Ser Arg Ser Leu Gly Glu
        35                  40                  45

Asn Asp Asp Gly Asn Asn Asn Asn Gly Asp Asn Gly Arg Glu Gly Lys
    50                  55                  60

Asp Glu Asp Lys Arg Asp Gly Asn Asn Glu Asp Asn Glu Lys Leu Arg
65                  70                  75                  80

Lys Pro Lys His Lys Lys Leu Lys Gln Pro Gly Asp Gly Asn Pro Asp
                85                  90                  95

Pro Asn Ala Asn Pro Asn Val Asp Pro Asn Ala Asn Pro Asn Val Asp
            100                 105                 110

Pro Asn Ala Asn Pro Asn Val Asp Pro Asn Ala Asn Pro Asn Ala Asn
        115                 120                 125

Pro Asn Ala Asn Pro Asn Ala Asn Pro Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Lys Asn
        195                 200                 205

Asn Gln Gly Asn Gly Gln Gly His Asn Met Pro Asn Asp Pro Asn Arg
    210                 215                 220

Asn Val Asp Glu Asn Ala Asn Ala Asn Asn Ala Val Lys Asn Asn Asn
225                 230                 235                 240

Asn Glu Glu Pro Ser Asp Lys His Ile Glu Gln Tyr Leu Lys Lys Ile
                245                 250                 255

Gln Asn Ser Leu Ser Thr Glu Trp Ser Pro Cys Ser Val Thr Cys Gly
            260                 265                 270

Asn Gly Ile Gln Val Arg Ile Lys Pro Gly Ser Ala Asn Lys Pro Lys
        275                 280                 285

Asp Glu Leu Asp Tyr Glu Asn Asp Ile Glu Lys Lys Ile Cys Lys Met
    290                 295                 300

Glu Lys Cys Ser Ser Val Phe Asn Val Val Asn Ser Ser
305                 310                 315


<210> SEQ ID NO 20
<211> LENGTH: 897
<212> TYPE: DNA
<213> ORGANISM: Artificial Sequence
<220> FEATURE:
<223> OTHER INFORMATION: Native nucleotide sequence of the
      polynucleotide encoding the VP1 protein from Enterovirus 71

<400> SEQUENCE: 20

ggagataggg tggcagatgt aattgaaagc tccataggag atagcgtgag cagagccctc      60

actcacgctc taccagcacc cacaggtcag aacacacagg tgagcagtca tcgactggat     120

acgggcaagg ttccagcact ccaagctgct gaaattggag catcatcaaa tgctagtgac     180

gagagtatga ttgagacacg ctgtgtcctc aactcgcaca gtacagcaga gaccactctt     240

gatagtttct tcagcagggc gggattagtt ggagagatag atctccctct tgagggcaca     300

actaacccaa atggttatgc caactgggac atagatataa caggttacgc gcaaatgcgt     360
```

-continued agaaaggtag agctcttcac ctacatgcgc tttgatgcag agttcacttt tgttgcgtgt 420
acacctaccg ggaagttgt tccacaactg ctccaatata tgtttgtgcc acctggagcc 480
ccaaagccag attctaggga atcccttgca tggcaaaccg ccactaaccc ctcagttttt 540
gtcaagctgt cagaccctcc agcacaggtt tcagtgccat tcatgtcacc tgcgagtgct 600
tatcaatggt tttatgacgg atatcccacg ttcggagaac acaaacagga gaaagatctt 660
gaatatgggg catgtcctaa taacatgatg ggcacgttct cagtgcggac tgtagggtcc 720
tccaagtcca agtaccctct agtgattagg atttacatga gaatgaagca cgtcagggcg 780
tggatacctc gcccgatgcg taaccagaac tacctattca aagccaatcc aaattatgct 840
ggcaactccg ttaagccaac tggtgccagt cgcacagcga tcaccactct ttgatga 897

<210> SEQ ID NO 21
<211> LENGTH: 897
<212> TYPE: DNA
<213> ORGANISM: Artificial Sequence
<220> FEATURE:
<223> OTHER INFORMATION: Optimized nucleotide sequence of the polynucleotide encoding the VP1 protein from Enterovirus 71

<400> SEQUENCE: 21
ggagatagag tcgccgatgt tattgagtct tccattggag attcagttag tagagccttg 60
acacacgcct tgccagcccc aaccggacaa aacactcagg tttcttccca tagattggat 120
acaggaaagg tccctgctct tcaagctgcc gagattggtg cctcaagtaa cgcatctgac 180
gaatccatga tcgagactag atgtgttttg aattcacaca gtacagctga aactacattg 240
gattcatttt tcagtagagc cggtcttgtt ggagagattg acttgccact tgaaggtacc 300
actaacccta atggatacgc caactgggat attgacatca ctggttatgc acagatgaga 360
agaaaagttg agttgtttac ctacatgaga ttcgatgcag aattcacttt cgttgcttgc 420
acaccaaccg gagaggttgt ccctcaattg cttcagtata tgtttgttcc acctggtgct 480
ccaaagcctg attctagaga atccttggct tggcaaactg ccacaaatcc atccgttttt 540
gtcaaacttt cagacccacc tgctcaagtt tctgtcccat tcatgtcacc tgcaagtgct 600
taccagtggt tttacgatgg ttatccaact ttcggagaac ataagcagga gaaagacttg 660
gaatatggtg cttgtcctaa caatatgatg ggaacatttt ctgttagaac cgtcggttct 720
tccaagtcca agtacccatt ggttattaga atctatatga gaatgaagca cgtcagagca 780
tggatcccaa gacctatgag aaaccaaaat taccttttca aagctaaccc taattatgca 840
ggaaactcag tcaagcctac aggagcatca agaaccgcca tcacaacact ttagtaa 897

<210> SEQ ID NO 22
<211> LENGTH: 297
<212> TYPE: PRT
<213> ORGANISM: Artificial Sequence
<220> FEATURE:
<223> OTHER INFORMATION: Amino acid sequence of the VP1 protein from Enterovirus 71

<400> SEQUENCE: 22

Gly Asp Arg Val Ala Asp Val Ile Glu Ser Ser Ile Gly Asp Ser Val
1               5                   10                  15

Ser Arg Ala Leu Thr His Ala Leu Pro Ala Pro Thr Gly Gln Asn Thr
            20                  25                  30

Gln Val Ser Ser His Arg Leu Asp Thr Gly Lys Val Pro Ala Leu Gln
        35                  40                  45

-continued

```
Ala Ala Glu Ile Gly Ala Ser Ser Asn Ala Ser Asp Glu Ser Met Ile
    50                  55                  60

Glu Thr Arg Cys Val Leu Asn Ser His Ser Thr Ala Glu Thr Thr Leu
65                  70                  75                  80

Asp Ser Phe Phe Ser Arg Ala Gly Leu Val Gly Glu Ile Asp Leu Pro
                85                  90                  95

Leu Glu Gly Thr Thr Asn Pro Asn Gly Tyr Ala Asn Trp Asp Ile Asp
            100                 105                 110

Ile Thr Gly Tyr Ala Gln Met Arg Arg Lys Val Glu Leu Phe Thr Tyr
        115                 120                 125

Met Arg Phe Asp Ala Glu Phe Thr Phe Val Ala Cys Thr Pro Thr Gly
    130                 135                 140

Glu Val Val Pro Gln Leu Leu Gln Tyr Met Phe Val Pro Pro Gly Ala
145                 150                 155                 160

Pro Lys Pro Asp Ser Arg Glu Ser Leu Ala Trp Gln Thr Ala Thr Asn
                165                 170                 175

Pro Ser Val Phe Val Lys Leu Ser Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Lys Gln Glu Lys Asp Leu Glu Tyr Gly Ala
    210                 215                 220

Cys Pro Asn Asn Met Met Gly Thr Phe Ser Val Arg Thr Val Gly Ser
225                 230                 235                 240

Ser Lys Ser Lys Tyr Pro Leu Val Ile Arg Ile Tyr Met Arg Met Lys
                245                 250                 255

His Val Arg Ala Trp Ile Pro Arg Pro Met Arg Asn Gln Asn Tyr Leu
            260                 265                 270

Phe Lys Ala Asn Pro Asn Tyr Ala Gly Asn Ser Val Lys Pro Thr Gly
        275                 280                 285

Ala Ser Arg Thr Ala Ile Thr Thr Leu
    290                 295
```

<210> SEQ ID NO 23
<211> LENGTH: 390
<212> TYPE: DNA
<213> ORGANISM: Artificial Sequence
<220> FEATURE:
<223> OTHER INFORMATION: Native nucleotide sequence of the polynucleotide encoding the avidin protein

<400> SEQUENCE: 23

```
gccagaaagt gctcgctgac tgggaaatgg accaacgatc tgggctccaa catgaccatc     60

ggggctgtga acagcagagg tgaattcaca ggcacctaca tcacagccgt aacagccaca    120

tcaaatgaga tcaaagagtc accactgcat gggacacaaa acaccatcaa caagaggacc    180

cagcccacct ttggcttcac cgtcaattgg aagttttcag agtccaccac tgtcttcacg    240

ggccagtgct tcatagacag gaatgggaag gaggtcctga agaccatgtg gctgctgcgg    300

tcaagtgtta atgacattgg tgatgactgg aaagctacca gggtcggcat caacatcttc    360

actcgcctgc gcacacagaa ggagtagtag                                      390
```

<210> SEQ ID NO 24
<211> LENGTH: 389
<212> TYPE: DNA
<213> ORGANISM: Artificial Sequence
<220> FEATURE:

-continued

<223> OTHER INFORMATION: Optimized nucleotide sequence of the polynucleotide encoding the avidin protein

<400> SEQUENCE: 24

```
ctagaaaatg ttcacttact ggaaaatgga caaatgacct tggttcaaat atgacaatcg     60

gtgctgttaa tagtcgtggt gaattcactg gaacttacat tactgctgtt acagccacct    120

ctaacgaaat caaggagtcc ccattgcatg gtactcaaaa cactattaac aagagaaccc    180

agcctacttt tggattcaca gttaattgga agttctcaga aagtactaca gtctttactg    240

gtcaatgttt cattgataga aacggaaagg aggttcttaa aactatgtgg ttgcttagat    300

cttccgtcaa tgacatcgga gatgactgga aggcaaccag agtcggtatt aacattttca    360

caagattgag aacccagaag gagtagtaa                                      389
```

<210> SEQ ID NO 25
<211> LENGTH: 128
<212> TYPE: PRT
<213> ORGANISM: Artificial Sequence
<220> FEATURE:
<223> OTHER INFORMATION: Amino acid sequence of the avidin protein

<400> SEQUENCE: 25

```
Ala Arg Lys Cys Ser Leu Thr Gly Lys Trp Thr Asn Asp Leu Gly Ser
1               5                   10                  15

Asn Met Thr Ile Gly Ala Val Asn Ser Arg Gly Glu Phe Thr Gly Thr
            20                  25                  30

Tyr Ile Thr Ala Val Thr Ala Thr Ser Asn Glu Ile Lys Glu Ser Pro
        35                  40                  45

Leu His Gly Thr Gln Asn Thr Ile Asn Lys Arg Thr Gln Pro Thr Phe
    50                  55                  60

Gly Phe Thr Val Asn Trp Lys Phe Ser Glu Ser Thr Thr Val Phe Thr
65                  70                  75                  80

Gly Gln Cys Phe Ile Asp Arg Asn Gly Lys Glu Val Leu Lys Thr Met
                85                  90                  95

Trp Leu Leu Arg Ser Ser Val Asn Asp Ile Gly Asp Asp Trp Lys Ala
            100                 105                 110

Thr Arg Val Gly Ile Asn Ile Phe Thr Arg Leu Arg Thr Gln Lys Glu
        115                 120                 125
```

<210> SEQ ID NO 26
<211> LENGTH: 21
<212> TYPE: DNA
<213> ORGANISM: Artificial Sequence
<220> FEATURE:
<223> OTHER INFORMATION: Nucleotide sequence of the peptide linker used in the N-PbCS, N-VP1 and N-Avidin fusion proteins

<400> SEQUENCE: 26

```
ggcgccgcgg gagcaggtgc a                                               21
```

<210> SEQ ID NO 27
<211> LENGTH: 7
<212> TYPE: PRT
<213> ORGANISM: Artificial Sequence
<220> FEATURE:
<223> OTHER INFORMATION: Amino acid sequence of the peptide linker used in the N-PbCS, N-VP1 and N-Avidin fusion proteins

<400> SEQUENCE: 27

```
Gly Ala Ala Gly Ala Gly Ala
1               5
```

<210> SEQ ID NO 28
<211> LENGTH: 18
<212> TYPE: DNA
<213> ORGANISM: Artificial Sequence
<220> FEATURE:
<223> OTHER INFORMATION: Nucleotide sequence of the peptide linker used in the N-PfCS fusion protein

<400> SEQUENCE: 28
ggcgcaggag caggagct 18

<210> SEQ ID NO 29
<211> LENGTH: 6
<212> TYPE: PRT
<213> ORGANISM: Artificial Sequence
<220> FEATURE:
<223> OTHER INFORMATION: Amino acid sequence of the peptide linker used in the N-PfCS fusion protein

<400> SEQUENCE: 29

Gly Ala Gly Ala Gly Ala
1 5

<210> SEQ ID NO 30
<211> LENGTH: 2505
<212> TYPE: DNA
<213> ORGANISM: Artificial Sequence
<220> FEATURE:
<223> OTHER INFORMATION: Native nucleotide sequence of the polynucleotide encoding the N-PbCS fusion protein (the nucleoprotein N is obtained from the Schwarz strain) including the nucleotide sequence encoding the peptide linker disclosed as sequence SEQ ID No: 26

<400> SEQUENCE: 30
atggccacac ttttaaggag cttagcattg ttcaaaagaa acaaggacaa accacccatt 60
acatcaggat ccggtggagc catcagagga atcaaacaca ttattatagt accaatccct 120
ggagattcct caattaccac tcgatccaga cttctggacc ggttggtgag gttaattgga 180
aacccggatg tgagcgggcc caaactaaca ggggcactaa taggtatatt atccttattt 240
gtggagtctc caggtcaatt gattcagagg atcaccgatg accctgacgt tagcataagg 300
ctgttagagg ttgtccagag tgaccagtca caatctggcc ttaccttcgc atcaagaggt 360
accaacatgg aggatgaggc ggaccaatac ttttcacatg atgatccaat tagtagtgat 420
caatccaggt tcggatggtt cgggaacaag gaaatctcag atattgaagt gcaagaccct 480
gagggattca acatgattct gggtaccatc ctagcccaaa tttgggtctt gctcgcaaag 540
gcggttacgg ccccagacac ggcagctgat tcggagctaa gaaggtggat aaagtacacc 600
caacaaagaa gggtagttgg tgaatttaga ttggagagaa aatggttgga tgtggtgagg 660
aacaggattg ccgaggacct ctccttacgc cgattcatgg tcgctctaat cctggatatc 720
aagagaacac ccggaaacaa acccaggatt gctgaaatga tatgtgacat tgatacatat 780
atcgtagagg caggattagc cagttttatc ctgactatta agtttgggat agaaactatg 840
tatcctgctc ttggactgca tgaatttgct ggtgagttat ccacacttga gtccttgatg 900
aacctttacc agcaaatggg ggaaactgca ccctacatgg taatcctgga gaactcaatt 960
cagaacaagt tcagtgcagg atcataccct ctgctctgga gctatgccat gggagtagga 1020
gtggaacttg aaaactccat gggaggtttg aactttggcc gatcttactt tgatccagca 1080
tattttagat tagggcaaga gatggtaagg aggtcagctg gaaaggtcag ttccacattg 1140
gcatctgaac tcggtatcac tgccgaggat gcaaggcttg tttcagagat tgcaatgcat 1200
actactgagg acaagatcag tagagcggtt ggacccagac aagcccaagt atcatttcta 1260
cacggtgatc aaagtgagaa tgagctaccg agattggggg gcaaggaaga taggagggtc 1320
aaacagagtc gaggagaagc cagggagagc tacagagaaa ccgggcccag cagagcaagt 1380
gatgcgagag ctgcccatct tccaaccggc acacccctag acattgacac tgcaacggag 1440
tccagccaag atccgcagga cagtcgaagg tcagctgacg ccctgcttag gctgcaagcc 1500
atggcaggaa tctcggaaga acaaggctca gacacggaca cccctatagt gtacaatgac 1560
agaaatcttc tagacggcgc cgcgggagca ggtgcaagca tccaagccca aaggaactta 1620
aacgagctat gttacaatga aggaaatgat aataaattgt atcacgtgct taactctaag 1680
aatggaaaaa tatacaatcg aaatacagtc aacagattac ttgccgatgc tcccgaagga 1740
aaaaaaaatg agaaaaaaaa cgaaaaaata gagcgtaata ataaattgaa acaaccacca 1800
ccaccaccaa acccaaatga cccaccacca ccaaacccaa atgacccacc accaccaaac 1860
ccaaatgacc caccaccacc aaacccaaat gacccaccac caccaaacgc aaatgaccca 1920
ccaccaccaa acgcaaatga cccagcacca ccaaacgcaa atgacccagc accaccaaac 1980
gcaaatgacc cagcaccacc aaacgcaaat gacccagcac caccaaacgc aaatgaccca 2040
ccaccaccaa acccaaatga cccagcacca ccaaacgcaa atgacccacc accaccaaac 2100
ccaaatgacc cagcaccacc acaaggaaat aacaatccac aaccacagcc acggccgcag 2160
ccacaaccac agccacagcc acaaccacag ccacagccac aaccacagcc acgaccacag 2220
ccacaaccac agccaggtgg taataacaat aacaaaaata ataataatga cgattcttat 2280
atcccaagcg cggaaaaaat actagaattt gttaaacaga tcagggatag tatcacagag 2340
gaatggtctc aatgtaacgt aacatgtggt tctggtataa gagttagaaa acgaaaaggt 2400
tcaaataaga aagcagaaga tttgacctta gaagatattg atactgaaat ttgtaaaatg 2460
gataaatgtt caagtatatt taatattgta agcaattcat agtag 2505

<210> SEQ ID NO 31
<211> LENGTH: 2505
<212> TYPE: DNA
<213> ORGANISM: Artificial Sequence
<220> FEATURE:
<223> OTHER INFORMATION: Optimized nucleotide sequence of the polynucleotide encoding the N-PbCS fusion protein (the nucleoprotein N is obtained from the Schwarz strain)including the nucleotide sequence encoding the peptide linker disclosed as sequence SEQ ID No: 26

<400> SEQUENCE: 31
atggccacgt tattgagatc tttagccctt tttaagagga acaaggacaa acccccaatt 60
acaagtggtt ctggtggagc tattcgtggt attaagcaca ttattatcgt gcccattcca 120
ggggattcaa gtatcaccac ccgaagtaga ttgttggaca gattggtccg acttataggg 180
aacccagacg ttagtggacc caagctgacc ggggctctga tcggaatctt atctttgttc 240
gttgaatctc caggacagtt aatccaaagg attacagacg atccagacgt ctctattagg 300
cttctagagg ttgttcagtc tgaccagtct caatccggtc ttaccttcgc ttcaagaggt 360
accaatatgg aggacgaagc cgatcaatat ttctcacatg acgatcctat ctcctccgac 420
caatcaagat ttggttggtt cggaaacaaa gagatctctg acattgaggt tcaggaccca 480
gaaggattta acatgatact gggaactatc cttgcacaaa tctgggtgct gctggctaaa 540

-continued

```
gccgttactg ctccagacac cgctgctgat tccgaattac gaagatggat taaatacact    600

caacaacgta gagtagttgg tgaatttaga ttggagagaa agtggttgga tgttgtgaga    660

aacagaattg cagaagacct atcactgaga cgatttatgg tcgctcttat actggatatt    720

aagaggacac caggaaacaa gccaaggatt gcagaaatga tctgtgatat agatacttac    780

atcgttgagg ccgggttggc ttcctttatt ctaactataa aatttggtat cgagacaatg    840

tacccagcat tgggattgca tgagttcgcc ggagaactgt caacattgga gtcattgatg    900

aatctatacc agcaaatggg tgaaacagct ccatatatgg tcattctgga aaactccatt    960

caaaacaagt tttcagccgg ttcataccca ttattgtggt cttacgccat gggagtcggt   1020

gtagagctgg aaaactctat gggtggcctt aatttcggca gatcttattt tgatcccgct   1080

tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcaacggaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagatggcgc cgcgggagca ggtgcatcca tccaggccca gagaaacttg   1620

aacgaacttt gctacaacga aggaaacgac aacaaacttt accacgtctt gaactctaag   1680

aatggtaaaa tctacaacag aaacacagtt aacagattgc ttgctgatgc cccagaagga   1740

aagaaaaatg agaagaaaaa cgaaaagatc gagagaaaca ataagttgaa acaacctcct   1800

ccacctccaa atccaaacga tcctccacct ccaaatccta acgacccacc tccacctaac   1860

cctaatgacc cacctccacc taatcctaac gaccctccac ctccaaatgc taatgaccca   1920

cctcctccaa atgcaaacga cccagctcct ccaaatgcca acgatcctgc acctccaaat   1980

gctaacgacc cagcccctcc aaatgcaaac gatcctgccc ctccaaatgc caatgatcca   2040

cctccaccta atccaaatga cccagcacca ccaaatgcca atgatcctcc tccacctaac   2100

ccaaacgatc ctgctcctcc acagggtaac aataaccctc aaccacagcc tagaccacaa   2160

cctcagcctc agcctcagcc acaaccacaa ccacaacctc agccacaacc tagaccacag   2220

cctcaaccac agcctggtgg aaataataat aacaaaaaca acaacaacga tgactcttat   2280

attccatccg ccgaaaagat ccttgagttt gtcaagcaaa tcagagactc aatcaccgaa   2340

gagtggagtc aatgtaatgt tacttgcggt tctggaatta gagtcagaaa gagaaaaggt   2400

tctaacaaga aagctgaaga tttgactctt gaggatatcg acacagagat ttgtaagatg   2460

gataagtgct caagtatttt caacattgtc agtaactcat agtag                   2505
```

<210> SEQ ID NO 32
<211> LENGTH: 833
<212> TYPE: PRT
<213> ORGANISM: Artificial Sequence
<220> FEATURE:
<223> OTHER INFORMATION: Amino acid sequence of the polynucleotide encoding the N-PbCS fusion protein (the nucleoprotein N is obtained from the Schwarz strain) including the amino acid sequence of the peptide linker disclosed as sequence SEQ ID No: 27

<400> SEQUENCE: 32

-continued

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
```

-continued

```
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp Gly Ala Ala
        515                 520                 525

Gly Ala Gly Ala Ser Ile Gln Ala Gln Arg Asn Leu Asn Glu Leu Cys
    530                 535                 540

Tyr Asn Glu Gly Asn Asp Asn Lys Leu Tyr His Val Leu Asn Ser Lys
545                 550                 555                 560

Asn Gly Lys Ile Tyr Asn Arg Asn Thr Val Asn Arg Leu Leu Ala Asp
                565                 570                 575

Ala Pro Glu Gly Lys Lys Asn Glu Lys Lys Asn Glu Lys Ile Glu Arg
            580                 585                 590

Asn Asn Lys Leu Lys Gln Pro Pro Pro Pro Pro Asn Pro Asn Asp Pro
        595                 600                 605

Pro Pro Pro Asn Pro Asn Asp Pro Pro Pro Pro Asn Pro Asn Asp Pro
    610                 615                 620

Pro Pro Pro Asn Pro Asn Asp Pro Pro Pro Pro Asn Ala Asn Asp Pro
625                 630                 635                 640

Pro Pro Pro Asn Ala Asn Asp Pro Ala Pro Pro Asn Ala Asn Asp Pro
                645                 650                 655

Ala Pro Pro Asn Ala Asn Asp Pro Ala Pro Pro Asn Ala Asn Asp Pro
            660                 665                 670

Ala Pro Pro Asn Ala Asn Asp Pro Pro Pro Pro Asn Pro Asn Asp Pro
        675                 680                 685

Ala Pro Pro Asn Ala Asn Asp Pro Pro Pro Pro Asn Pro Asn Asp Pro
    690                 695                 700

Ala Pro Pro Gln Gly Asn Asn Asn Pro Gln Pro Gln Pro Arg Pro Gln
705                 710                 715                 720

Pro Gln Pro Gln Pro Gln Pro Gln Pro Gln Pro Gln Pro Gln Pro Gln
                725                 730                 735

Pro Arg Pro Gln Pro Gln Pro Gln Pro Gly Gly Asn Asn Asn Asn Lys
            740                 745                 750

Asn Asn Asn Asn Asp Asp Ser Tyr Ile Pro Ser Ala Glu Lys Ile Leu
        755                 760                 765

Glu Phe Val Lys Gln Ile Arg Asp Ser Ile Thr Glu Glu Trp Ser Gln
    770                 775                 780

Cys Asn Val Thr Cys Gly Ser Gly Ile Arg Val Arg Lys Arg Lys Gly
785                 790                 795                 800

Ser Asn Lys Lys Ala Glu Asp Leu Thr Leu Glu Asp Ile Asp Thr Glu
                805                 810                 815

Ile Cys Lys Met Asp Lys Cys Ser Ser Ile Phe Asn Ile Val Ser Asn
            820                 825                 830

Ser
```

<210> SEQ ID NO 33
<211> LENGTH: 2544
<212> TYPE: DNA
<213> ORGANISM: Artificial Sequence
<220> FEATURE:
<223> OTHER INFORMATION: Native nucleotide sequence of the polynucleotide encoding the N-PfCS fusion protein (the nucleoprotein N is obtained from the Schwarz strain) including the nucleotide sequence encoding the peptide linker disclosed as sequence SEQ ID No: 28

<400> SEQUENCE: 33

```
atggccacac ttttaaggag cttagcattg ttcaaaagaa acaaggacaa accacccatt     60
acatcaggat ccggtggagc catcagagga atcaaacaca ttattatagt accaatccct    120
ggagattcct caattaccac tcgatccaga cttctggacc ggttggtgag gttaattgga    180
aacccggatg tgagcgggcc caaactaaca ggggcactaa taggtatatt atccttattt    240
gtggagtctc caggtcaatt gattcagagg atcaccgatg accctgacgt tagcataagg    300
ctgttagagg ttgtccagag tgaccagtca caatctggcc ttaccttcgc atcaagaggt    360
accaacatgg aggatgaggc ggaccaatac ttttcacatg atgatccaat tagtagtgat    420
caatccaggt tcggatggtt cgggaacaag gaaatctcag atattgaagt gcaagaccct    480
gagggattca acatgattct gggtaccatc ctagcccaaa tttgggtctt gctcgcaaag    540
gcggttacgg ccccagacac ggcagctgat tcggagctaa gaaggtggat aaagtacacc    600
caacaaagaa gggtagttgg tgaatttaga ttggagagaa aatggttgga tgtggtgagg    660
aacaggattg ccgaggacct ctccttacgc cgattcatgg tcgctctaat cctggatatc    720
aagagaacac ccggaaacaa acccaggatt gctgaaatga tatgtgacat tgatacatat    780
atcgtagagg caggattagc cagttttatc ctgactatta agtttgggat agaaactatg    840
tatcctgctc ttggactgca tgaatttgct ggtgagttat ccacacttga gtccttgatg    900
aacctttacc agcaaatggg ggaaactgca ccctacatgg taatcctgga gaactcaatt    960
cagaacaagt tcagtgcagg atcataccct ctgctctgga gctatgccat gggagtagga   1020
gtggaacttg aaaactccat gggaggtttg aactttggcc gatcttactt tgatccagca   1080
tattttagat tagggcaaga gatggtaagg aggtcagctg gaaaggtcag ttccacattg   1140
gcatctgaac tcggtatcac tgccgaggat gcaaggcttg tttcagagat tgcaatgcat   1200
actactgagg acaagatcag tagagcggtt ggacccagac aagcccaagt atcatttcta   1260
cacggtgatc aaagtgagaa tgagctaccg agattggggg gcaaggaaga taggagggtc   1320
aaacagagtc gaggagaagc cagggagagc tacagagaaa ccgggcccag cagagcaagt   1380
gatgcgagag ctgcccatct tccaaccggc acacccctag acattgacac tgcaacggag   1440
tccagccaag atccgcagga cagtcgaagg tcagctgacg ccctgcttag gctgcaagcc   1500
atggcaggaa tctcggaaga acaaggctca gacacggaca cccctatagt gtacaatgac   1560
agaaatcttc tagacggcgc aggagcagga gctggatcca gcagcaacac gcgtgttctg   1620
aacgaactga actacgataa cgctggtacc aatctgtaca acgaactgga aatgaactac   1680
tacggtaaac aggaaaactg gtacagcctg aaaaaaaaca gcagatctct aggcgaaaac   1740
gacgacggca acaacaacaa cggtgataac ggtcgcgaag gtaaagacga agacaaacgc   1800
gacggcaaca acgaagacaa cgaaaaactt cgcaaaccga aacacaaaaa acttaagcag   1860
ccaggggatg gtaatccaga tccgaacgcg aatccgaacg tagacccgaa cgcaaacccg   1920
aacgtagacc cgaacgcaaa cccgaacgta gacccgaacg cgaatccgaa cgcgaaccct   1980
```

aacgcgaacc cgaacgcgaa cccgaacgcg aacccgaacg cgaacccgaa cgcgaacccg 2040
aacgcgaacc cgaacgcgaa cccgaacgcg aacccgaacg cgaacccgaa cgcgaacccg 2100
aacgcgaacc cgaacgcgaa cccgaacgcg aacccgaacg cgaacccgaa cgcgaacccg 2160
aacgcgaacc cgaacgcgaa cccgaacgcg aacccgaacg cgaacccgaa caaaaacaat 2220
cagggtaatg gccagggtca caatatgcca aatgacccaa accgaaatgt agatgaaaat 2280
gctaatgcca acaatgctgt aaaaaataat aataacgaag aaccaagtga taagcacata 2340
gaacaatatt taaagaaaat acaaaattct ctttcaactg aatggtcccc atgtagtgta 2400
acttgcggca acggtattca ggtgcgcatc aagccgggct ctgctaacaa acctaaggac 2460
gaactggatt acgaaaacga tatcgaaaaa aagatctgta agatggaaaa gtgttcctct 2520
gtattcaacg tagttaactc ttcg 2544

<210> SEQ ID NO 34
<211> LENGTH: 2550
<212> TYPE: DNA
<213> ORGANISM: Artificial Sequence
<220> FEATURE:
<223> OTHER INFORMATION: Optimized nucleotide sequence of the polynucleotide encoding the N-PfCS fusion protein (the nucleoprotein N is obtained from the Schwarz strain) including the nucleotide sequence encoding the peptide linker disclosed as sequence SEQ ID No: 28

<400> SEQUENCE: 34
atggccacgt tattgagatc tttagccctt tttaagagga acaaggacaa acccccaatt 60
acaagtggtt ctggtggagc tattcgtggt attaagcaca ttattatcgt gcccattcca 120
ggggattcaa gtatcaccac ccgaagtaga ttgttggaca gattggtccg acttataggg 180
aacccagacg ttagtggacc caagctgacc ggggctctga tcggaatctt atctttgttc 240
gttgaatctc caggacagtt aatccaaagg attacagacg atccagacgt ctctattagg 300
cttctagagg ttgttcagtc tgaccagtct caatccggtc ttaccttcgc ttcaagaggt 360
accaatatgg aggacgaagc cgatcaatat ttctcacatg acgatcctat ctcctccgac 420
caatcaagat ttggttggtt cggaaacaaa gagatctctg acattgaggt tcaggaccca 480
gaaggattta acatgatact gggaactatc cttgcacaaa tctgggtgct gctggctaaa 540
gccgttactg ctccagacac cgctgctgat tccgaattac gaagatggat taaatacact 600
caacaacgta gagtagttgg tgaatttaga ttggagagaa agtggttgga tgttgtgaga 660
aacagaattg cagaagacct atcactgaga cgatttatgg tcgctcttat actggatatt 720
aagaggacac caggaaacaa gccaaggatt gcagaaatga tctgtgatat agatacttac 780
atcgttgagg ccgggttggc ttcctttatt ctaactataa aatttggtat cgagacaatg 840
tacccagcat tgggattgca tgagttcgcc ggagaactgt caacattgga gtcattgatg 900
aatctatacc agcaaatggg tgaaacagct ccatatatgg tcattctgga aaactccatt 960
caaaacaagt tttcagccgg ttcataccca ttattgtggt cttacgccat gggagtcggt 1020
gtagagctgg aaaactctat gggtggcctt aatttcggca gatcttattt tgatcccgct 1080
tattttagac tgggccaaga gatggtcaga cgttctgccg gaaaggtttc tagtactttg 1140
gctagtgaac taggtataac tgctgaggac gctagattgg tttctgaaat agctatgcac 1200
actactgaag ataagatcag tagggccgtt ggccctaggc aagctcaggt gtccttctta 1260
catggtgatc aatccgagaa tgagttgcct cgattgggag gcaaagagga ccgtagagtt 1320

```
aaacaatcta gaggagaggc acgtgaatct tacagagaga ccggtccatc ccgagcttct   1380

gatgcacgag ccgctcatct tcctaccggt acacctttag acattgatac ggcaacggaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagatggcgc aggagcagga gctggcagtt cttctaacac tcgtgttcta   1620

aatgagttga attatgacaa cgcaggaact aatttgtaca atgagctgga gatgaattac   1680

tacggtaagc aggagaactg gtattctttg aaaaagaata gtagatctct gggagaaaat   1740

gacgacggga ataataacaa tggagataat ggtagagaag gtaaagatga agataagagg   1800

gatggtaaca acgaagacaa tgaaaagctt cgtaagccaa aacacaaaaa gcttaagcaa   1860

ccaggtgatg gtaacccaga tcctaatgct aacccaaacg tagaccctaa cgcaaatccc   1920

aacgtggatc caaatgccaa tcctaacgta gatcccaacg caaaccctaa cgcaaatcct   1980

aatgctaatc ccaatgctaa tccaaacgca aaccctaatg caaaccccaa tgctaaccca   2040

aatgctaacc caaacgccaa ccctaatgct aaccctaacg ccaaccctaa cgctaatcct   2100

aacgcaaacc caaatgccaa tccaaacgcc aatcctaacg ctaaccctaa tgccaaccct   2160

aacgccaatc caaacgctaa tccaaacgct aacccaaatg caaatcctaa caagaacaac   2220

caaggtaatg gtcagggcca taacatgcca aatgatccta atcgtaatgt cgatgaaaac   2280

gcaaatgcaa ataatgccgt taaaaacaac aacaacgaag aaccttcaga taaacacatt   2340

gaacagtacc ttaagaaaat tcaaaattcc ttgtctacgg aatggtcccc atgctctgtc   2400

acttgtggta atggcataca agtgagaatt aagcctggtt ctgcaaacaa accaaaagac   2460

gaacttgatt atgaaaacga tatcgaaaag aagatttgca aaatggagaa atgttcttca   2520

gtattcaacg tggttaatag ttcctaatag                                    2550
```

<210> SEQ ID NO 35
<211> LENGTH: 848
<212> TYPE: PRT
<213> ORGANISM: Artificial Sequence
<220> FEATURE:
<223> OTHER INFORMATION: Amino acid sequence of the polynucleotide encoding the N-PfCS fusion protein (the nucleoprotein N is obtained from the Schwarz strain) including the amino acid sequence of the peptide linker disclosed as sequence SEQ ID No: 29

<400> SEQUENCE: 35

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125
```

-continued

```
Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp Gly Ala Gly
        515                 520                 525

Ala Gly Ala Gly Ser Ser Ser Asn Thr Arg Val Leu Asn Glu Leu Asn
    530                 535                 540

Tyr Asp Asn Ala Gly Thr Asn Leu Tyr Asn Glu Leu Glu Met Asn Tyr
```

```
545                 550                 555                 560

Tyr Gly Lys Gln Glu Asn Trp Tyr Ser Leu Lys Lys Asn Ser Arg Ser
                565                 570                 575

Leu Gly Glu Asn Asp Asp Gly Asn Asn Asn Asn Gly Asp Asn Gly Arg
            580                 585                 590

Glu Gly Lys Asp Glu Asp Lys Arg Asp Gly Asn Asn Glu Asp Asn Glu
        595                 600                 605

Lys Leu Arg Lys Pro Lys His Lys Lys Leu Lys Gln Pro Gly Asp Gly
    610                 615                 620

Asn Pro Asp Pro Asn Ala Asn Pro Asn Val Asp Pro Asn Ala Asn Pro
625                 630                 635                 640

Asn Val Asp Pro Asn Ala Asn Pro Asn Val Asp Pro Asn Ala Asn Pro
                645                 650                 655

Asn Ala Asn Pro Asn Ala Asn Pro Asn Ala Asn Pro Asn Ala Asn Pro
            660                 665                 670

Asn Ala Asn Pro Asn Ala Asn Pro Asn Ala Asn Pro Asn Ala Asn Pro
        675                 680                 685

Asn Ala Asn Pro Asn Ala Asn Pro Asn Ala Asn Pro Asn Ala Asn Pro
    690                 695                 700

Asn Ala Asn Pro Asn Ala Asn Pro Asn Ala Asn Pro Asn Ala Asn Pro
705                 710                 715                 720

Asn Ala Asn Pro Asn Ala Asn Pro Asn Ala Asn Pro Asn Ala Asn Pro
                725                 730                 735

Asn Lys Asn Asn Gln Gly Asn Gly Gln Gly His Asn Met Pro Asn Asp
            740                 745                 750

Pro Asn Arg Asn Val Asp Glu Asn Ala Asn Ala Asn Asn Ala Val Lys
        755                 760                 765

Asn Asn Asn Asn Glu Glu Pro Ser Asp Lys His Ile Glu Gln Tyr Leu
    770                 775                 780

Lys Lys Ile Gln Asn Ser Leu Ser Thr Glu Trp Ser Pro Cys Ser Val
785                 790                 795                 800

Thr Cys Gly Asn Gly Ile Gln Val Arg Ile Lys Pro Gly Ser Ala Asn
                805                 810                 815

Lys Pro Lys Asp Glu Leu Asp Tyr Glu Asn Asp Ile Glu Lys Lys Ile
            820                 825                 830

Cys Lys Met Glu Lys Cys Ser Ser Val Phe Asn Val Val Asn Ser Ser
        835                 840                 845


<210> SEQ ID NO 36
<211> LENGTH: 2493
<212> TYPE: DNA
<213> ORGANISM: Artificial Sequence
<220> FEATURE:
<223> OTHER INFORMATION: Native nucleotide sequence of the
      polynucleotide encoding the N-VP1 fusion protein (the
      nucleoprotein N is obtained from the Schwarz strain) including the
      nucleotide sequence encoding the peptide linker disclosed as
      sequence SEQ ID No: 26

<400> SEQUENCE: 36

atggccacac ttttaaggag cttagcattg ttcaaaagaa acaaggacaa accacccatt      60

acatcaggat ccggtggagc catcagagga atcaaacaca ttattatagt accaatccct     120

ggagattcct caattaccac tcgatccaga cttctggacc ggttggtgag gttaattgga     180

aacccggatg tgagcgggcc caaactaaca ggggcactaa taggtatatt atccttattt     240

gtggagtctc caggtcaatt gattcagagg atcaccgatg accctgacgt tagcataagg     300
```

ctgttagagg ttgtccagag tgaccagtca caatctggcc ttaccttcgc atcaagaggt 360
accaacatgg aggatgaggc ggaccaatac ttttcacatg atgatccaat tagtagtgat 420
caatccaggt tcggatggtt cgggaacaag gaaatctcag atattgaagt gcaagaccct 480
gagggattca acatgattct gggtaccatc ctagcccaaa tttgggtctt gctcgcaaag 540
gcggttacgg ccccagacac ggcagctgat tcggagctaa gaaggtggat aaagtacacc 600
caacaaagaa gggtagttgg tgaatttaga ttggagagaa aatggttgga tgtggtgagg 660
aacaggattg ccgaggacct ctccttacgc cgattcatgg tcgctctaat cctggatatc 720
aagagaacac ccggaaacaa acccaggatt gctgaaatga tatgtgacat tgatacatat 780
atcgtagagg caggattagc cagttttatc ctgactatta agtttgggat agaaactatg 840
tatcctgctc ttggactgca tgaatttgct ggtgagttat ccacacttga gtccttgatg 900
aacctttacc agcaaatggg ggaaactgca ccctacatgg taatcctgga gaactcaatt 960
cagaacaagt tcagtgcagg atcataccct ctgctctgga gctatgccat gggagtagga 1020
gtggaacttg aaaactccat gggaggtttg aactttggcc gatcttactt tgatccagca 1080
tattttagat tagggcaaga gatggtaagg aggtcagctg gaaaggtcag ttccacattg 1140
gcatctgaac tcggtatcac tgccgaggat gcaaggcttg tttcagagat tgcaatgcat 1200
actactgagg acaagatcag tagagcggtt ggacccagac aagcccaagt atcatttcta 1260
cacggtgatc aaagtgagaa tgagctaccg agattggggg gcaaggaaga taggagggtc 1320
aaacagagtc gaggagaagc cagggagagc tacagagaaa ccgggcccag cagagcaagt 1380
gatgcgagag ctgcccatct tccaaccggc acacccctag acattgacac tgcaacggag 1440
tccagccaag atccgcagga cagtcgaagg tcagctgacg ccctgcttag gctgcaagcc 1500
atggcaggaa tctcggaaga acaaggctca gacacggaca cccctatagt gtacaatgac 1560
agaaatcttc tagacggcgc cgcgggagca ggtgcaggag atagggtggc agatgtaatt 1620
gaaagctcca taggagatag cgtgagcaga gccctcactc acgctctacc agcacccaca 1680
ggtcagaaca cacaggtgag cagtcatcga ctggatacgg gcaaggttcc agcactccaa 1740
gctgctgaaa ttggagcatc atcaaatgct agtgacgaga gtatgattga gacacgctgt 1800
gtcctcaact cgcacagtac agcagagacc actcttgata gtttcttcag cagggcggga 1860
ttagttggag agatagatct ccctcttgag ggcacaacta acccaaatgg ttatgccaac 1920
tgggacatag atataacagg ttacgcgcaa atgcgtagaa aggtagagct cttcacctac 1980
atgcgctttg atgcagagtt cacttttgtt gcgtgtacac ctaccgggga agttgttcca 2040
caactgctcc aatatatgtt tgtgccacct ggagccccaa agccagattc tagggaatcc 2100
cttgcatggc aaaccgccac taacccctca gtttttgtca agctgtcaga ccctccagca 2160
caggtttcag tgccattcat gtcacctgcg agtgcttatc aatggtttta tgacggatat 2220
cccacgttcg gagaacacaa acaggagaaa gatcttgaat atggggcatg tcctaataac 2280
atgatgggca cgttctcagt gcggactgta gggtcctcca agtccaagta ccctctagtg 2340
attaggattt acatgagaat gaagcacgtc agggcgtgga tacctcgccc gatgcgtaac 2400
cagaactacc tattcaaagc caatccaaat tatgctggca actccgttaa gccaactggt 2460
gccagtcgca cagcgatcac cactctttga tga 2493

<210> SEQ ID NO 37
<211> LENGTH: 2493
<212> TYPE: DNA

```
<213> ORGANISM: Artificial Sequence
<220> FEATURE:
<223> OTHER INFORMATION: Optimized nucleotide sequence of the
      polynucleotide encoding the N-VP1 fusion protein (the
      nucleoprotein N is obtained from the Schwarz strain) including the
      nucleotide sequence encoding the peptide linker disclosed as
      sequence SEQ ID No: 26

<400> SEQUENCE: 37

atggccacgt tattgagatc tttagccctt tttaagagga acaaggacaa acccccaatt     60

acaagtggtt ctggtggagc tattcgtggt attaagcaca ttattatcgt gcccattcca    120

ggggattcaa gtatcaccac ccgaagtaga ttgttggaca gattggtccg acttataggg    180

aacccagacg ttagtggacc caagctgacc ggggctctga tcggaatctt atctttgttc    240

gttgaatctc caggacagtt aatccaaagg attacagacg atccagacgt ctctattagg    300

cttctagagg ttgttcagtc tgaccagtct caatccggtc ttaccttcgc ttcaagaggt    360

accaatatgg aggacgaagc cgatcaatat ttctcacatg acgatcctat ctcctccgac    420

caatcaagat ttggttggtt cggaaacaaa gagatctctg acattgaggt tcaggaccca    480

gaaggattta acatgatact gggaactatc cttgcacaaa tctgggtgct gctggctaaa    540

gccgttactg ctccagacac cgctgctgat tccgaattac gaagatggat taaatacact    600

caacaacgta gagtagttgg tgaatttaga ttggagagaa agtggttgga tgttgtgaga    660

aacagaattg cagaagacct atcactgaga cgatttatgg tcgctcttat actggatatt    720

aagaggacac caggaaacaa gccaaggatt gcagaaatga tctgtgatat agatacttac    780

atcgttgagg ccgggttggc ttcctttatt ctaactataa aatttggtat cgagacaatg    840

tacccagcat tgggattgca tgagttcgcc ggagaactgt caacattgga gtcattgatg    900

aatctatacc agcaaatggg tgaaacagct ccatatatgg tcattctgga aaactccatt    960

caaaacaagt tttcagccgg ttcataccca ttattgtggt cttacgccat gggagtcggt   1020

gtagagctgg aaaactctat gggtggcctt aatttcggca gatcttattt tgatcccgct   1080

tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcaacggaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagatggcgc cgcgggtgct ggtgccggag atagagtcgc cgatgttatt   1620

gagtcttcca ttggagattc agttagtaga gccttgacac acgccttgcc agccccaacc   1680

ggacaaaaca ctcaggtttc ttcccataga ttggatacag gaaaggtccc tgctcttcaa   1740

gctgccgaga ttggtgcctc aagtaacgca tctgacgaat ccatgatcga gactagatgt   1800

gttttgaatt cacacagtac agctgaaact acattggatt catttttcag tagagccggt   1860

cttgttggag agattgactt gccacttgaa ggtaccacta accctaatgg atacgccaac   1920

tgggatattg acatcactgg ttatgcacag atgagaagaa aagttgagtt gtttacctac   1980

atgagattcg atgcagaatt cactttcgtt gcttgcacac caaccggaga ggttgtccct   2040

caattgcttc agtatatgtt tgttccacct ggtgctccaa agcctgattc tagagaatcc   2100
```

```
ttggcttggc aaactgccac aaatccatcc gtttttgtca aactttcaga cccacctgct   2160

caagtttctg tcccattcat gtcacctgca agtgcttacc agtggtttta cgatggttat   2220

ccaactttcg gagaacataa gcaggagaaa gacttggaat atggtgcttg tcctaacaat   2280

atgatgggaa cattttctgt tagaaccgtc ggttcttcca agtccaagta cccattggtt   2340

attagaatct atatgagaat gaagcacgtc agagcatgga tcccaagacc tatgagaaac   2400

caaaattacc ttttcaaagc taaccctaat tatgcaggaa actcagtcaa gcctacagga   2460

gcatcaagaa ccgccatcac aacactttag taa                                2493
```

<210> SEQ ID NO 38
<211> LENGTH: 829
<212> TYPE: PRT
<213> ORGANISM: Artificial Sequence
<220> FEATURE:
<223> OTHER INFORMATION: Amino acid sequence of the polynucleotide encoding the N-VP1 fusion protein (the nucleoprotein N is obtained from the Schwarz strain) including the amino acid sequence of the peptide linker disclosed as sequence SEQ ID No: 27

<400> SEQUENCE: 38

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270
```

-continued

```
Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp Gly Ala Ala
        515                 520                 525

Gly Ala Gly Ala Gly Asp Arg Val Ala Asp Val Ile Glu Ser Ser Ile
    530                 535                 540

Gly Asp Ser Val Ser Arg Ala Leu Thr His Ala Leu Pro Ala Pro Thr
545                 550                 555                 560

Gly Gln Asn Thr Gln Val Ser Ser His Arg Leu Asp Thr Gly Lys Val
                565                 570                 575

Pro Ala Leu Gln Ala Ala Glu Ile Gly Ala Ser Ser Asn Ala Ser Asp
            580                 585                 590

Glu Ser Met Ile Glu Thr Arg Cys Val Leu Asn Ser His Ser Thr Ala
        595                 600                 605

Glu Thr Thr Leu Asp Ser Phe Phe Ser Arg Ala Gly Leu Val Gly Glu
    610                 615                 620

Ile Asp Leu Pro Leu Glu Gly Thr Thr Asn Pro Asn Gly Tyr Ala Asn
625                 630                 635                 640

Trp Asp Ile Asp Ile Thr Gly Tyr Ala Gln Met Arg Arg Lys Val Glu
                645                 650                 655

Leu Phe Thr Tyr Met Arg Phe Asp Ala Glu Phe Thr Phe Val Ala Cys
            660                 665                 670

Thr Pro Thr Gly Glu Val Val Pro Gln Leu Leu Gln Tyr Met Phe Val
        675                 680                 685

Pro Pro Gly Ala Pro Lys Pro Asp Ser Arg Glu Ser Leu Ala Trp Gln
```

```
    690                 695                 700

Thr Ala Thr Asn Pro Ser Val Phe Val Lys Leu Ser Asp Pro Pro Ala
705                 710                 715                 720

Gln Val Ser Val Pro Phe Met Ser Pro Ala Ser Ala Tyr Gln Trp Phe
                725                 730                 735

Tyr Asp Gly Tyr Pro Thr Phe Gly Glu His Lys Gln Glu Lys Asp Leu
            740                 745                 750

Glu Tyr Gly Ala Cys Pro Asn Asn Met Met Gly Thr Phe Ser Val Arg
        755                 760                 765

Thr Val Gly Ser Ser Lys Ser Lys Tyr Pro Leu Val Ile Arg Ile Tyr
    770                 775                 780

Met Arg Met Lys His Val Arg Ala Trp Ile Pro Arg Pro Met Arg Asn
785                 790                 795                 800

Gln Asn Tyr Leu Phe Lys Ala Asn Pro Asn Tyr Ala Gly Asn Ser Val
                805                 810                 815

Lys Pro Thr Gly Ala Ser Arg Thr Ala Ile Thr Thr Leu
            820                 825


<210> SEQ ID NO 39
<211> LENGTH: 1986
<212> TYPE: DNA
<213> ORGANISM: Artificial Sequence
<220> FEATURE:
<223> OTHER INFORMATION: Native nucleotide sequence of the
      polynucleotide encoding the N-Avidin fusion protein (the
      nucleoprotein N is obtained from the Schwarz strain) including the
      nucleotide sequence encoding the peptide linker disclosed as
      sequence SEQ ID No: 26

<400> SEQUENCE: 39

atggccacac ttttaaggag cttagcattg ttcaaaagaa acaaggacaa accacccatt     60

acatcaggat ccggtggagc catcagagga atcaaacaca ttattatagt accaatccct    120

ggagattcct caattaccac tcgatccaga cttctggacc ggttggtgag gttaattgga    180

aacccggatg tgagcgggcc caaactaaca ggggcactaa taggtatatt atccttattt    240

gtggagtctc caggtcaatt gattcagagg atcaccgatg accctgacgt tagcataagg    300

ctgttagagg ttgtccagag tgaccagtca caatctggcc ttaccttcgc atcaagaggt    360

accaacatgg aggatgaggc ggaccaatac ttttcacatg atgatccaat tagtagtgat    420

caatccaggt tcggatggtt cgggaacaag gaaatctcag atattgaagt gcaagaccct    480

gagggattca acatgattct gggtaccatc ctagcccaaa tttgggtctt gctcgcaaag    540

gcggttacgg ccccagacac ggcagctgat tcggagctaa gaaggtggat aaagtacacc    600

caacaaagaa gggtagttgg tgaatttaga ttggagagaa aatggttgga tgtggtgagg    660

aacaggattg ccgaggacct ctccttacgc cgattcatgg tcgctctaat cctggatatc    720

aagagaacac ccggaaacaa acccaggatt gctgaaatga tatgtgacat tgatacatat    780

atcgtagagg caggattagc cagttttatc ctgactatta agtttgggat agaaactatg    840

tatcctgctc ttggactgca tgaatttgct ggtgagttat ccacacttga gtccttgatg    900

aacctttacc agcaaatggg ggaaactgca ccctacatgg taatcctgga gaactcaatt    960

cagaacaagt tcagtgcagg atcatacccct ctgctctgga gctatgccat gggagtagga   1020

gtggaacttg aaaactccat gggaggtttg aactttggcc gatcttactt tgatccagca   1080

tattttagat tagggcaaga gatggtaagg aggtcagctg gaaaggtcag ttccacattg   1140

gcatctgaac tcggtatcac tgccgaggat gcaaggcttg tttcagagat tgcaatgcat   1200
```

actactgagg acaagatcag tagagcggtt ggacccagac aagcccaagt atcatttcta 1260
cacggtgatc aaagtgagaa tgagctaccg agattggggg gcaaggaaga taggagggtc 1320
aaacagagtc gaggagaagc cagggagagc tacagagaaa ccgggcccag cagagcaagt 1380
gatgcgagag ctgcccatct tccaaccggc acacccctag acattgacac tgcaacggag 1440
tccagccaag atccgcagga cagtcgaagg tcagctgacg ccctgcttag gctgcaagcc 1500
atggcaggaa tctcggaaga acaaggctca gacacggaca cccctatagt gtacaatgac 1560
agaaatcttc tagacggcgc cgcgggagca ggtgcagcca gaaagtgctc gctgactggg 1620
aaatggacca acgatctggg ctccaacatg accatcgggg ctgtgaacag cagaggtgaa 1680
ttcacaggca cctacatcac agccgtaaca gccacatcaa atgagatcaa agagtcacca 1740
ctgcatggga cacaaaacac catcaacaag aggacccagc ccacctttgg cttcaccgtc 1800
aattggaagt tttcagagtc caccactgtc ttcacgggcc agtgcttcat agacaggaat 1860
gggaaggagg tcctgaagac catgtggctg ctgcggtcaa gtgttaatga cattggtgat 1920
gactggaaag ctaccagggt cggcatcaac atcttcactc gcctgcgcac acagaaggag 1980
tagtag 1986

<210> SEQ ID NO 40
<211> LENGTH: 1986
<212> TYPE: DNA
<213> ORGANISM: Artificial Sequence
<220> FEATURE:
<223> OTHER INFORMATION: Optimized nucleotide sequence of the polynucleotide encoding the N-avidin fusion protein (the nucleoprotein N is obtained from the Schwarz strain) including the nucleotide sequence encoding the peptide linker disclosed as sequence SEQ ID No: 26

<400> SEQUENCE: 40
atggccacgt tattgagatc tttagccctt tttaagagga acaaggacaa acccccaatt 60
acaagtggtt ctggtggagc tattcgtggt attaagcaca ttattatcgt gcccattcca 120
ggggattcaa gtatcaccac ccgaagtaga ttgttggaca gattggtccg acttataggg 180
aacccagacg ttagtggacc caagctgacc ggggctctga tcggaatctt atctttgttc 240
gttgaatctc caggacagtt aatccaaagg attacagacg atccagacgt ctctattagg 300
cttctagagg ttgttcagtc tgaccagtct caatccggtc ttaccttcgc ttcaagaggt 360
accaatatgg aggacgaagc cgatcaatat ttctcacatg acgatcctat ctcctccgac 420
caatcaagat ttggttggtt cggaaacaaa gagatctctg acattgaggt tcaggaccca 480
gaaggattta acatgatact gggaactatc cttgcacaaa tctgggtgct gctggctaaa 540
gccgttactg ctccagacac cgctgctgat tccgaattac gaagatggat taaatacact 600
caacaacgta gagtagttgg tgaatttaga ttggagagaa agtggttgga tgttgtgaga 660
aacagaattg cagaagacct atcactgaga cgatttatgg tcgctcttat actggatatt 720
aagaggacac caggaaacaa gccaaggatt gcagaaatga tctgtgatat agatacttac 780
atcgttgagg ccgggttggc ttcctttatt ctaactataa aatttggtat cgagacaatg 840
tacccagcat tgggattgca tgagttcgcc ggagaactgt caacattgga gtcattgatg 900
aatctatacc agcaaatggg tgaaacagct ccatatatgg tcattctgga aaactccatt 960
caaaacaagt tttcagccgg ttcataccca ttattgtggt cttacgccat gggagtcggt 1020
gtagagctgg aaaactctat gggtggcctt aatttcggca gatcttattt tgatcccgct 1080

-continued

```
tattttagac tgggccaaga gatggtcaga cgttctgccg gaaaggtttc tagtactttg   1140

gctagtgaac taggtataac tgctgaggac gctagattgg tttctgaaat agctatgcac   1200

actactgaag ataagatcag tagggccgtt ggccctaggc aagctcaggt gtccttctta   1260

catggtgatc aatccgagaa tgagttgcct cgattgggag gcaaagagga ccgtagagtt   1320

aaacaatcta gaggagaggc acgtgaatct tacagagaga ccggtccatc ccgagcttct   1380

gatgcacgag ccgctcatct tcctaccggt acacctttag acattgatac ggcaacggaa   1440

tcatcccagg atccccaaga ttctagacgt tctgctgatg ctttactaag attgcaggct   1500

atggccggaa tttcagagga gcaaggttcc gacacagata ctccaattgt ctataatgac   1560

cgaaatctgt tagatggcgc cgcgggtgct ggtgccgcta gaaaatgttc acttactgga   1620

aaatggacaa atgaccttgg ttcaaatatg acaatcggtg ctgttaatag tcgtggtgaa   1680

ttcactggaa cttacattac tgctgttaca gccacctcta acgaaatcaa ggagtcccca   1740

ttgcatggta ctcaaaacac tattaacaag agaacccagc ctacttttgg attcacagtt   1800

aattggaagt tctcagaaag tactacagtc tttactggtc aatgtttcat tgatagaaac   1860

ggaaaggagg ttcttaaaac tatgtggttg cttagatctt ccgtcaatga catcggagat   1920

gactggaagg caaccagagt cggtattaac attttcacaa gattgagaac ccagaaggag   1980

tagtaa                                                              1986
```

<210> SEQ ID NO 41
<211> LENGTH: 660
<212> TYPE: PRT
<213> ORGANISM: Artificial Sequence
<220> FEATURE:
<223> OTHER INFORMATION: Amino acid sequence of the polynucleotide encoding the N-Avidin fusion protein (the nucleoprotein N is obtained from the Schwarz strain) including the amino acid sequence of the peptide linker disclosed as sequence SEQ ID No: 27

<400> SEQUENCE: 41

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
```

```
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp Gly Ala Ala
        515                 520                 525

Gly Ala Gly Ala Ala Arg Lys Cys Ser Leu Thr Gly Lys Trp Thr Asn
    530                 535                 540

Asp Leu Gly Ser Asn Met Thr Ile Gly Ala Val Asn Ser Arg Gly Glu
545                 550                 555                 560

Phe Thr Gly Thr Tyr Ile Thr Ala Val Thr Ala Thr Ser Asn Glu Ile
                565                 570                 575

Lys Glu Ser Pro Leu His Gly Thr Gln Asn Thr Ile Asn Lys Arg Thr
            580                 585                 590

Gln Pro Thr Phe Gly Phe Thr Val Asn Trp Lys Phe Ser Glu Ser Thr
        595                 600                 605
```

-continued

```
Thr Val Phe Thr Gly Gln Cys Phe Ile Asp Arg Asn Gly Lys Glu Val
    610                 615                 620

Leu Lys Thr Met Trp Leu Leu Arg Ser Ser Val Asn Asp Ile Gly Asp
625                 630                 635                 640

Asp Trp Lys Ala Thr Arg Val Gly Ile Asn Ile Phe Thr Arg Leu Arg
                645                 650                 655

Thr Gln Lys Glu
            660


<210> SEQ ID NO 42
<211> LENGTH: 110
<212> TYPE: DNA
<213> ORGANISM: Artificial Sequence
<220> FEATURE:
<223> OTHER INFORMATION: Nucleotide sequence of MV Schwarz Leader
      sequence (including the N start codon ATG)

<400> SEQUENCE: 42

accaaacaaa gttgggtaag gatagttcaa tcaatgatca tcttctagtg cacttaggat     60

tcaagatcct attatcaggg acaagagcag gattagggat atccgagatg               110


<210> SEQ ID NO 43
<211> LENGTH: 112
<212> TYPE: DNA
<213> ORGANISM: Artificial Sequence
<220> FEATURE:
<223> OTHER INFORMATION: Nucleotide sequence of MV Schwarz Trailer
      sequence

<400> SEQUENCE: 43

accagacaaa gctgggaata gaaacttcgt attttcaaag ttttctttaa tatattgcaa     60

ataatgccta accacctagg gcaggattag ggttccggag ttcaaccaat ta            112


<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

ttgttcagtc tgaccagtct c                                               21
```